United States Patent
Parry

(10) Patent No.: US 9,938,583 B2
(45) Date of Patent: Apr. 10, 2018

(54) BIOMARKERS FOR RADIATION TREATMENT

(71) Applicant: Varian Medical Systems, Inc., Palo Alto, CA (US)

(72) Inventor: Renate Parry, Palo Alto, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 0 days.

(21) Appl. No.: 14/777,209

(22) PCT Filed: Mar. 14, 2014

(86) PCT No.: PCT/US2014/029365
§ 371 (c)(1),
(2) Date: Sep. 15, 2015

(87) PCT Pub. No.: WO2014/144804
PCT Pub. Date: Sep. 18, 2014

(65) Prior Publication Data
US 2016/0024594 A1   Jan. 28, 2016

Related U.S. Application Data

(60) Provisional application No. 61/800,011, filed on Mar. 15, 2013.

(51) Int. Cl.
| | | |
|---|---|---|
| A61K 39/00 | (2006.01) | |
| C12Q 1/68 | (2018.01) | |
| A61K 31/337 | (2006.01) | |
| A61K 31/7115 | (2006.01) | |
| A61K 33/24 | (2006.01) | |
| A61K 39/395 | (2006.01) | |
| A61N 5/10 | (2006.01) | |
| G01N 33/574 | (2006.01) | |

(52) U.S. Cl.
CPC .......... *C12Q 1/6886* (2013.01); *A61K 31/337* (2013.01); *A61K 31/7115* (2013.01); *A61K 33/24* (2013.01); *A61K 39/3955* (2013.01); *A61N 5/1064* (2013.01); *G01N 33/57484* (2013.01); *A61N 2005/1098* (2013.01); *C12Q 2600/106* (2013.01); *C12Q 2600/158* (2013.01); *G01N 2333/4703* (2013.01); *G01N 2333/4712* (2013.01); *G01N 2333/70585* (2013.01); *G01N 2333/70596* (2013.01); *G01N 2333/90203* (2013.01); *G01N 2333/96494* (2013.01); *G01N 2400/40* (2013.01)

(58) Field of Classification Search
None
See application file for complete search history.

(56) References Cited

U.S. PATENT DOCUMENTS

| | | |
|---|---|---|
| 2010/0260667 A1 | 10/2010 | Georges et al. |
| 2012/0010230 A1 | 1/2012 | MacDougall et al. |
| 2012/0115165 A1 | 5/2012 | Franzmann |

FOREIGN PATENT DOCUMENTS

| | | |
|---|---|---|
| CN | 101993941 A | 3/2011 |
| JP | 2007518709 | 7/2007 |
| JP | 2009513161 | 4/2009 |
| JP | 2016521141 | 7/2016 |
| WO | 2011/127219 A1 | 10/2011 |
| WO | WO2011/127219 | * 10/2011 |
| WO | 2012131564 | 10/2012 |

OTHER PUBLICATIONS

Zhou et al, Amer J Path 182:1248-1254, online published Feb. 8, 2013.*
Chun et al, Intern J Radia Onco, 47:973-977, Jul. 2000.*
Xiao et al, Clin Exp Metastasis 29:1-9, online published Sep. 28, 2011.*
Choy et al, Semi Oncol 24: suppl 12, S12-21-S12-266, 1997, abstract only.*
Zhang et al, Can Res, 71:7155-67, 2011.*
International Search Report and Written Opinion dated Jul. 8, 2014 in PCT/US2014/029365, 11 pages.
Baumann et al., "CD44: A Cancer Stem Cell-Related Biomarker with Predictive Potential for Radiotherapy", Clinical Cancer Research, vol. 16, No. 21, Sep. 22, 2010, pp. 5091-5093.
Ducray et al., "An ANOCEF genomic and transcriptomic microarray study of the response to radiotherapy or to alkylating first-line chemotherapy in glioblastoma patients", Molecular Cancer, Biomed Central, London, GB, vol. 9, No. 1, Sep. 7, 2010, p. 234.
Goos, "Abstract 5217: MMP9 is a prognostic biomarker for metastatic colorectal cancer", Cancer Research, Apr. 15, 2011.
Komaki et al., "Vimentin (EMT Marker Protein) Score Predicts Resistance to Erlotinib and Radiation Therapy for Patients With Stage III Non-small Cell Lung Cancer on a Prospective Phase II Trial", International Journal of Radiation: Oncology Biology Physics, vol. 84, No. 3S, paragraph 59, Supplement 2012.
Oka et al., "Adenocarcinoma of the cervix treated with radiation alone: prognostic significance of S-1 00 protein and vimentin immunostaining.", Obstetrics and Gynecology, vol. 79, No. 3, Mar. 1992, pp. 347-350.

(Continued)

*Primary Examiner* — Lei Yao
(74) *Attorney, Agent, or Firm* — Kilpatrick Townsend & Stockton LLP

(57) ABSTRACT

The methods described herein allow for the classification of patients into groups for receiving optimized radiation treatment based on patient specific biomarker signature. The biomarker signature includes markers that have been shown to correlate with TGF-β expression and to be associated with tumor aggressiveness, radioresistance and poor prognosis. The markers play a key role in the epithelial-mesenchymal transition. The methods described herein provide the dual benefits of anti-tumor efficacy plus normal tissue protection when combining TGF-β inhibitors with ionizing radiation to treat cancer patients.

8 Claims, 11 Drawing Sheets

(56) References Cited

OTHER PUBLICATIONS

Xiao et al., "CD44 is a biomarker associated with human prostate cancer radiation sensitivity", Clinical & Experimental Metastasis; Official Journal of Themetastasis Research Society, Kluwer Academic Publishers, DO, vol. 29, No. 1, Sep. 28, 2011, pp. 1-9.
EP14762902.6, "Extended European Search Report", dated Jul. 27, 2016, 11 pages.
Cui et al., "Effects of Carbon Ion Beam on Putative Colon Cancer Stem Cells and Its Comparison with X-Rays", Cancer Research, vol. 71, No. 10, May 15, 2011, pp. 3676-3687.
Application No. JP2016-503075, "Office Action", dated Feb. 20, 2018, 10 pages.
Minoo et al., "Characterization of Rectal, Proximal and Distal Colon Cancers Based on Clinicopathological, Molecular and Protein Profiles", International Journal of Oncolofy, vol. 37, No. 3, Sep. 1, 2010, pp. 707-718.
Yaromina et al., "Individualization of Cancer Treatment from Radiotherapy Perspective", Molecular Oncology, vol. 6, No. 2, Apr. 2012, pp. 211-221.

\* cited by examiner

BIOMARKERS FOR RADIATION TREATMENT

CROSS-REFERENCE TO RELATED PATENT APPLICATIONS

This application is a National Stage of International Application No. PCT/US2014/029365, International Filing Date Mar. 14, 2014, which claims the benefit of priority to U.S. Provisional Patent Application No. 61/800,011, filed Mar. 15, 2013, wherein the entire disclosures of both applications are incorporated herein by reference.

BACKGROUND OF THE INVENTION

No validated protein signature is available that has been proved to be sufficiently useful in the clinic to stratify patients into groups that may be treated differently with radiotherapy. Many factors determine the biology of tumors and as such impact prognosis and survival outcome of cancer patients. TGF-β is a pleiotropic cytokine that is important in normal tissue homeostasis, regulates inflammation and immune responses, and controls proliferation and differentiation. TGF-β appears to be key in promoting epithelial-mesenchymal- transition (EMT), a process that leads to increased motility and invasion. Due to these oncogenic properties of TGF-β, several TGF-β signalling inhibitors are in preclinical and clinical trials to treat cancer. Radiotherapy is a corner stone of cancer therapy. There is substantial evidence that TGF-β plays a key role in the response to ionizing radiation. TGF-β is activated in irradiated tissues and plays a pivotal role in development of radiation induced fibrosis.

BRIEF SUMMARY OF THE INVENTION

The disclosure provides biomarkers that are useful for diagnosing and treating tumors or cancer in a subject. The disclosure further provides methods of treating tumors in a subject having modified (i.e., increased or decreased) levels of one or more biomarkers described herein. In some embodiments, methods for treating tumors were the level of one or more biomarkers is increased and the level of another biomarker is decreased are described. The disclosure also provides methods of diagnosing or identifying subjects in need of treatment based on the expression levels of the biomarkers described herein. In some embodiments, the treatment comprises administering ionizing radiation to the subject.

In one embodiment, the treatment comprises administering an increased dose of ionizing radiation to the subject if the level of one or more biomarkers described herein is modified in the tumor environment, where the dose of ionizing radiation is increased as compared to the standard of care for a subject that does not have modified levels of the biomarker(s) in the tumor environment. Alternatively, the treatment can comprise administering the same or a similar dose of ionizing radiation as the standard of care in combination with a pharmaceutically effective amount of an anti-cancer agent. For example, in some embodiments, if the subject is already undergoing treatment with ionizing radiation, the amount of ionizing radiation administered to the tumor or subject is maintained at the current treatment dose and/or interval, and an anti-cancer agent is administered to the subject if the level of one or more biomarkers described herein is modified in the tumor environment.

In one aspect, the method comprises modifying the standard radiation treatment protocol if the level of a biomarker described herein is modified in the tumor environment. In some embodiments, the standard radiation treatment protocol is modified by increasing the dose of ionizing radiation administered to the tumor. In some embodiments, the standard radiation treatment protocol is modified by hypofractionation or hyperfractionation of the dose of ionizing radiation. In some embodiments, the standard radiation treatment protocol is modified by further administering an anti-cancer agent or TGF-beta inhibitor to the subject.

In some embodiments, the method comprises modifying the standard radiation treatment protocol if the level of a biomarker selected from the group consisting of CD44, MMP9, ALDH1A1, Vimentin, hyaluronan, beta-catenin, MFG-E8 and CD68 is modified in the tumor environment. The level of a biomarker is modified if the level is increased or decreased compared to the level of the biomarker in a normal (i.e., non-diseased) or control tissue.

In some embodiments, the method comprises modifying the standard radiation treatment protocol if the level of CD68 is increased in the tumor environment. In some embodiments, the method comprises modifying the standard radiation treatment protocol if the level of CD44 is increased in the tumor environment. In some embodiments, method comprises modifying the standard radiation treatment protocol if the level of CD44 is increased and the level of MFG-E8 is decreased in the tumor environment.

In some embodiments, the standard radiation treatment protocol is modified by increasing the dose of ionizing radiation administered to the tumor. In some, embodiments, the standard radiation treatment protocol is modified by hypofractionation. In some embodiments, standard radiation treatment protocol is modified by hyperfractionation.

In some embodiments, the treatment further comprises administering an anti-cancer agent to the subject. In some embodiments, the anti-cancer agent is a chemotherapeutic agent, radiosensitizer, or immune modulator. In some embodiments, the treatment further comprises administering a TGF-beta inhibitor to the subject. In some embodiments, the TGF-beta inhibitor is an antibody or a small molecule that neutralizes or inhibits TGF-beta function. In some embodiments, the TGF-beta inhibitor inhibits the production of TGF-beta.

In one embodiment, the method comprises:
(i) administering an increased dose of radiation to the subject, where the dose of radiation is increased compared to the dose administered to a subject that does not have elevated levels of CD68 in the tumor environment; or
(ii) administering a dose of radiation to the subject that is similar to the dose administered to a subject that does not have elevated levels of CD68 in the tumor environment in combination with a pharmaceutically effective amount of an anti-cancer agent,
thereby treating the tumor in the subject.

In one embodiment, the method comprises:
(i) administering an increased dose of radiation to the subject, where the dose of radiation is increased compared to the dose administered to a subject that does not have elevated levels of CD44 in the tumor environment; or
(ii) administering a dose of radiation to the subject that is similar to the dose administered to a subject that does not have elevated levels of CD44 in the tumor environment in combination with a pharmaceutically effective amount of an anti-cancer agent,
thereby treating the tumor in the subject.

In some embodiments, the disclosure provides a method for treating a tumor in a subject having increased levels of one or more biomarkers and decreased levels of another biomarker described herein. For example, in one embodiment, a method for treating a tumor in a subject having increased levels of CD44 and decreased levels of MFG-E8 in the tumor environment is described, the method comprising:
  (i) administering an increased dose of radiation to the subject, where the dose of radiation is increased compared to the dose administered to a subject that does not have elevated levels of CD44 and decreased levels of MEG-E8 in the tumor environment; or
  (ii) administering a dose of radiation to the subject that is similar to the dose administered to a subject that does not have elevated levels of CD44 and decreased levels of MFG-E8 in the tumor environment in combination with a pharmaceutically effective amount of an anti-cancer agent,
  thereby treating the tumor in the subject.

In some embodiments, the increased dose of radiation is administered in a hyperfractionated mode. In some embodiments, the increased dose of radiation is administered in a hypofractionated mode.

In some embodiments, the anti-cancer agent is a chemotherapeutic agent, radiosensitizer, or immune modulator. In some embodiments, the anti-cancer agent is an antibody that neutralizes or inhibits TGF-beta function. In one embodiment, the anti-cancer agent is a small molecule that neutralizes or inhibits TGF-beta function. In some embodiments, the anti-cancer agent inhibits the production of TGF-beta.

In another aspect, the disclosure provides a method for treating a tumor in a subject in need thereof, the method comprising:
  (a) determining an expression level of two or more biomarkers in a tumor sample from the subject, wherein the two or more biomarkers are selected from the group consisting of CD44, MMP9, ALHD1A1 Vimentin, hyaluronan, beta-catenin, MFG-E8, and CD68;
  (b) comparing the expression level of the two or more biomarkers to an expression level in a normal tissue sample; and
  treating the tumor if the expression level of the two or more biomarkers is modified compared to the expression level in the normal tissue sample.

In another aspect, a method of identifying a subject as a candidate for treatment with ionizing radiation is disclosed, the method comprising:
  (a) determining an expression level of two or more biomarkers in a tumor sample from the subject, wherein the one or more biomarkers are selected from the group consisting of CD44, MMP9, ALDH1A1. Vimentin, hyaluronan, beta-catenin, MFG-E8, and CD68; and
  (b) comparing the expression level of the two or more biomarkers to an expression level in a normal tissue sample;
  wherein an expression level of the the two or more biomarkers in the tumor sample that is modified compared to the expression level in the normal tissue sample identifies the subject as a candidate fix treatment with ionizing radiation.

In another aspect a method of treating a subject having a tumor is disclosed, the method comprising:
  administering ionizing radiation to a subject that has been selected as having an expression level of two or more biomarkers in a tumor sample that is modified relative to an expression level in a normal tissue sample;
  wherein the two or more biomarkers are selected from the group consisting of CD44, MMP9, ALDH1A1, Vimentin, hyaluronan, beta-catenin, MFG-E8, and CD68;
  thereby treating the tumor in the subject.

In another aspect, a method for selecting a treatment for a subject g a tumor is disclosed, the method comprising:
  (a) determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68;
  (b) comparing the expression level of the two or more biomarkers to an expression level in a normal tissue sample; and
  selecting a treatment if the expression level of the two or more biomarkers is modified compared to the expression level in the normal tissue sample.

In the methods, the expression level of the two or more biomarkers is modified if the expression level of at least one of the biomarkers is increased, or if the expression level of at least one of the biomarkers is decreased, or if the expression level of at least one of the biomarkers is increased and the expression level of at least one of the biomarkers is decreased compared to the expression level in a normal tissue sample.

In the above aspects, the treatment comprises administering ionizing radiation to the tumor. In some embodiments, the treatment further comprises contacting the tumor with a radiosensitizer. In one embodiment, the treatment further comprises administering a compound that inhibits TGF-beta signaling to the subject.

In some embodiments, the tumor sample is a biopsy comprising tumor cells. In one embodiment, the tumor is a lung cancer tumor and the tumor sample comprises lung cancer cells. In some embodiments, the biomarker is a gene, an RNA, an extracellular matrix component, or a protein. In some embodiments, the expression level of the biomarker is determined by detecting the expression of an RNA and/or a protein. For example, the expression level can be detected by immunohistochemistry, ELISA, Western analysis, HPLC, proteomics, PCR, RT-PCR, Northern analysis, and/or nucleic acid or polypeptide microarrays.

In some embodiments, the normal tissue sample comprises non-tumor cells from the same tissue type as the tumor.

In some embodiments, the expression level of the two of more biomarkers is ranked or weighted. The expression level of each of CD44, MMP9, ALDH1A1, Vimentin, hyalurnan, beta-catenin, MFG-E8 and CD68 can be determined. In one embodiment, the expression level of at least one additional biomarker from the tumor sample is determined.

In some embodiments, an existing treatment and/or treatment plan is modified if the expression level of the two or more biomarkers is increased or decreased compared to the expression level of the same biomarker in the normal tissue sample. For example, the existing treatment and/or treatment plan can be modified to increase or decrease the effective dose of ionizing radiation administered to the tumor. The effective dose can be increased by increasing the amount of ionizing radiation administered to the tumor and/or contacting the tumor with a radiosensitizer.

In another aspect, a kit is provided, the kit comprising reagents capable of detecting the expression of a biomarker selected from the group consisting of CD44, MMP9, ALDH1A1, Vimentin, hyaluronan, beta-catenin, MFG-E8, and CD68.

In some embodiments, one or more of the steps of the methods described herein are carried out in vitro. For example, the expression level of the biomarkers described herein can be determined in vitro using immunohistochemistry techniques on tissue samples isolated from a subject. Thus, the step of determining the expression level of the biomarkers described herein does not require that the determining step be performed in vivo (i.e., in the subject), in certain embodiments, the expression level of the biomarkers described herein is ranked or weighted using software providing instructions to a computer.

In some aspects, the disclose provides a biomarker composition for use in a method for treating or diagnosing cancer or tumors. In some embodiments, a composition comprising a biomarker selected from CD44, MMP9ALDH1A1, Vimentin, hyalurnan, beta-catenin, MFG-E8 and/or CD68 for use in a method for treating tumors is provided. In some embodiments, the disclosure provides a biomarker in combination with ionizing radiation for use in a method for treating a tumor. For example, a composition comprising a biomarker selected from CD44, MMP9, ALDH1A1, Vimentin, hyalurnan, beta-catenin, MFG-E8 and/or CD68 in combination with ionizing radiation for use in a method for treating tumors in provided.

In some embodiments, the disclosure describes a composition comprising a biomarker selected from CD44, MMP9, ALDH1A1, Vimentin, hyalurnan, beta-catenin, MFG-E8 and/or CD68 for use in a method for treating tumors, the method comprising modifying the standard radiation treatment protocol if the level of a biomarker described herein is increased in the tumor environment. In some embodiments, the standard radiation treatment protocol is modified by increasing the dose of ionizing radiation administered to the tumor. In some embodiments, the standard radiation treatment protocol is modified by hypofractionation or hyperfractionation of the dose of ionizing radiation. In some embodiments, the standard radiation treatment protocol s modified by further administering an anti-cancer agent to the subject.

In some embodiments, the disiscosure describes the use of a composition comprising a biomarker selected from CD44, MMP9, ALDH1A1, Vimentin, hyalurnan, beta-catenin, MFG-E8 and/or CD68 in a method for treating a tumor, the method comprising
(i) administering an increased dose of radiation to the subject, where the dose of radiation is increased compared to the dose administered to a subject that does not have elevated levels of a biomarker selected from CD44, MMP9ALDH1A1, Vimentin, hyalurnan, beta-catenin, MFG-E8 and/or CD68 in the tumor environment; or
(ii) administering a dose of radiation to the subject that is similar to the dose administered to a subject that does not have elevated levels of a biomarker selected from CD44, MMP9, ALDH1A1, Vimentin, hyalurnan, beta-catenin, MFG-E8 and/or CD68 in the tumor environment in combination with a pharmaceutically effective amount of an anti-cancer agent.

In some embodiments, a composition comprising a biomarker selected from CD44, MMP9, ALDH1A1, Vimentin, hyalurnan, beta-catenin, MFG-E8 and/or CD68 for use in a diagnostic method practiced on the humand or animal body is provided. In one embodiment, a composition comprising a biomarker selected from CD44, MMP9, ALDH1A1, Vimentin, hyalurnan, beta-catenin, MFG-E8 and/or CD68 for use in diagnosing or prognosing cancer or tumors is provided. For example, a composition comprising a biomarker selected from CD44, MMP9, ALDH1A1, Vimentin, hyalurnan, beta-catenin, MFG-E8 and/or CD68 for use in diagnosing tumors is provided, the use comprising:
(a) determining an expression level of a biomarker in a biological or tissue sample from the subject, wherein the biomarker is selected from the group consisting of CD44, MMP9, ALDH1A1, Vimentin, hyaluronan, beta-catenin, MFG-E8, and CD68; and
(b) comparing the expression level of the biomarker(s) to an expression level in a normal biological or tissue sample;

wherein an expression level of the biomarker(s) in the biological or tissue sample that is increased or decreased compared to the expression level in the normal biological or tissue sample provides a diagnosis that the subject suffers from a tumor. The use can also provide a prognosis regarding the course of disease, or can be used to identify a subject as a candidate for treatment with ionizing radiation.

DEFINITIONS

The term "treating" refers to administering a treatment to a tumor or the subject diagnosed with a tumor. Examples of treatments include ionizing radiation, a chemotherapeutic treatment, or a combination of both. The treatment can also include a radiosensitizer. The term also includes selecting a treatment or treatment plan, and providing treatment options to a healthcare provider or the subject.

The term "ionizing radiation" refers to radiation comprising particles having enough kinetic energy to discharge an electron from an atom or molecule, thereby producing an ion. The term includes both directly ionizing radiation, such as that caused by atomic particles such as alpha particles (helium nuclei), beta particles (electrons), and protons, and indirectly ionizing radiation, such as photons, including gamma rays and x-rays. Examples of ionizing radiation used in radiation therapy include high energy x-rays, electron beams, and proton beams.

The term "tumor environment" or "tumor micro-environment" refers to the immediate small-scale environment of an organism or part of an organism, especially as a distinct part of a larger environment, for example, the immediate small-scale environment of the tumor. The term includes not only the tumor cells themselves, but associated blood-vessels (including endothelial cells and smooth muscle cells), immune system cells and secreted cytokines, epithelial cells, fibroblasts, connective tissue, and/or extracellular matrix that is associated with or surrounds the tumor. The term also refers to the cellular and extracellular environment in which the the tumor is located.

The term "standard of care" or "standard radiation treatment protocol" in radiation therapy generally refers to the ionizing radiation dose and administration interval that is generally accepted in the medical field as appropriate treatment for a given tumor, based on the tumor type, size, tissue location, and various other biological parameters. The standard of care or standard treatment protocol varies and is dependent on several factors. For example, for radiation therapy of lung cancer, the standard of care includes multiple fractions (e.g., approximately 30 fractions of low dose radiation, or approximately 60 Gy over 6 weeks) or a smaller number of fractions (e.g., 1-5 fractions) of biologically active doses (e.g., 54 GY in 3 fractions for peripheral tumors, or 48-60 Gy in 4-8 fractions for central tumors) administered to the tumor.

The term "similar dose of ionizing radiation" refers to a dose of ionizing radiation that is identical to, nearly the same, or substantially the same as the effective dose administered to a tumor in another subject, or administered to a tumor in the same subject undergoing an existing course of treatment. The term encompasses the normal and expected variation in ionizing radiation doses delivered by a medical technician skilled in the art of administering ionizing radiation to a tumor in a subject. For example, the term encompasses variation in the effective dose administered to a tumor of less than 10%, less than 5%, or less than 1%. The subject can be a human or non-human animal, such as a companion animal (e.g., cat, dog) or farm animal (e.g., cow, horse, etc.).

The term "small molecule" refers to an organic compound having a molecular weight of less than about 900 daltons, or less than about 500 daltons. The term includes drugs having desired pharmacological properties, and includes compounds that can be taken orally or by injection. The term includes organic compounds that modulate the activity of TGF-beta and/or other molecules associated with enhancing or inhibiting an immune response.

DETAILED DESCRIPTION OF THE INVENTION

Figure 1:
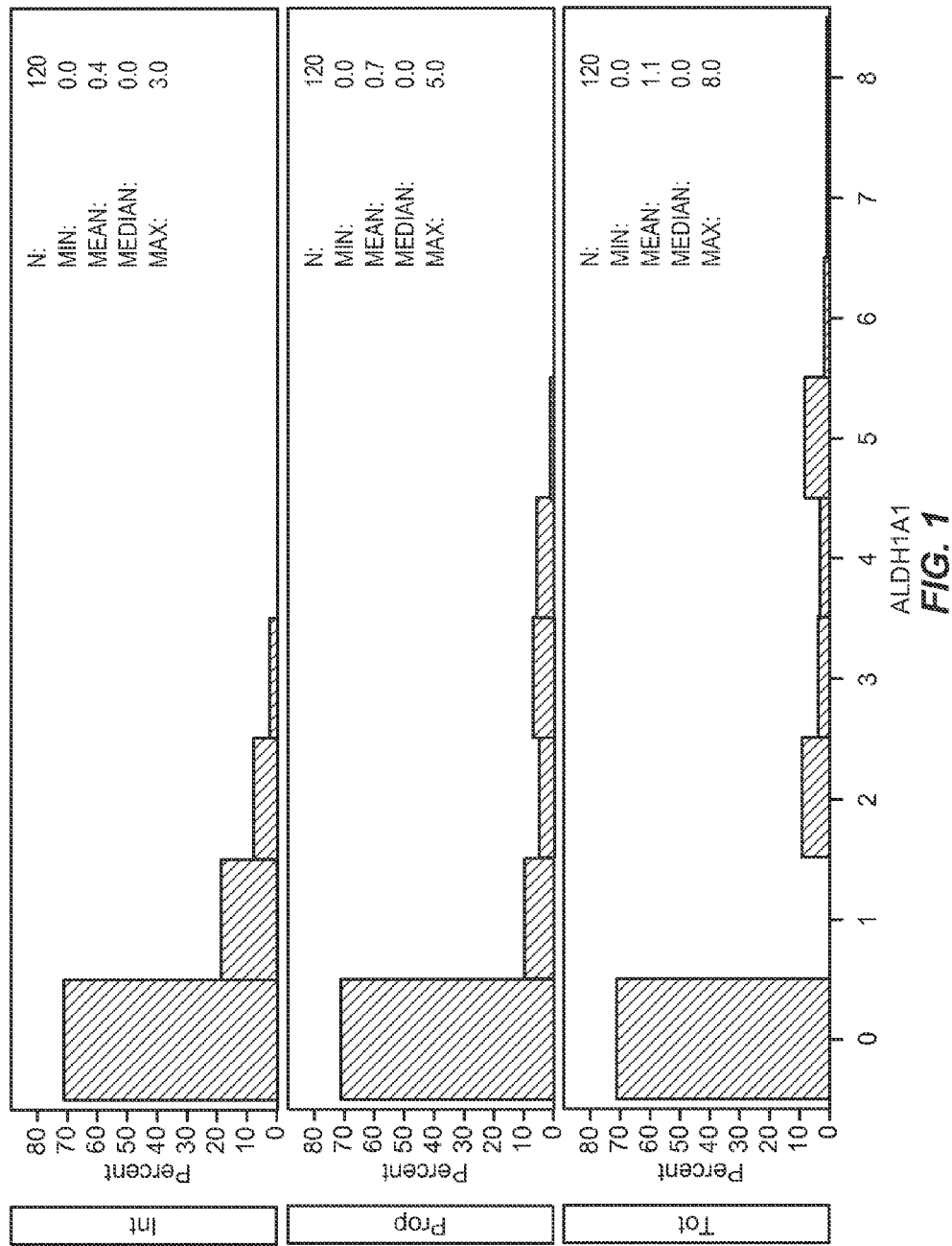
FIG. 1 shows the distribution of ALDH1A1 in biopsy samples from lung cancer patients.
Figure 2:
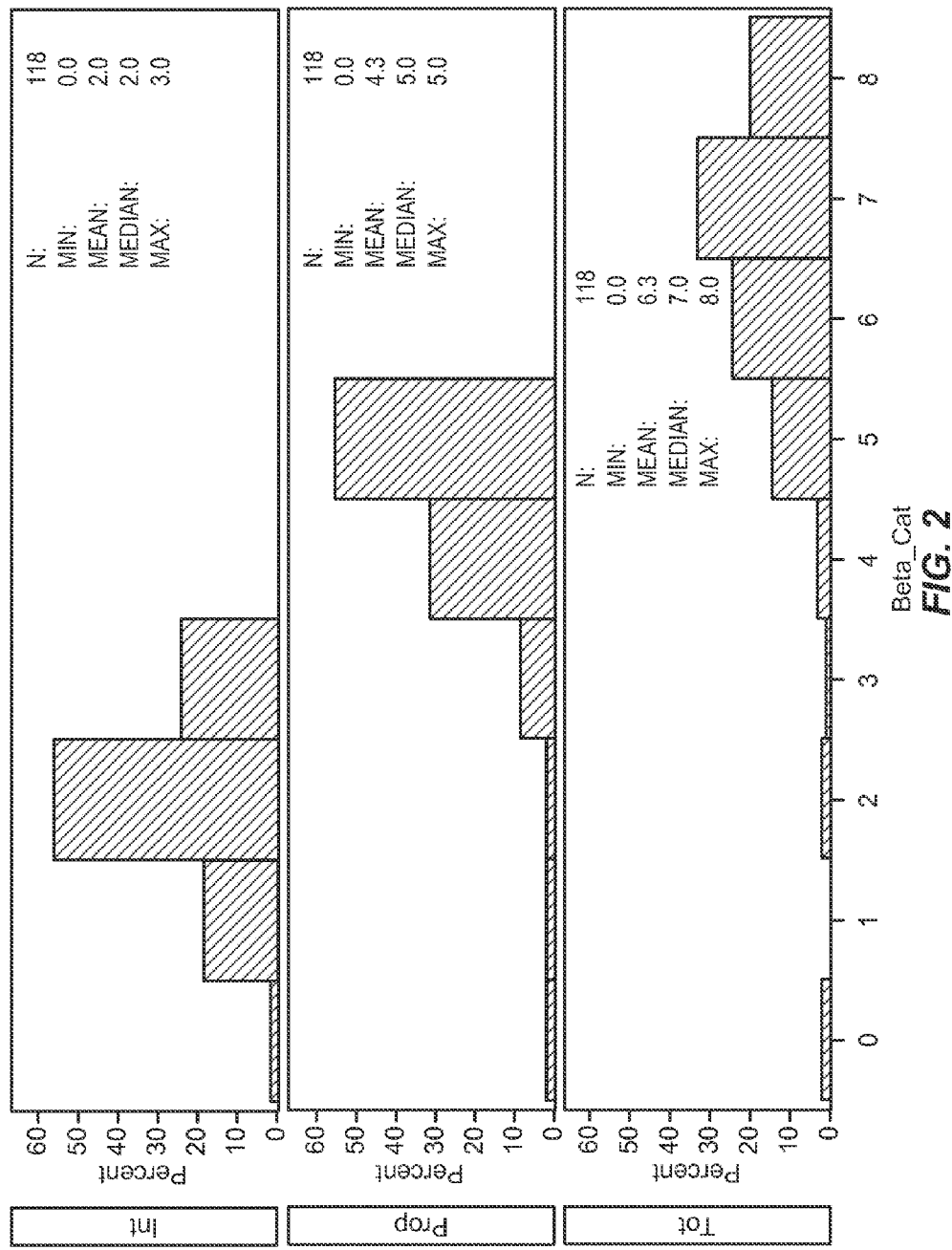
FIG. 2 shows the distribution of Beta-Cat in biopsy samples from lung cancer patients.
Figure 3:
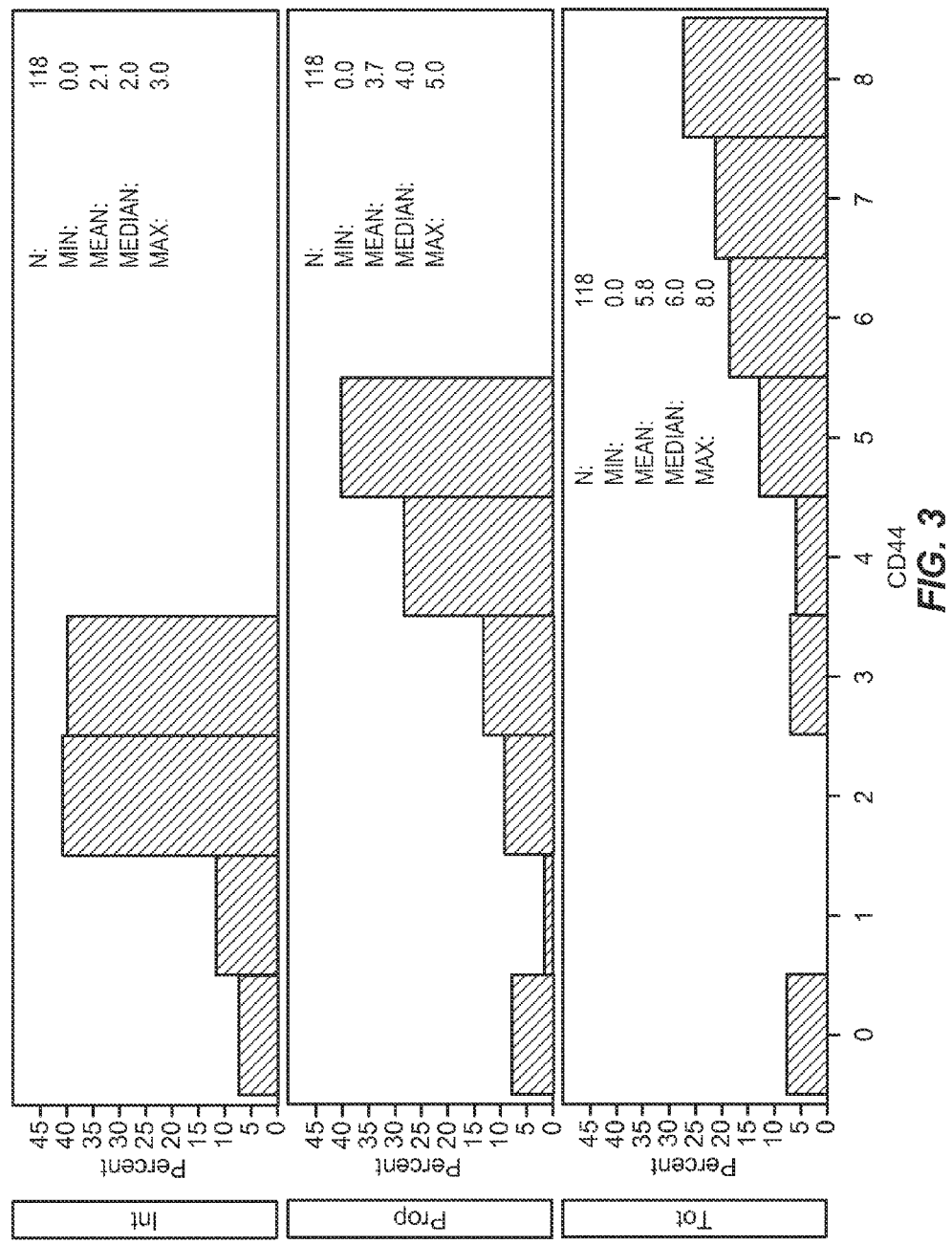
FIG. 3 shows the distribution of CD44 in biopsy samples from lung cancer patients.
Figure 4:
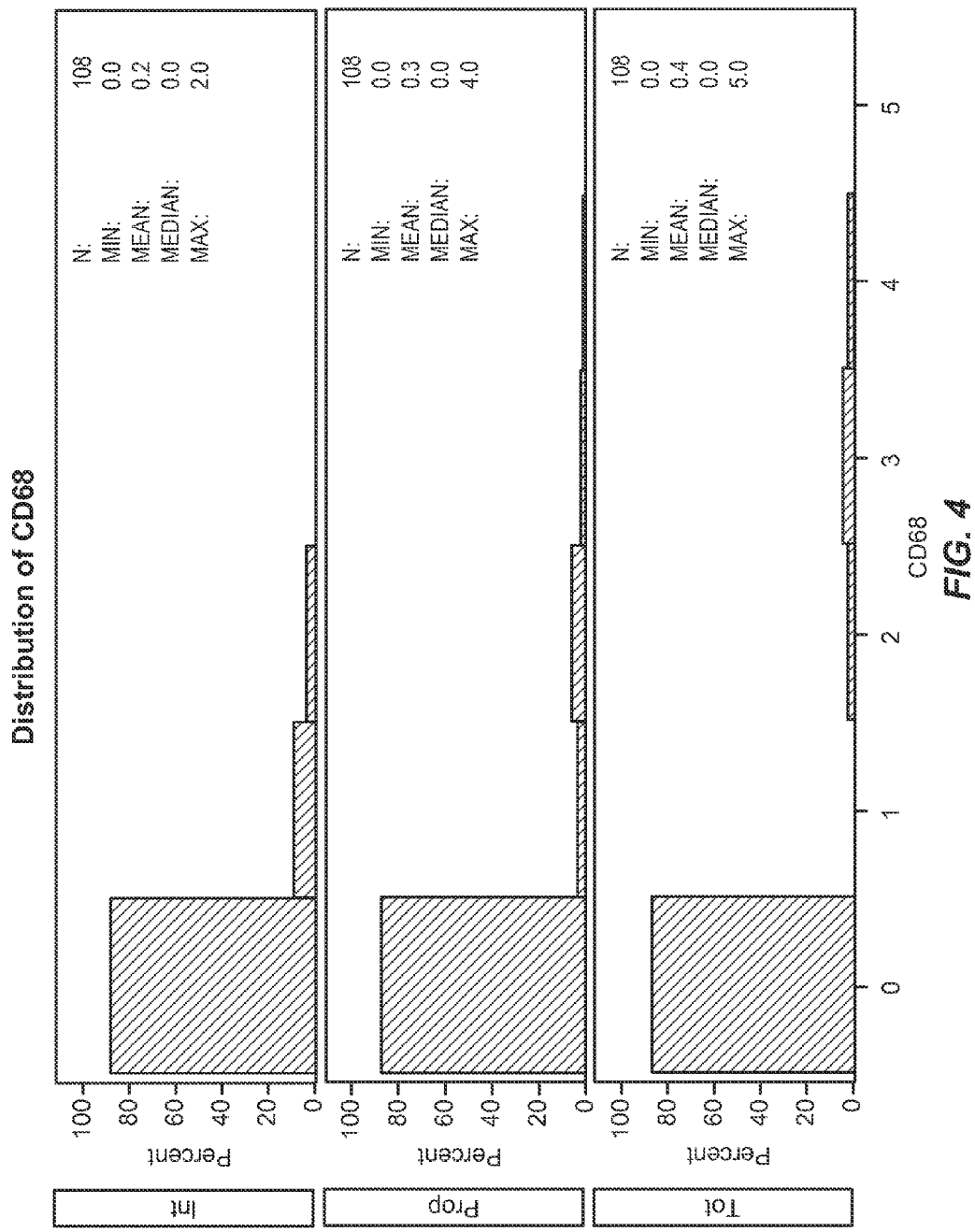
FIG. 4 shows the distribution of CD68 in biopsy samples from lung cancer patients.
Figure 5:
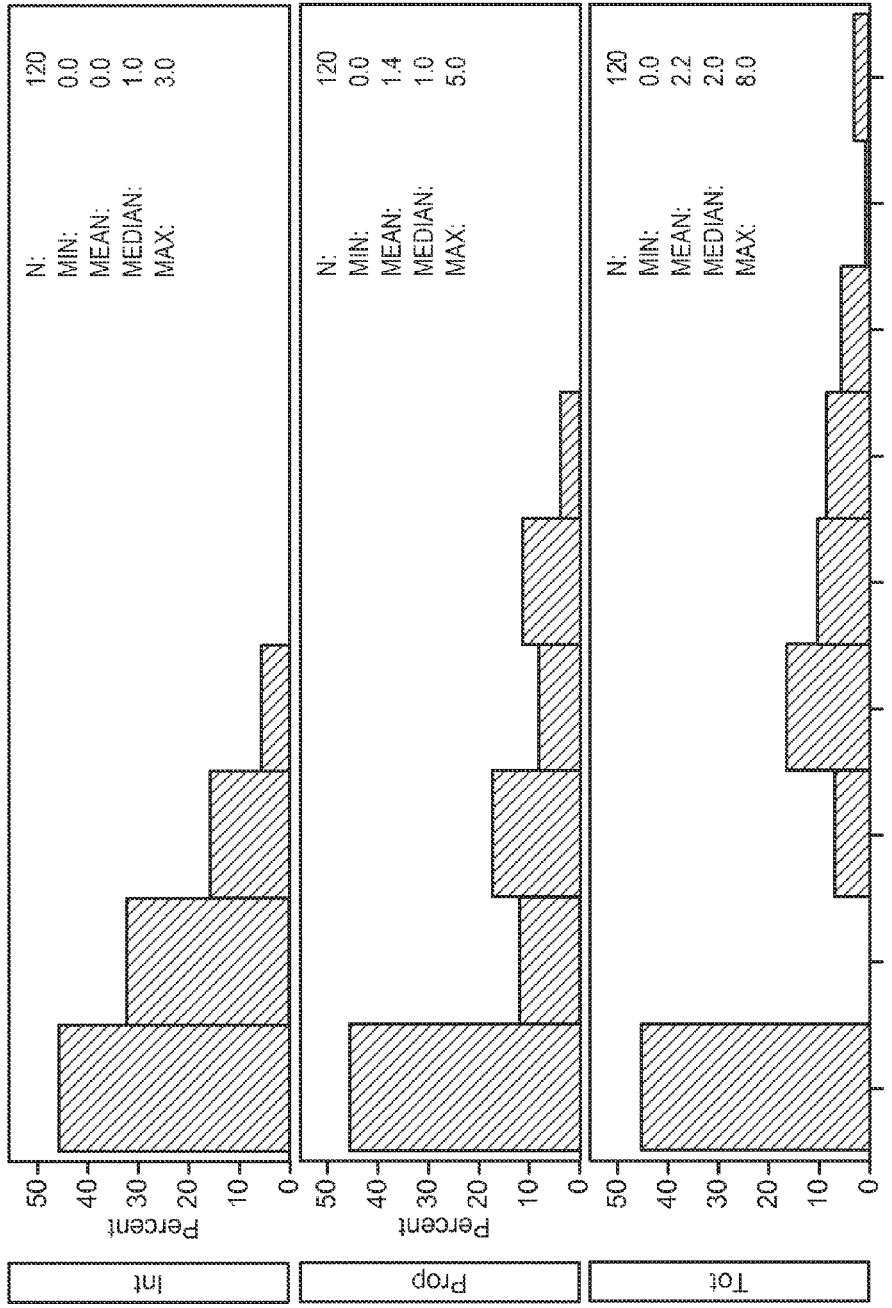
FIG. 5 shows the distribution of HA in biopsy samples from lung cancer patients.
Figure 6:
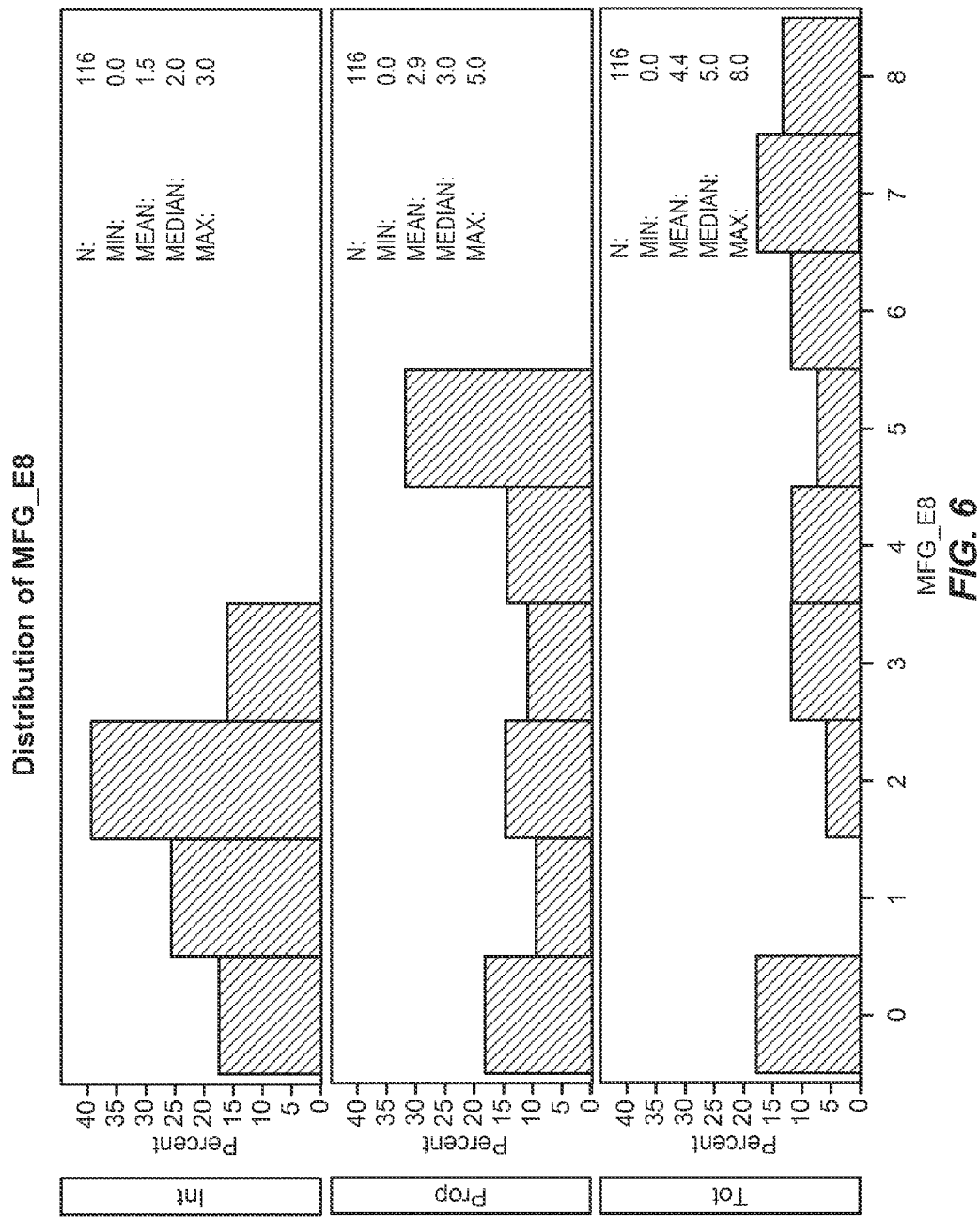
FIG. 6 shows the distribution of MFG-E8 in biopsy samples from lung cancer patients.
Figure 7:
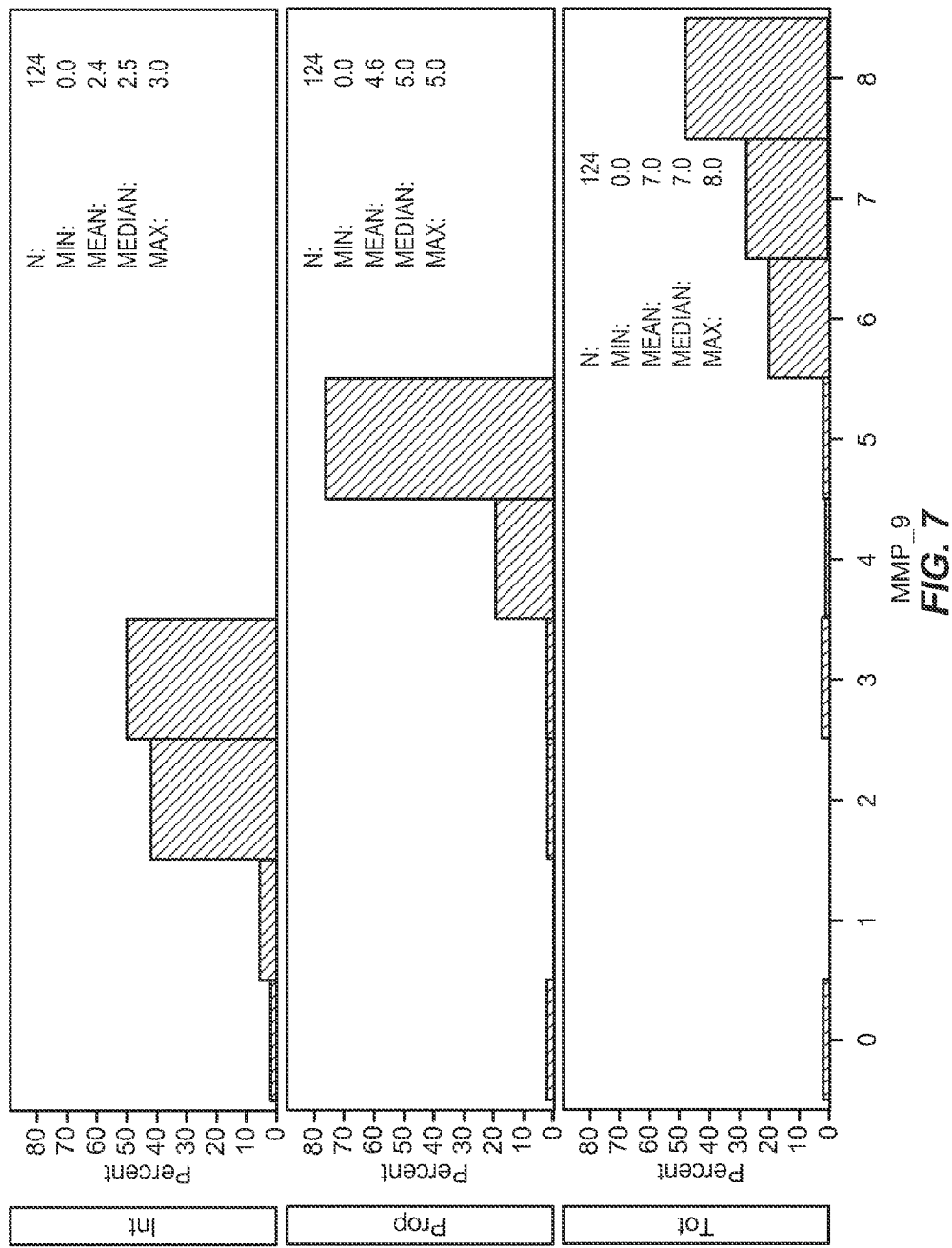
FIG. 7 shows the distribution of MMP9 in biopsy samples from lung cancer patients.
Figure 8:
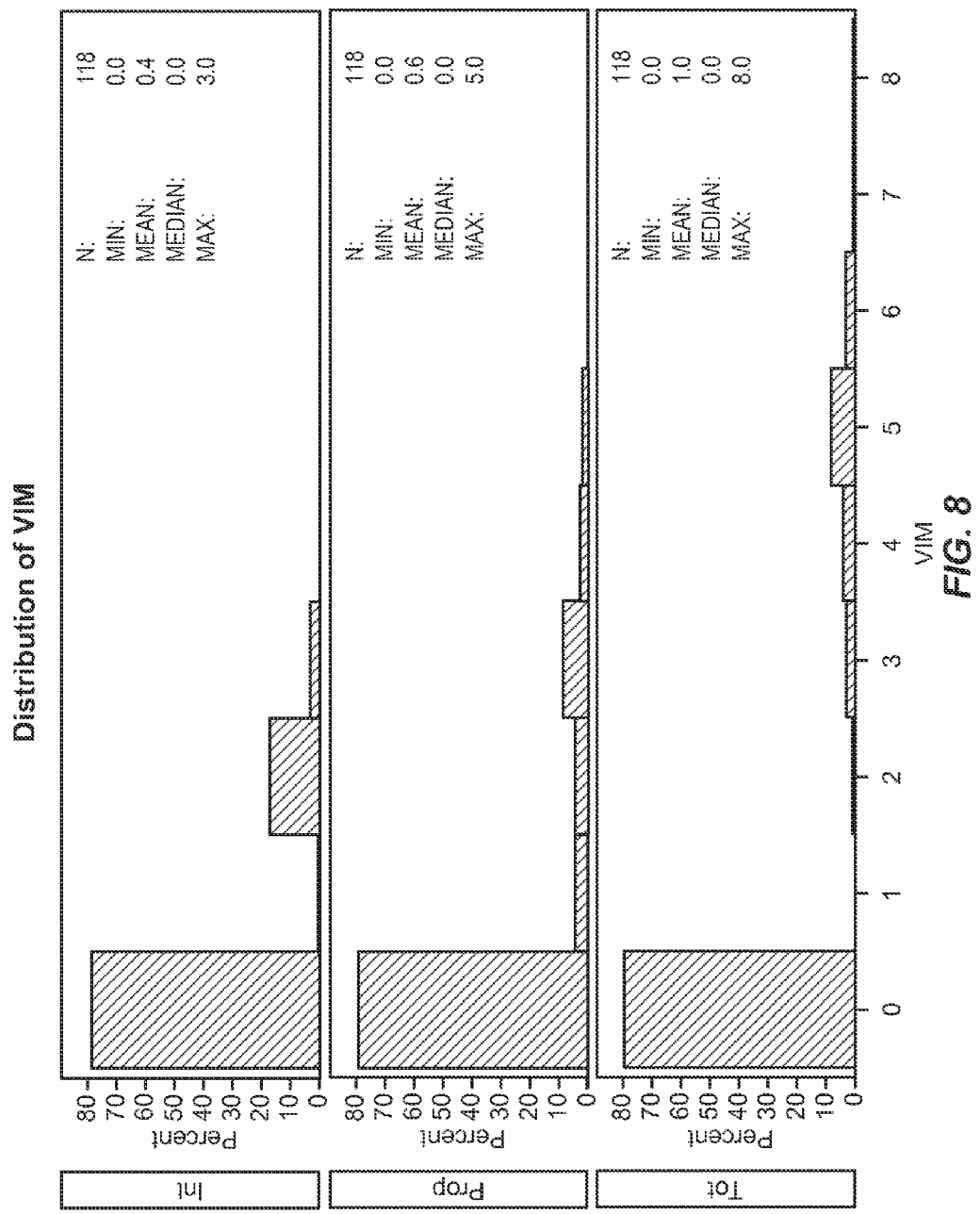
FIG. 8 shows the distribution of VIM in biopsy samples from lung cancer patients.

The methods described herein allow for the classification of patients into groups for receiving optimized radiation treatment based on patient specific biomarker signature. The biomarker signature includes markers that have been shown to correlate with TGF-β expression and to be associated with tumor agressiveness, radioresistance and poor prognosis. The markers play a key role in the epithelial-mesenchymal transition. The methods described herein provide the dual benefits of anti-tumor efficacy+normal tissue protection when combining TGF-β inhibitors with ionizing radiation to treat cancer patients.

I. Methods

The present disclosure describes methods for treating a tumor in a subject by determining the expression levels of signature biomarkers in a tumor sample, comparing the expression levels in the tumor sample to the expression levels in a normal tissue sample, and treating the tumor if the expression levels in the tumor sample are different from those in the normal tissue sample. In some embodiments, the treatment is ionizing radiation. Thus, the biomarkers provide so called "companion diagnostics" for radiation therapy to treat tumors. The signature biomarkers can also be used to select the appropriate treatment when ionizing radiation is combined with therapeutic tumor treatments such as chemotherapy. Many of the signature biomarkers disclosed herein are associated with the TGF-β signalling pathway. Thus, in some embodiments, the therapeutic agent is an inhibitor of TGF-β or an inhibitor of a component of the TGF-β signalling pathway.

In one aspect, the method is for treating a tumor. The method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68. The expression levels of the two or more biomarkers in the tumor sample are compared to the expression levels of the two or more biomarkers in a normal tissue sample. If the expression levels of the two or more biomarkers in the tumor sample are different from the expression levels in the normal tissue sample, for example, increased or decreased relative to the normal tissue level, the tumor is treated.

Thus, in some embodiments, the method comprises (a) determining an expression level of two or more biomarkers in a tumor sample from the subject, wherein the two or more biomarkers are selected from the group consisting of CD44, ALDH1A1, Vimentin, hyaluronan, beta-catenin, MFG-E8, and CD68; (b) comparing the expression level of the two or more biomarkers to an expression level in a normal tissue sample; and treating the tumor if the expression level of the two or more biomarkers is increased compared to the expression level in the normal tissue sample.

In some embodiments, the method comprises (a) determining an expression level of two or more biomarkers in a tumor sample from the subject, wherein the two or more biomarkers are selected from the group consisting of CD44, MMP9, ALDH1A1, Vimentin, hyaluronan, beta-catenin, and MFG-E8, and CD68; (b) comparing the expression level of the two or more biomarkers to an expression level in a normal tissue sample; and treating the tumor if the expression level of the two or more biomarkers is decreased compared to the expression level in the normal tissue sample.

In some embodiments, the method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68; and treating the tumor if the expression level of the two or more biomarkers is increased compared to the expression level in a normal tissue sample. In some embodiments, the method comprises determining an expression level of two or more biomarkers in a tumor sample from the subject, wherein the two or more biomarkers are selected from the group consisting of CD44, MMP9, ALDH1A1, Vimentin, hyaluronan, beta-catenin. MFG-E8, and CD68; and treating the tumor if the expression level of the two or more biomarkers is decreased compared to the expression level in a normal tissue sample.

In some embodiments, the treatment comprises administering ionizing radiation to the tumor. Thus, in some embodiments, the treatment comprises increasing the effective dose of ionizing radiation if the expression level of the two or more biomarkers is increased compared to the expression level in a normal tissue sample. In some embodiments, the treatment comprises decreasing the effective dose of ionizing radiation if the expression level of the two or more biomarkers is decreased compared to the expression level in a normal tissue sample.

In a second aspect, the disclosure describes a method for identifying a subject as a candidate for treatment with ionizing radiation. The method comprises determining an expression level of two or more biomarkers in a tumor sample from the subject, wherein the two or more biomarkers are selected from the group consisting of CD44, MMP9, ALDH1A1, Vimentin, hyalurnan, beta-catenin, MFG-E8, and CD68. As above, the expression levels of the two or more biomarkers in the tumor sample are compared to the expression levels of the two or more biomarkers in a normal tissue sample. If the expression levels of the two or more biomarkers in the tumor sample are different from the expression levels in the normal tissue sample, for example, increased or decreased relative to the normal tissue level, the subject is identified as a candidate for treatment with ionizing radiation.

In some embodiments, the expression level of the two or more biomarkers is increased compared to the expression level in the normal tissue sample, and the subject is identified as a candidate for a first treatment with ionizing radiation. In other embodiments, the expression level of the two or more biomarkers is decreased compared to the expression level in the normal tissue sample, and the subject is identified as a candidate for a second treatment with ionizing radiation. The first and second treatments can be the same or different. In some embodiments, the first treatment comprises increasing the effective dose of ionizing radiation. In some embodiments, the second treatment comprises decreasing the effective dose of ionizing radiation.

In a third aspect, a method is provided for treating a subject having a tumor. The method comprises administering ionizing radiation to a subject that has been selected as having an expression level of two or more biomarkers in a tumor sample that is increased or decreased relative to the expression level of the two or more biomarkers in a normal tissue sample. In some embodiments, the two or more biomarkers are selected from the group consisting of CD44, MMP9, ALDH1A1, Vimentin, hyalurnan, beta-catenin, MFG-E8, and CD68.

In some embodiments, the method comprises administering ionizing radiation to a subject that has been selected as having an expression level of two or more biomarkers in a tumor sample that is increased relative to the expression level of the two or more biomarkers in a normal tissue sample. In some embodiments, the method comprises administering ionizing radiation to a subject that has been selected as having an expression level of two or more biomarkers in a tumor sample that is decreased relative to the expression level of the two or more biomarkers in a normal tissue sample. In some embodiments, the dose of ionizing radiation administered to the subject is increased if the expression level of two or more biomarkers in a tumor sample is increased relative to the expression level of the two or more biomarkers in a normal tissue sample. In some embodiments, the dose of ionizing radiation administered to the subject is decreased if the expression level of two or more biomarkers in a tumor sample is decreased relative to the expression level of the two or more biomarkers in a normal tissue sample.

In a fourth aspect, a method is described for selecting a treatment for a subject having a tumor. The method comprises determining an expression level of two or more biomarkers in a tumor sample from the subject, wherein the two or more biomarkers are selected from the group consisting of CD44, MMP9, ALDH1A1, Vimentin, hyaluronan, beta-catenin, MFG-E8, and CD68. As above, the expression levels of the two or more biomarkers in the tumor sample are compared to the expression levels of the two or more biomarkers in a normal tissue sample. If the expression levels of the two or more biomarkers in the tumor sample are different from the expression levels in the normal tissue sample, for example, increased or decreased relative to the normal tissue level, a treatment is selected for the subject having the tumor.

In another aspect, the biomarkers described herein can also or further be used to determine the prognosis of disease during or after treatment. For example, the expression levels of the biomarkers before and after ionizing radiation therapy can be compared. In some embodiments, if the expression levels of the biomarkers after radiation therapy decrease, then the prognosis is favorable. In some embodiments, if the expression levels of the biomarkers after radiation therapy increase, then the prognosis is unfavorable.

In another aspect, the biomarkers described herein can also or further be used to assess the responsiveness of a patient to a cancer treatment. For example, the expression levels of the biomarkers before and after ionizing radiation therapy can be compared. The method comprises determining an expression level of two or more biomarkers in a tumor sample obtained from the subject, wherein the two or more biomarkers are selected from the group consisting of CD44, MMP9ALDH1A1, Vimentin, hyalurnan, beta-catenin, MFG-E8, and CD68. In some embodiments, if the expression levels of the biomarkers after radiation therapy decrease, then the patient has responded favorably. In some embodiments, if the expression levels of the biomarkers after radiation therapy increase, then the patient response was unfavorable. This information can be used to guide further therapy. Favorable treatments may be repeated or further increased. Unfavorable treatments can be modified or dropped.

In another aspect, a kit is provided. The kit comprises reagents capable of detecting expression of the biomarkers described herein. In some embodiments, the kit comprises reagents capable of detecting nucleic acid (e.g., RNA) expression of the biomarkers. For example, the kit can comprise oligonucleotide primers that are capable amplifying a nucleic acid expressed by the biomarker genes described herein. In some embodiments, the kit further comprises an oligonucleotide probe that hybridizes to a biomarker nucleic acid or an amplified biomarker nucleic acid, or a complement thereof. Methods of amplifying and detecting nucleic acids are welt known in the art, and can comprise PCR, RT-PCR real-time PCR, and quantitative real-time PCR, Northern analysis, sequencing of expressed nucleic acids, and hybridization of expressed and/or amplified nucleic acids to microarrays. In some embodiments, the kit comprises reagents that are capable of detecting proteins expression by the biomarkers described herein. In some embodiments, the reagents are antibodies that specifically bind to biomarker proteins. Methods of detecting protein expression are well known in the art, and include immunoassays, ELISA, Western analysis, and proteomic techniques.

In some embodiments of any of the above aspects and embodiments, the differences in the expression levels of each of the biomarkers in the tumor sample are increased or decreased by at least 10%, 20%, 30%, 40%, 50%, 60%, 70%, 80%, 90% or more compared to the expression level in normal tissue. In some embodiments, the expression levels of each of the biomarkers in the tumor sample are increased or decreased by at least 1-fold, 2-fold, 3-fold, 4-fold, 5-fold, 6-fold, 7-fold, 8-fold, 9-fold, 10 fold or more relative to the expression level in normal tissue.

In some embodiments, the average and/or ranked expression level of all the bioraarkers in the tumor sample is increased or decreased relative to the expression level in normal tissue. Thus, in some embodiments, the average and/orranked expression level of all the biomarkers in the tumor sample is increased or decreased by at least 10%, 20%, 30%, 40%, 50%, 60%, 70%, 80%, 90% or more compared to the expression level in normal tissue. In some embodiments, the expression levels in normal tissue are normalized to a control or baseline level. It will be understood that the expression level can also he compared to the expression level in the tumor sample before, after or during a treatment, course of treatment, or treatment plan. Thus, in some embodiments, the expression levels of each of the biomarkers in the tumor sample are increased or decreased by at least 10%, 20%, 30%, 40%, 50%, 60%, 70%, 80%, 90% or more compared to the expression level in the tumor sample before, during or after treatment.

Further, with regard to any of the above aspects and embodiments, the two or more biomarkers can comprise both CD44 and MMP9; both ALDH1A1 and Vimentin, both hyaluman and beta-catenin; both CD44 and ALDH1A1; both Vimentin and beta-catenin; both CD44 and hyalurnan; both CD44 and beta-catenin; both CD44 and MFG-E8 or both CD44 and CD68; both MMP9 and hyaluman; both MMP9 and beta-catenin; both MMP9 and MFG-E8, or both MMP9 and CD68 both ALDH1A1 and hyalurnan; both ALDH1A1 and beta-catenin; both ALDH1A1 and MFG-E8, or both ALDH 1A1 and CD68; both Vimentin and MFG-E8; both hyaluman and MFG-E8; both beta-catenin and MFG-E8, or both CD68 and MFG-E8.

Further, with regard to any of the above aspects and embodiments, the two or more biomarkers can comprise or consist of any combination of the biomarkers, for example any combination of three or more biomarkers, any combination of four or more biomarkers, any combination of five or more biomarkers, any combination of six or more biomarkers, and any combination of seven or more biomarkers. In one embodiment., the combination of biomarkers comprises or consists of CD44, MFG-E8, and CD68.

In another aspect, the expression level of at least one, two, three, four or more of the biomarkers described herein is determined.

In some embodiments, the treatment or selected treatment comprises administering ionizing radiation to the tumor. Thus, in some embodiments, the selected treatment comprises increasing the effective dose of ionizing radiation if the expression level of the two or more biomarkers is increased compared to the expression level in a normal tissue sample. In some embodiments, the selected treatment comprises decreasing the effective dose of ionizing radiation if the expression level of the two or more biomarkers is decreased compared to the expression level in a normal tissue sample. Exemplary radiotherapy treatments are further described herein. In all of the methods described herein, the treatment can further comprise contacting the tumor with a radiosensitizer. A radiosensitizer is any substance that makes tumor cells easier to kill with radiation therapy. Exemplary radiosensitizers include hypoxia radiosensitizers still as misonidazole, metronidazole, and trans-sodium crocetinate. Exemplary radiosensitizers also include DNA damage response inhibitors such as Poly (ADP) ribose polymerase (PARP) inhibitors. In all of the methods described herein, the treatment can further comprise contacting the tumor and/or the tumor environment with an immune modulator. Exemplary immune modulators include agents (antibodies or small molecules) involved in priming and activation of the immune systems, and include agents targeting CTLA4, B7 (B7-1 or B7-2), PD-L1/PD-L2, or PD-1, or agents targeting the binding interactions between CTLA4 and B7-1/B7-2, or PD-1 and PD-L1/PD-L2. Agents targeting CTLA4, B7 (B7-1or B7-2), PD-L1/PD-L2, and PD-1 include antibodies that specifically bind these molecules, such as monoclonal antibodies. In some embodiments, the agent is an antibody that specifically binds to LAG 3, TIM1, TIM3, MFG-E8, IL-10, or Phosphatidylserine.

Small molecule immune modulators include drugs that enhance or inhibit an immune response, for example, an immune response against a tumor cell. Exemplary small molecule immune modulators include inhibitors of the enzyme Indolamine 2,3-dioxygenase, and inhibitors of alpha-v-beta-3 integrin and alpha-v-beta-5 integrin In some embodiments, the treatment further comprises administering a compound that inhibits TGF-beta signaling to the subject. Suitable compounds are described in more detail below.

The biomarkers used in the method will now be described.

A. Biomarkers

The biomarkers described herein correlate with TGF-β expression, and can be used to stratify patients to receive individualized, tailored radiotherapy. The biomarker signature can also be used to monitor the efficacy of TGF-β inhibitors in patients. The biomarker signature is associated with but not limited to the correlation with TGF-β expression. The expression of the biomarkers is associated with radioresistance, aggressiveness and poor prognosis. The marker set includes, but is not limited to, CD44, MMP9, ALDH1A1, Vimentin, hyaluronan, β-catenin MFG-E8, and CD68.

MMP9: A clear correlation can be shown between MMP9, EMT and TGF-β. MMP9 regulates TGF-β and TGF-β regulates MMP9 in multiple settings. MMP9 is localized in the extracellular matrix and tumor stroma, within infiltrated immune cells and in tumor cells. The different cellular locations of MMP9 appear to be correlated with different biological outcomes (more/less aggressive tumor, survival etc).

Vimentin (VIM): Vimentin is upregulated when TGE-β induces EMT in a variety of cell types, including lung. Vimentin is an intermediate filament protein that characterizes mesenchymal cells as opposed to epithelial cells.

Hyaluronan (HA): Hyaluronan is an abundant glycosaminoglycan component of the extracellular matrix. It is induced by TGF-β, increases MMP9 secretion (likely via CD44), promotes EMT/migration/metastasis, and contributes to chemoresistance and poor prognosis. These findings have been substantiated in a variety of tumor types, including NSCLC. An important receptor for HA is CD44 along with others. The HA-CD44 interaction promotes HER2 signalling and increases Src kinase activity. HA is detected by staining the tissues with a commercially available antibody against Hyaluronic acid, for example, an antibody available from Abeam.

ALDH1A1: Aldehyde dehydrogenase is a detoxifying enzyme known for its role in the oxidation of intracellular aldehydes, which play a role in stem cell differentiation. It is highly expressed in tumorigenic cell populations of various cancers and elevated protein expression has been shown in putative lung stem cell niches during malignant transformation. Expression of ALDH1A is positively correlated with stage and grade of lung tumors and related to poor prognosis in patients with early stage lung cancer.

MFG-E8: MFG-E8 is a macrophage-produced protein that promotes engulfment and clearance of apoptotic cells in tumors. Antibodies neutralizing MFG-E8 function have been shown in experimental models to enhance radiation and chemotherapy. It is likely then, that the levels of MFG-E8 in tumor specimens may have predictive value for efficacy of radiotherapy.

CD68: CD68 is a 110-kD transmembrane glycoprotein that is highly expressed by human monocytes and tissue macrophages. It is a member of the lysosomal/endosomal-associated membrane glycoprotein (LAMP) family. The protein primarily localizes to lysosomes and endosomes with a smaller fraction circulating to the cell surface. It is a type I integral membrane protein with a heavily glycosylated extracellular domain and binds to tissue- and organ-specific lectins or selectins. The protein is also a member of the scavenger receptor family. Scavenger receptors typically function to clear cellular debris, promote phagocytosis, and mediate the recruitment and activation of macrophages (See Entrez listing NCBI).

CD68 is expressed broadly on macrophages including both M1 and M2 subsets. Numerous studies have suggested that macrophages present in the tumor micro-environment can impact growth of tumor cells and some clinical studies have suggested that the macrophage content and location in the tumor and its micro-environment is predictive of clinical outcome in certain cancer patients.

M1 macrophages are referred to as pro-inflammatory macrophages and have the ability to activate type 1 T helper cells (Th1) and to promote an anti-tumor response. In contrast, M2 macrophages activate type 2 T helper cells (Th2) and promote an anti-inflammatory, tissue remodeling response and do not lead to an anti-tumor action. As CD68 is expressed on both M1 and M2 macrophages, its presence cannot, a priori, be used to predict anti-tumor responses or clinical outcome. Thus, the present application describes that CD68 is useful as a biomarker determined in a clinical setting.

Nuclear β-catenin: β-catenin is found associated with E-cadherin at the cell membrane and also in the nucleus, where it accumulates in tumor cells, stem cells or cells undergoing EMT.

The GenBank Accession Nos. for the biomarkers described herein are provided in the Table below.

TABLE 1

| Biomarker Name | Abbreviation | GenBank Accession # (protein) | GenBank Accession # (nucleotide) |
| --- | --- | --- | --- |
| Hyaluronate receptor | CD44 | NP_000601 (SEQ ID NO: 1) | NM_000610 (SEQ ID NO: 2) |

TABLE 1-continued

| Biomarker Name | Abbreviation | GenBank Accession # (protein) | GenBank Accession # (nucleotide) |
| --- | --- | --- | --- |
| Matrix metalloproteinase 9 | MMP9 | CAC07541 (SEQ ID NO: 3) | AX011001 (SEQ ID NO: 4) |
| Aldehyde dehydrogenase 1A1 | ALDH1A1 | AAP88039 (SEQ ID NO: 5) | AY338497 (SEQ ID NO:6) |
| Vimentin | VIM | NP_003371 (SEQ ID NO: 7) | NM_003380 (SEQ ID NO:8) |
| hyaluronan | HA | Not applicable | |
| β-catenin | Beta_Cat | NP_001091680 (SEQ ID N0: 9) | NM_001098210 (SEQ ID NO: 10) |
| Milk fat globule-EGF factor 8 protein | MFG-E8 | NP_005919 (SEQ ID NO: 11) | NM_005928 (SEQ ID NO: 12) |
| CD68 | CD68 | NP_001242 (SEQ ID NO: 13) | NM_001251 (SEQ ID NO: 14) |

When the biomarkers described herein are referred to by name, it is understood that this includes molecules with similar functions and similar amino acid sequences. Thus, the protein biomarkers described herein include the prototype human protein, as well as homologs and polymorphic variations thereof. For example, the name "CD44 protein" includes the prototype protein (e.g. SEQ ID NO:1), as well as homologs from other species and polymorphic variations thereof. Proteins such as CD44 and CD68 are defined as having similar functions if they have substantially the same biological activity or functional capacity as the wild type protein (e.g., at least 80% of either). Proteins such as CD44 and CD68 are defined as having similar amino acid sequences if they have at least 80%, 85%, 90%, 95%, 96%, 97%, 98%, or 99% sequence identity to the prototype protein. The sequence identity of a protein is determined using the BLASTP program with the defaults wordlength of 3, an expectation (E) of 10, and the BLOSUM62 scoring matrix (see Henikoff and Henikoff, Proc. Natl. Acad. Sci. USA 89:10915-10919. 1992).

A conventional test to determine if a protein homolog or polymorphic variant is inclusive of a protein biomarker described herein is by specific binding to polyclonal antibodies generated against the prototype protein. For example, a. CD44 protein includes proteins that bind to polyclonal antibodies generated against the protein of SEQ ID NO:1, and an CD68 protein includes proteins that bind to polyclonal antibodies generated against the prototype protein of SEQ NO:13.

Regarding polyclonal antibodies that specifically bind to a protein biomarker described herein, the test protein will bind under designated immunoassay conditions to the specified antibodies at least two times the background, and the specified antibodies do not substantially bind in a significant amount to other proteins present in the sample. For example, polyclonal antibodies raised to CD44, encoded in SEQ ID NO:1, splice variants, or portions thereof, can be selected to obtain only those polyclonal antibodies that are specifically immunoreactive with CD44 and not with other proteins, except for polymorphic variants of CD44. This selection may be achieved by subtracting out antibodies that cross-react with other members of the protein family, as appropriate. A variety of immunoassay formats may be used to select antibodies specifically immunoreactive with a particular protein. For example, solid-phase ELISA immunoassays are routinely used to select antibodies specifically immunoreactive with a protein (see. e.g., Harlow & Lane, Antibodies, A Laboratory Manual (1988) for a description of immunoassay formats and conditions that can be used to determine specific immunoreactivity). Typically, a specific or selective reaction will be at least twice background signal or noise and more typically more than 10 to 100 times background.

In some embodiments, the method comprises determining the expression level of two or more biomarkers in a tumor sample from the subject. In some embodiments, the biomarker is selected from the group consisting of CD44, MMP9, ALDH1A1, Vimentin, hyaluronan, beta-catenin, MFG-E8, and/or CD68. In some embodiments, the expression level of two, three, four, five, six, seven, or eight of the biomarkers is determined. In some embodiments, the expression level of each of the biomarkers is determined. In some embodiments, the expression level of at least one additional biomarker is determined, wherein the additional biomarker is not in the group consisting of CD44, MMP9, ALDH1A1 Vimentin, hyaluronan, beta-catenin, MFG-E8, and CD68. In some embodiments, the additional biomarker is TGF-β.

In some embodiments, the biomarker signature group consists of CD44, MMP9, ALDH1A1, Vimentin, hyaluronan, beta-catenin, MFG-E8, and CD68, in some embodiments, the biomarker signature group consists essentially of CD44, MMP9, ALDH1A1, Vimentin, hyaluronan, beta-catenin, MFG-E8, and CD68. In some embodiments, the biomarker signature group comprises CD44, MMP9, ALDH1A1, Vimentin, hyaluronan, beta-catenin, MFG-E8, and CD68.

It will be understood that the expression levels of each of the biomarkers in the tumor sample can increase or decrease relative to the expression level of the biomarker in a normal or control tissue sample. For example, the expression level of one biomarker can increase in the tumor sample compared to the expression level in a normal tissue, whereas the expression level of a second biomarker can decrease in the tumor sample compared to the expression level in a normal tissue. The expression level can also be based on the average, combination or sum of the all the biomarker expression levels in the tumor sample. For example, the expression level of each biomarker in the tumor sample can be ranked or weighted to produce a ranked value that is higher or lower than the normal tissue value which can be a normalized value, for example, set to 1).

In some embodiments, biomarker expression is determined in a biological sample from the subject having a tumor. In some embodiments, the biological sample is a tumor sample. The tumor sample can be a biopsy comprising tumor cells from the tumor. In some embodiments, the biological sample comprises a bodily fluid, such as but not limited to blood, serum, plasma, or urine, and/or cells or tissues from the subject. In some embodiments, the biological sample is a formalin-fixed and paraffin embedded tissue or tumor sample. In some embodiments, the biological sample is a frozen tissue or tumor sample. Thus, in some embodiments, one or more steps of the methods described herein are carried out in vivo. For example, in some embodiments, biomarker expression is determined in vitro.

In some embodiments, the normal tissue sample comprises non-tumor cells from the same tissue type as the tumor. In some embodiments, the normal tissue sample is obtained from the same subject diagnosed with the tumor. A normal tissue sample can also be a control sample of the same tissue-type from a different subject. The expression level of the normal tissue sample can also be an average or mean value obtained from a population of normal tissue samples.

The level of expression of the biomarkers described herein can be determined using any method known in the art. For example, the level of expression can be determined by detecting the expression of a nucleic acid (e.g., RNA or mRNA) or protein encoded by a biomarker gene.

Exemplary methods for detecting expression levels of nucleic acids include without limitation Northern analysis, polymerase chain reaction (PCR), reverse transcription PCR (RT-PCR), real-time PCR, quantitative real-time PCR, and DNA microarrays.

Exemplary methods for detecting expression levels of proteins (e.g., polypeptides) include without limitation immunohistochemistry, ELISA, Western analysis, HPLC, and proteomics assays. In some embodiments, the protein expression level is determined by immunohistochemistry using the Allred method to assign a score (see, e.g., Allred, D. C., Connection 9:4-5, 2005, which is incorporated by reference herein). For example, formatin-fixed, paraffin embedded tissues are contacted with an antibody that specifically binds a biomarker described herein. The bound antibody is detected with a detectable label or secondary antibody coupled with a detectable label, such as a colorimetric label (e.g., an enzymatic substrate produce by HRP or AP). The antibody positive signal is scored by estimating the proportion of positive tumor cells and their average staining intensity. Both the proportion and intensity scores are combined into a total score that weighs both factors.

In some embodiments, the protein expression level is determined by digital pathology. Digital pathology methods include scanning images of tissues on a solid support, such as a glass slide. The glass slides are scanned into whole slide images using a scanning device. The scanned images are typically stored in an information management system for archival and retrieval. Image analysis tools can be used to obtain objective quantitative measurements from the digital slides. For example, the area and intensity of immunohistochemical staining can be analyzed using the appropriate image analysis tools. Digital pathology systems can include scanners, analytics (visualization software, information management systems and image analysis platforms), storage and communication (sharing services, software). Digital pathology systems are available from numerous commercial suppliers, for example. Aperio Technologies, Inc. (a subsidiary of Leica Microsystems GmbH), and Ventana Medical Systems, Inc. (now part of Roche). Expression levels can be quantified by commercial service providers, including Flagship Biosciences (CO), Pathology, Inc. (CA), Quest Diagnostics (NJ), and Premier Laboratory LLC (CO).

B. Treatments

The expression levels of the biomarkers can be used to determine or select a course of treatment in a subject diagnosed with a tumor. For example, in some embodiments, the treatment comprises administering ionizing radiation to the tumor in the subject. The ionizing radiation can also be administered to the entire subject or a portion thereof, especially if the tumor is dispersed or mobile. In some embodiments, the treatment further comprises contacting the tumor with a radiosensitizer. In some embodiments, the treatment further comprises administering a compound or biologic drug, such as an antibody, that inhibits TGF-beta signaling to the subject. Thus, in some embodiments, the treatment comprises administering a standard radiation treatment protocol in combination with a TGF-beta inhibitor.

The course of treatment can be selected based on the expression levels of the biomarkers. For example, the expression levels can be used to determine if radiation therapy is appropriate for the subject (i.e., for making a go/no go decision on radiotherapy). Further, if the expression levels of the biomarkers are increased relative to a normal or control value, then the effective radiation dose to the tumor can be increased, and/or the fractionation schedule modified accordingly. The radiation dose to the blood vessels feeding the tumor can also be increased.

In some embodiments, if the expression levels of the biomarkers are increased relative to a normal or control value, then the treatment can comprise administering ionizing radiation to the tumor. In some embodiments, if the expression levels of the biomarkers are decreased relative to a normal or control value, then the treatment can comprise decreasing the amount of ionizing radiation administered to the tumor.

The treatment can also comprise modifying an existing course of treatment. For example, in some embodiments, the existing course of treatment is modified to increase the effective dose of the ionizing radiation administered to the tumor. In some embodiments, the effective dose of ionizing radiation is increased by increasing the amount of ionizing radiation administered to the tumor and/or contacting the tumor with a radiosensitizer. In some embodiments, the existing course of treatment is modified to decrease the effective dose of the ionizing radiation administered to the tumor. In some embodiments, the treatment comprises modifying a standard radiation treatment protocol in combination with administering a TGF-beta inhibitor.

In some embodiments, the effective dose of ionizing radiation administered to the tumor is increased if the level of one or more biomarkers described herein is elevated in the tumor environment. For example, the effective dose of ionizing radiation is increased as compared to the standard of care for a subject that does not have elevated levels of the biomarker(s) in the tumor environment. This applies to subjects who are currently not undergoing radiation therapy as well as modifying an existing course of treatment for subjects undergoing radiation therapy. Thus, the effective dose of ionizing radiation can be increased from the current effective dose if the subject is already undergoing radiation therapy for a tumor. The radiation therapy can be modified to reduce the constraints on neighboring healthy tissue. For example, if the biomarker level in the tumor environment indicates more aggressive radiation therapy is required, the treatment plan can be modified so that the constraints on the border between healthy tissue and tumor tissue are decreased. This would result in a trade-off between damaging some healthy tissue in order to kill more of the tumor tissue.

In some embodiments, the treatment comprises a combination of radiation therapy and an anti-cancer agent (including a radiosensitizer). In some embodiments, the effective dose of ionizing radiation administered to the tumor is not changed (e.g., relative to the standard of care or relative to an existing course of treatment) when an anti-cancer agent is administered to the subject. For example, in some embodiments, the subject is administered an effective dose of ionizing radiation that is the same or similar to that administered to a subject that does not have elevated levels of one or more biomarkers described herein in the tumor environment, and the subject is further administered an anti-cancer agent. In some embodiments, the effective dose of ionizing radiation administered to the tumor is based on the standard of care for a subject that does not have elevated levels of the biomarker(s) in the tumor environment, and the subject is further administered an anti-cancer agent. In some embodiments involving an existing course of treatment, the effective dose of ionizing radiation is maintained at the current effective dose, and an anti-cancer agent is administered to the subject in combination with the ionizing radiation if the level of one or more biomarkers described herein is elevated in the tumor environment.

In some embodiments, the subject is administered an increased effective dose of ionizing radiation if the expression of CD44 or CD68 is elevated in the tumor environment. In some embodiments, the subject is administered an effective dose of ionizing radiation that is the same or similar to the effective dose administered to a subject that does not have elevated levels of CD44 or CD68 in the tumor environment (e.g., according to the current standard of care), in combination with a pharmaceutically effective amount of an anti-cancer agent, if the expression of CD44 or CD68 is elevated in the tumor environment. In some embodiments, the subject is administered an increased effective dose of ionizing radiation if the level of CD44 is increased and the level of MFG-E8 is decreased in the tumor environment. In some embodiments, the subject is administered an effective dose of ionizing radiation that is the same or similar to the effective dose administered to a subject that does not have increased levels of CD44 and decreased levels of MFG-E8 in the tumor environment (e.g., according to the current standard of care), in combination with a pharmaceutically effective amount of an anti-cancer agent, if the level of CD44 is increased and the level of MFG-E8 is decreased in the tumor environment. The above embodiments apply to subjects who are currently not undergoing radiation therapy as well as modifying an existing course of treatment for subjects undergoing radiation therapy.

In some embodiments, the treatment plan is developed and/or modified based on the expression levels of the biomarkers described herein.

The course of treatment can also be selected by using an algorithm that determines the expression level of the biomarkers in the tumor sample relative to the level in the normal sample. The algorithm can be a linear regression algorithm that includes the biomarker expression levels and coefficients (i.e., weights) for combining the expression levels. In some embodiments, the algorithm comprises a least squares fit to calculate the coefficients. If the algorithm determines that the expression level of the biomarkers in the tumor sample is increased or decreased relative to the normal sample, then the appropriate course of treatment can be assigned. In some embodiments, the algorithm is a nonparametric regression tree. In some embodiments, standard statistical methods were used to analyze the data to determine which biomarkers were most predictive of clinical survival or local tumor control failure.

In some embodiments, the method described herein is a computer implemented method. In some embodiments, the computer implemented method comprises a linear regression model that assigns a ranked or weighted value to the expression levels of the biomarkers described herein. In some embodiments, the disclosure provides a computer-readable medium, the medium providing instructions to cause a computer to perform a method described herein. For example, the medium can provide instructions to cause a computer to assign a ranked or weighted value to the expression levels of the biomarkers described herein.

C. Therapeutic Radiation Doses

The expression levels of the tumor biomarkers described herein can be used to optimize treatment of patients with radiotherapy. For example, the therapeutic dose of the radiation administered to the tumor or subject can be adjusted based on the expression levels of the biomarkers. As is well known in the art, the effective dose of ionizing radiation varies with the type of tumor and stage of cancer that needs to be treated. The effective dose can also vary based on other treatment modalities being administered to the patient, for example chemotherapeutic treatments and surgical treatments, and whether the radiation is administered pre- or post-surgery. In general, a curative therapeutic dose for a solid epithelial tumor ranges from about 60 to 80 gray (Gy), whereas a curative dose for a lymphoma is about 20 to 40 Gy. In general, preventative doses can be 45-60 Gy.

As is well known in the art, the therapeutic dose can be delivered in fractions. Fractionation refers to spreading out the total dose of radiation over time, for example, over days, weeks or months. The dose delivered in each fraction can be about 1.5-2 Gy per day. The treatment plan can include a fraction treatment one or more times per day, every other day, weekly, etc. depending on the treatment needs of each patient. For example, a hypofractionation schedule comprises dividing the total dose into several relatively large doses, and administering the doses at least one day apart. Exemplary hypofraction doses are 3 Gy to 20 Gy per fraction. An exemplary fractionation schedule that can be used to treat lung cancer is Continuous Hyperfractionated Accelerated Radiation therapy (CHART), which consists of three small fractions per day.

The biomarkers described herein are useful in developing and modifying treatment plans for patients diagnosed with a tumor or cancer. The treatment plan can include visualizing or measuring the tumor volume that needs to be irradiated, the optimal or effective dose of radiation administered to the tumor, and the maximum dose to prevent damage to nearby healthy tissue or organs at risk. Algorithms can used in treatment planning, and include dose calculation algorithms based on the particular radiotherapy technique parameters employed, e.g., gantry angle, MLC leaf positions, etc., and search algorithms which use various techniques to adjust system parameters between dose calculations to optimize the effectiveness of the treatment. Exemplary dose calculation algorithms include various Monte Carlo ("MC") techniques and pencil beam convolution ("PBC"). Exemplary search algorithms include various simulated annealing ("SA") techniques, algebraic inverse treatment planning ("AITP"), and simultaneous iterative inverse treatment planning ("SIITP"). Such techniques, and others, are well known in the art, and are included within the scope of this disclosure.

Treatment planning algorithms may be implemented as part of an integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present invention includes such an integrated software program. Methods for optimizing treatment plans are described in U.S. Pat. No. 7,801,270, which is incorporated by reference herein.

In some embodiments, the biomarkers described herein can be used to monitor the progress of tumor control after radiation therapy. For example, the expression levels of the biomarkers before and after ionizing radiation therapy can be compared. In some embodiments, if the expression levels of biomarkers increase after radiotherapy, this suggests that the tumor is continuing to grow in size. Thus, the radiation treatment can be modified based on monitoring tumor growth using the biomarkers described herein.

The biomarkers described herein can be used with any radiation therapy technique known in the art. Radiation therapy techniques include external-beam radiotherapy ("EBRT") and Intensity Modulated Radiotherapy ("IMRT"), which can be administered by a radiotherapy system, such as a linear accelerator, equipped with a multileaf collimator ("MLC"). The use of multileaf collimators and IMRT allows the patient to be treated from multiple angles while varying the shape and dose of the radiation beam, thereby avoiding excess irradiation of nearby healthy tissue. Other exemplary radiation therapy techniques include stereotactic body radiotherapy (SBRT), volumetric modulated arc therapy, three-dimensional conformal radiotherapy ("3D conformal" or "3DCRT"), image-guided radiotherapy (IGRT). The radiation therapy techniques can also include Adaptive radiotherapy (ART), a form of IGRT that can revise the treatment during the course of radiotherapy in order to optimize the dose distribution depending on patient anatomy changes, and organ and tumour shape. Another radiation therapy technique is brachytherapy. In brachytherapy, a radioactive source is implanted within the body of the subject, such that the radioactive source is near the tumor. As used herein, the term radiotherapy should be broadly construed and is intended to include various techniques used to irradiate a patient, including use of photons (such as high energy x-rays and gamma rays), particles (such as electron and proton beams), and radiosurgical techniques. Further, any method of providing conformal radiation to a target volume is intended to be within the scope of the present disclosure.

D. Chemotherapeutic Agents

In some embodiments, the radiation therapy is administered in combination with one or more chemotherapeutic agents (i.e., anti-cancer agents). The chemotherapeutic agents include radiosensitizers, anti-tumor or anti-cancer agents, and/or inhibitors of TGF-beta signaling. In some embodiments, the radiation therapy is administered in combination with an immune system modulator.

1. Radiosensitizers

In some embodiments, the chemotherapeutic agent is a radiosensitizer. Exemplary radiosensitizers include hypoxia radiosensitizers such as misonidazole, metronidazole, and trans-sodium crocetinate, a compound that helps to increase the diffusion of oxygen into hypoxic tumor tissue. The radiosensitizer can also be a DNA damage response inhibitor interfering with base excision repair (BER), nucleotide excision repair (NER), mismatch repair (MMR), recombinational repair comprising homologous recombination (HR) and non-homologous end-joining (NHEJ), and direct repair mechanisms. SSB repair mechanisms include BER, NER, or MMR pathways whilst DSB repair mechanisms consist of HR and NHEJ pathways. Radiation causes DNA breaks that if not repaired are lethal. Single strand breaks are repaired through a combination of BER, NER and MMR mechanisms using the intact DNA strand as a template. The predominant pathway of SSB repair is the BER utilizing a family of related enzymes termed poly-(ADP-ribose) polymerases (PARP). Thus, the radiosensitizer can include DNA damage response inhibitions such as Poly (ADP) ribose polymerase (PARP) inhibitors.

2. Anti-tumor Agents

In some embodiments, the chemotherapeutic agent is an anti-cancer agent. Examples of anti-cancer agents include hypoxic cytotoxins, such as tirapazamine In some embodiments, the anti-cancer agent is a drug that is currently approved for treating cancer or tumors, in some embodiments, the anti-cancer agent is approved for treating lung cancer, for example, Cisplatin, Taxol, Paclitaxal, Abitrexate, Bevacizumab, Folex, Gemcitabine, or Iressa. In some embodiments, the anti-cancer agent targets a fusion protein, and includes agents such as Crizotinib.

3. TGF-β Inhibitors

There is substantial evidence that IGF-β plays a crucial role in the response to ionizing radiation. TGF-β is a pleiotropic cytokine that is important in normal tissue homeostatis, regulates inflammation and immune responses, and suppresses epithelial proliferation. IGF-β is activated in irradiated tissues, presumably because the latent TGF-β complex has a specific—redox—sensitive conformation activated by reactive oxygen species, which are generated by radiation. There is significant evidence for activated IGF-β to contribute to metastasis, to drive function-compromising fibrosis, to promote tumor cell proliferation, and to suppress immune surveillance. Thus, in some embodiments, the chemotherapeutic agent is a TGF-β inhibitor. There are four major classes of TGF-β inhibitors, including ligand traps (e.g. 1D11 or Fresolimumab), antisense oligonucleotides (e.g., Trabedersen), small molecule receptor kinase inhibitors (e.g., LY2109761 or LY2157299), and peptide aptamers (e.g. Trx-SARA). Any suitable TGF-β inhibitor known in the art can be used in the methods, and is considered within the scope of the methods described herein. TGF-beta inhibitors also include agents that inhibit the production of activated TGF-beta.

4. Immune Modulators

Examples of immune modulators include antibodies that bind molecules expressed on the surface of immune system cells, such as antigen presenting cells and T-cells immune modulators also include small molecules that inhibit or stimulate the immune system. One non-limiting example of a small molecule immune modulator is an inhibitor of the enzyme Indolamine 2,3-dioxygenase.

EXAMPLES

Example 1

This example describes the association between the biomarkers described herein and clinical outcomes (survival and local tumor control) for lung cancer patients treated with radiation.

Statistical Methods

In order to understand the characteristics of the population under investigation, descriptives of both demographics and biomarker levels (intensity, proportion, and total; abbreviated "Int," "Prop," and "Tot" throughout) were first examined Biomarker levels were examined using Allred scoring system. The Allred scoring system allows for measurement of biomarker expression as monitored by immunohistochemistry. It takes into account the percentage/proportion of cells that stain by immunohistochemistry (on a scale of 0-5) and the intensity of that staining (on a scale of 0-3), leading to a possible total score of 8. Survival time was then modeled using cox proportional hazards models, defined as date of biopsy to date of death or last follow-up. Univariate models were examined first, followed by multivariate models to determine factors most predictive of survival. Multivariate models were built using stepwise regression, and were also further examined for possible effect modification. We also dichotomized each biomarker using two methods: 1) a cut point suggested by a nonparametric regression tree, where a cut point is found that "best" separates subjects by survival time and 2) by a visual examination of where clear separation in the distributions exist. Lastly, we examined how predictive biomarkers and clinical characteristics were of local tumor control failure using logistic regression models. Statistical significance was set to level 0.05 for all analyses.

Results

A total of 133 deceased lung cancer patients were included in the analysis. The median survival time among all patients was 1.5 years. The majority of patients were white males; most underwent curative radiation therapy, were diagnosed at stage III, and were current smokers (Table 2). The expression pattern of biomarkers varied greatly: ALDH1A1, CD68, HA, and VIM tended to have low values, while Beta_Cat, CD44, MFG_E8 and MMP_9 tended to have high values (See FIGS. 1-8).

TABLE 2

Descriptive Patient Characteristics (N = 133)

| Variable | Level | N (%) or N, Mean (SD), [Min, Max] |
|---|---|---|
| Gender | Female | 56 (42%) |
| | Male | 77 (58%) |
| Race | Black | 52 (40%) |
| | Non-Black | 80 (60%) |
| Radiation Therapy | Curative | 114 (86%) |
| | Curative/SBRT | 5 (4%) |
| | SBRT | 14 (10%) |
| Treatment Group | RT Alone | 42 (33%) |
| | Chemo RT | 86 (67%) |
| Local Tumor Control | Yes | 100 (75%) |
| | No | 33 (25%) |
| Stage at Diagnosis | I | 25 (20%) |
| | II | 18 (14%) |
| | III | 77 (61%) |
| | IV | 6 (5%) |
| Smoking | current smoker | 73 (57%) |
| | not smoker | 2 (2%) |
| | past smoker | 51 (39%) |
| | unknown | 3 (2%) |
| Tumor Type | Adenocarcinoma | 23 (20%) |
| | Squamous | 95 (80%) |
| Age | | 133, 78 (11), [52, 98] |
| Median Household income | <$15,000 | 6 (5%) |
| | ≥$15,000-<$30,000 | 33 (27%) |
| | ≥$30,000-<$50,000 | 42 (34%) |
| | ≥$50,000-<$75,000 | 28 (23%) |
| | ≥$75,000 | 13 (11%) |

Univariate survival models indicated that the only patient characteristics exhibiting significant differences in risk were race, where blacks had nearly a 1.5 times greater risk of death than non-blacks (p-value=0.038, Table 3). Additionally, crude estimates of differences in survival by biomarker levels indicated that higher levels of CD68 were associated with a statistically significant higher risk of death. Namely, a one unit increase in CD68 Prop increased the risk of death by 49%, while a one unit increase in CD68 Tot increased the risk of death by 25% (p-value=0.008, p-value=0.02 for Prop and Tot, respectively). Further, a marginally significant protective effect was observed for MMP_9 (p-value=0.05, p-value=0.054 for Prop and Tot, respectively). Using the optimal cut point method for each biomarker based on regression trees, CD68 and VIM groups displayed association with survival, and there was some marginal significance of MFG_E8. Using cut points determined by visual examination, MFG_E8 groups were associated with survival. In these plots, CD68 (Prop and Tot) and VIM (Prop and Tot) both increased risk, while MFG_E8 decreased risk.

TABLE 3

Univariate Survival Estimates

| Parameter | Level | Hazard Ratio (HR) (95% CI) | Comparison p-value | Overall p-value |
|---|---|---|---|---|
| *Patient Characteristics* | | | | |
| Gender | Male vs. Female | 1.03 (0.72, 1.46) | | 0.88 |
| Race | Black vs. Non-Black | 1.47 (1.02, 2.1) | 0.038 | 0.038 |
| Smoking | not smoker vs. current smoker | 2 (0.48, 8.25) | 0.34 | 0.37 |
| | past smoker vs. current smoker | 1.12 (0.78, 1.61) | 0.54 | |
| | unknown vs. current smoker | 2.46 (0.76, 7.92) | 0.13 | |
| Stage at Diagnosis | II vs. I | 1.07 (0.58, 1.96) | 0.84 | 0.98 |
| | III vs. I | 0.98 (0.62, 1.55) | 0.93 | |
| | IV vs. I | 0.9 (0.37, 2.2) | 0.82 | |
| Stage II or III at Diagnosis | Yes vs. No | 1.16 (0.78, 1.74) | 0.46 | 0.46 |
| Tumor Type | Squamous vs. Adenocarcinoma | 1.15 (0.73, 1.82) | 0.54 | 0.54 |
| Treatment Group | chemo RT vs. RT Alone | 0.72 (0.49, 1.05) | 0.088 | 0.088 |
| Local Tumor Control | Yes vs. No | 1.06 (0.72, 1.58) | 0.76 | 0.76 |
| Radiation Therapy | Curative/SBRT vs. Curative | 0.55 (0.22, 1.36) | 0.19 | 0.20 |
| | SBRT vs. Curative | 1.39 (0.8, 2.44) | 0.25 | |
| Age | | 1 (0.99, 1.02) | | 0.56 |
| *Biomarkers* | | | | |
| ALDH1A1_Int | | 1 (0.78, 1.29) | | 1.00 |
| ALDH1A1_Prop | | 0.98 (0.85, 1.14) | | 0.82 |
| ALDH1A1_Tot | | 0.99 (0.9, 1.09) | | 0.90 |
| Beta_Cat_Int | | 0.84 (0.66, 1.09) | | 0.19 |
| Beta_Cat_Prop | | 0.95 (0.8, 1.13) | | 0.57 |
| Beta_Cat_Tot | | 0.95 (0.85, 1.06) | | 0.32 |
| CD44_Int | | 1.11 (0.9, 1.36) | | 0.33 |
| CD44_Prop | | 1.06 (0.93, 1.2) | | 0.38 |
| CD44_Tot | | 1.04 (0.96, 1.14) | | 0.32 |
| CD68_Int | | 1.33 (0.89, 1.99) | | 0.16 |
| CD68_Prop | | 1.49 (1.11, 1.99) | | 0.008 |
| CD68_Tot | | 1.25 (1.04, 1.51) | | 0.02 |
| HA_Int | | 0.94 (0.76, 1.17) | | 0.59 |
| HA_Prop | | 0.93 (0.83, 1.04) | | 0.20 |
| HA_Tot | | 0.96 (0.88, 1.04) | | 0.27 |
| MFG_E8_Int | | 0.92 (0.74, 1.14) | | 0.44 |
| MFG_E8_Prop | | 0.92 (0.83, 1.02) | | 0.10 |
| MFG_E8_Tot | | 0.95 (0.88, 1.02) | | 0.15 |
| MMP_9_Int | | 0.83 (0.62, 1.11) | | 0.21 |
| MMP_9_Prop | | 0.8 (0.64, 1) | | 0.05 |
| MMP_9_Tot | | 0.87 (0.76, 1) | | 0.054 |
| VIM_Int | | 1.02 (0.83, 1.25) | | 0.87 |
| VIM_Prop | | 1.02 (0.87, 1.19) | | 0.78 |
| VIM_Tot | | 1.01 (0.92, 1.11) | | 0.81 |

Table 4 displays the results of a final multivariate model built using stepwise regression. All patient characteristics and 24 biomarker measurements were eligible for model inclusion. The significance level required to both enter the model and be retained in the model was 0.05. This model selection procedure only retained CD68 Prop and race in the model, indicating that these two covariates are most predictive of survival outcomes, among all covariates considered.

TABLE 4

Final Survival Model

| Parameter | HR (95% CI) | p-value |
|---|---|---|
| CD68 Prop | 1.61 (1.19, 2.18) | 0.002 |
| black vs. non-black | 1.59 (1.05, 2.41) | 0.028 |

It should be noted that since correlation within a biomarker is high (comparing the three different measures of Int, Prop and Tot), it is unlikely that multiple measurement types of the same biomarker would be retained in the model, due to information redundancy.

Predictive Ability of Biomarkers for Local Tumor Control

Figure 9:
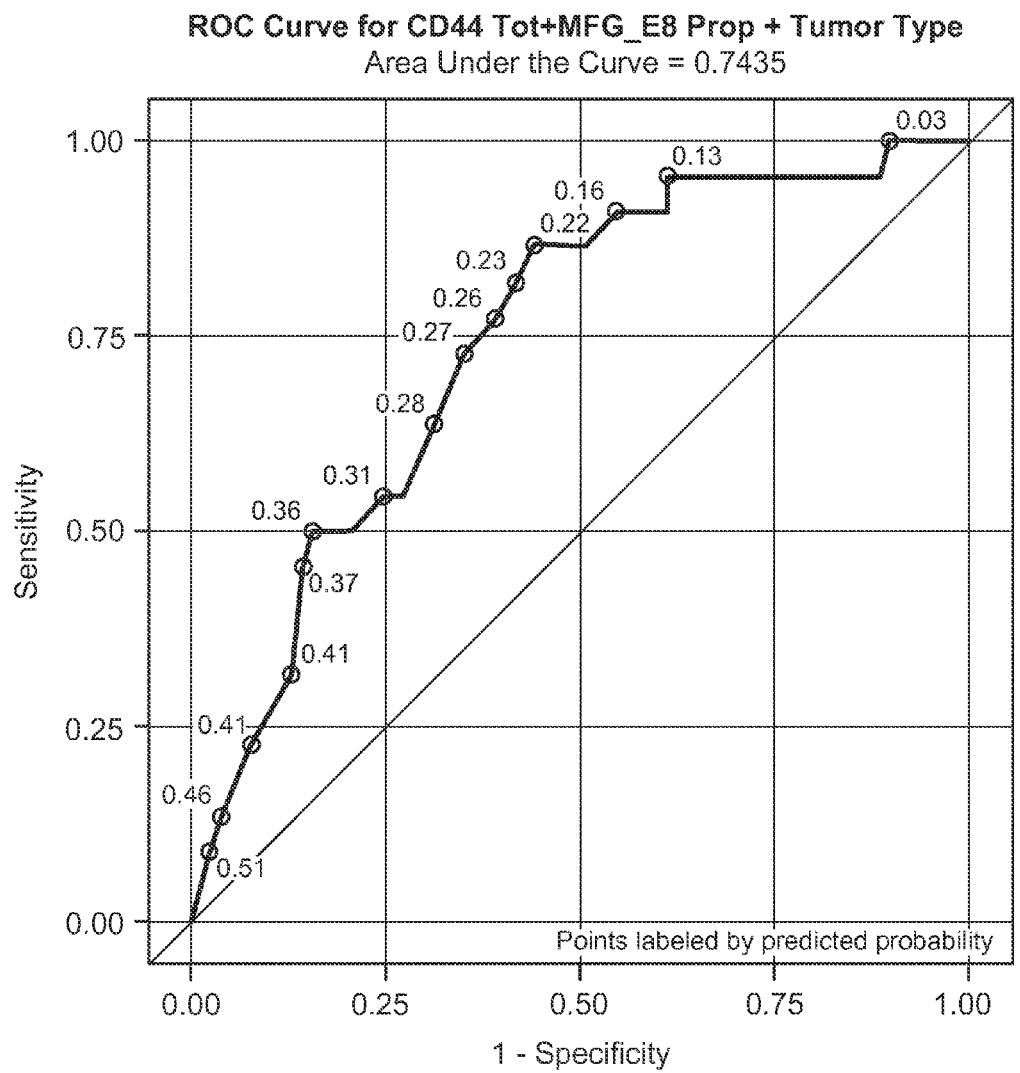
FIG. 9 shows the ROC curve for the variables CD44 (Tot), MFG_E8 (Prop) and tumor type from a multivariate model to predict local tumor control.

We also determined if biomarkers, along with clinical characteristics, were predictive of local tumor control failure. We use the Area Under the ROC (Receiver Operating Characteristics) Curve (AUC) as a measure of predictive ability, where the ROC curve is built from various probability cut points from a logistic regression model. An AUC of 0.5 indicates "no better than random chance" and an AUC of 1 indicates "perfect prediction". As seen in Table 5, Tumor Type, CD44, and MFG_E8 all had a significantly better than random chance prediction ability. CD44 and squamous tumors were risk factors for local tumor control failure, MFG_E8 had a protective effect. To find a more predictive model of local tumor control failure, we then determined which combination of these three factors resulted in the highest AUC. The variables CD44 (Tot), MFG_E8 (Prop) and tumor type combined resulted in an AUC of 0.74 (p-value<0.001. 95% CI=(0.63, 0.85)). The ROC curve from this multivariate model can be seen in FIG. 9.

TABLE 5

Predictive Ability of Biomarkers for Local Tumor Control Failure (Univariate)

| Parameter | Level | Odds Ratio OR (95% CI) | Comparison p-value | Overall p-value | Area Under the Curve AUC (95% CI) | p-value |
|---|---|---|---|---|---|---|
| *Patient Characteristics* | | | | | | |
| Gender | Male vs. Female | 1.16 (0.52, 2.59) | | 0.72 | 0.52 (0.42, 0.62) | 0.72 |
| Race | Black vs. Non-Black | 1.18 (0.53, 2.63) | | 0.68 | 0.52 (0.42, 0.62) | 0.69 |
| Age | | 0.98 (0.94, 1.01) | | 0.18 | 0.59 (0.47, 0.7) | 0.14 |
| Radiation Therapy | Curative/SBRT vs. Curative | 0.7 (0.08, 6.51) | 0.75 | 0.61 | 0.54 (0.47, 0.6) | 0.26 |
| | SBRT vs. Curative | 0.47 (0.1, 2.21) | 0.34 | | | |
| Treatment Group | chemo RT vs. RT Alone | 1.64 (0.67, 4.06) | | 0.28 | 0.55 (0.46, 0.64) | 0.26 |
| Stage II or III at Diagnosis | Yes vs. No | 1.07 (0.43, 2.68) | | 0.89 | 0.51 (0.42, 0.59) | 0.89 |
| Smoking* | | — | — | — | — | — |
| Tumor Type | Squamous vs. Adenocarcinoma | 4.39 (0.96, 19.98) | | 0.056 | 0.59 (0.52, 0.65) | 0.008 |
| Median Household Income* | | — | — | — | — | — |
| *Biomarkers* | | | | | | |
| ALDH1A1 Int | | 1.48 (0.88, 2.49) | | 0.14 | 0.57 (0.46, 0.67) | 0.21 |
| ALDH1A1 Prop | | 1.27 (0.94, 1.73) | | 0.12 | 0.57 (0.47, 0.67) | 0.18 |
| ALDH1A1 Tot | | 1.19 (0.97, 1.451 | | 0.09 | 0.57 (0.47, 0.68) | 0.18 |
| Beta_Cat Int | | 0.65 (0.36, 1.2) | | 0.17 | 0.57 (0.46, 0.69) | 0.20 |
| Beta_Cat Prop | | 0.85 (0.58, 1.26) | | 0.42 | 0.56 (0.45, 0.67) | 0.30 |
| Beta_Cat Tot | | 0.85 (0.66, 1.11) | | 0.24 | 0.59 (0.47, 0.71) | 0.13 |
| CD44 Int | | 1.94 (1.08, 3.51) | | 0.027 | 0.62 (0.52, 0.72) | 0.019 |
| CD44 Prop | | 1.7 (1.11, 2.6) | | 0.014 | 0.65 (0.55, 0.76) | 0.003 |
| CD44 Tot | | 1.44 (1.08, 1.92) | | 0.012 | 0.66 (0.55, 0.76) | 0.004 |
| CD68 Iot | | 1.93 (0.83, 4.49) | | 0.13 | 0.56 (0.47, 0.64) | 0.18 |
| CD68 Prop | | 1.16 (0.67, 2) | | 0.61 | 0.55 (0.47, 0.63) | 0.22 |
| CD68 Tot | | 1.16 (0.82, 1.66) | | 0.40 | 0.55 (0.47, 0.63) | 0.23 |
| HA Iot | | 1.03 (0.65, 1.62) | | 0.91 | 0.51 (0.4, 0.63) | 0.80 |
| HA Prop | | 0.96 (0.74, 1.26) | | 0.79 | 0.5 (0.39, 0.61) | 0.97 |
| HA Tot | | 0.99 (0.83, 1.18) | | 0.89 | 0.5 (0.39, 0.61) | 0.96 |
| MFG_E8 Int | | 0.73 (0.47, 1.14) | | 0.17 | 0.58 (0.47, 0.7) | 0.17 |
| MFG_E8 Prop | | 0.77 (0.62, 0.97) | | 0.029 | 0.64 (0.52, 0.75) | 0.019 |
| MFG_E8 Tot | | 0.85 (0.73, 1) | | 0.046 | 0,63 (0.52, 0,74) | 0.023 |
| MMP_9 int | | 1.39 (0.73, 2.67) | | 0.32 | 0.56 (0.46, 0.66) | 0.23 |
| MMP_9 Prop | | 1.26 (0.69, 2.3) | | 0.46 | 0.57 (0.5, 0.65) | 0.06 |
| MMP_9 Tot | | 1.2 (0.83, 1.73) | | 0.33 | 0.59 (0.49, 0.7) | 0.07 |
| VIM Int | | 1.15 (0.73, 1.81) | | 0.56 | 0.53 (0.43, 0.62) | 0.58 |
| VIM Prop | | 1.07 (0.76, 1.49) | | 0.71 | 0.52 (0.43, 0.61) | 0.65 |
| VIM Tot | | 1.05 (0.86, 1.28) | | 0.63 | 0.52 (0.43, 0.61) | 0.65 |

Figure 10:
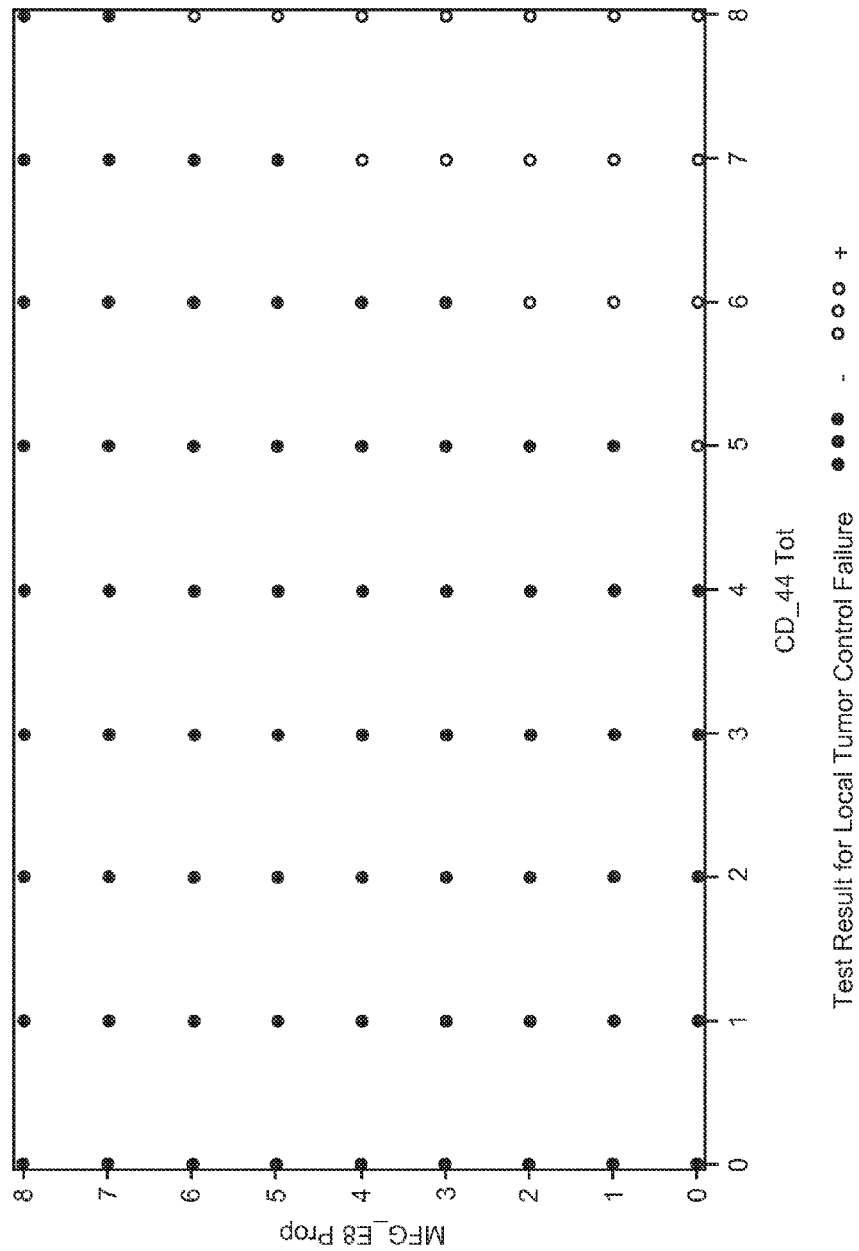
FIG. 10 shows the values of CD44 (Tot) and MFG_E8 (Prop) that correspond to a positive and negative test result for predicting local tumor control failure for squamous tumors, as described in the Examples.
Figure 11:
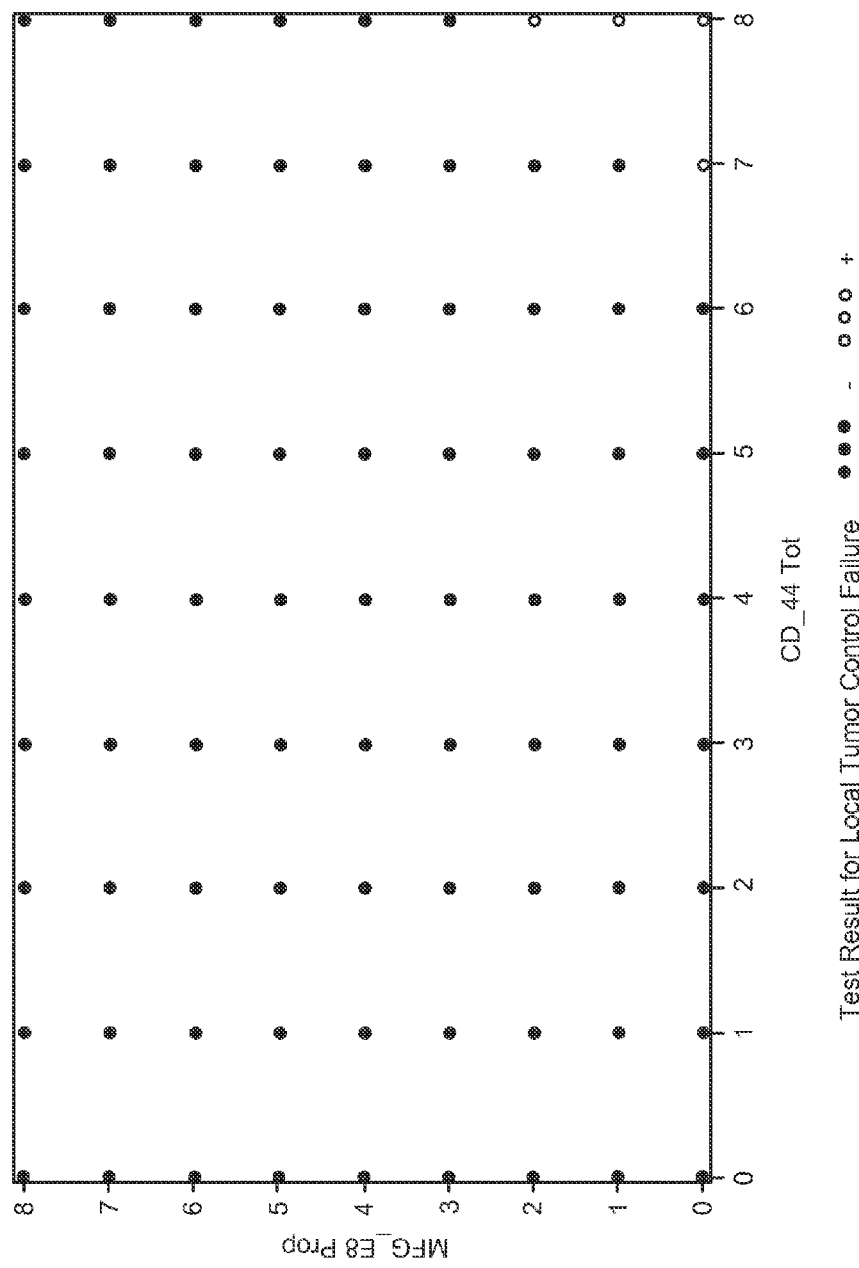
FIG. 11 shows the values of CD44 (Tot) and MFG_E8 (Prop) that correspond to a positive and negative test result for predicting local tumor control failure for adenocarcinoma tumors, as described in the Examples.

We then chose a probability cut point on this ROC curve that exhibited both high sensitivity and specificity, to act as a "test" for local tumor control failure. We required that both sensitivity and specificity be at least 0.5, and gave more importance to high sensitivity by up-weighting it. This resulted in a probability cut point of 21%, which corresponded to a sensitivity of 82% and a specificity of 55%. The values of CD44 Tot and MFG_E8 Prop that correspond to a positive and negative test using this probability cut point, for each tumor type, can be seen in FIGS. 10 and 11.

Subgroup Analyses for Stage II and III Patients

As a sensitivity analysis, univariate survival estimates for patient characteristics and biomarker levels were also recalculated among stage II and III patients only (results not shown). In this analysis, the covariate that achieved statistical significance was race (p-value=0.018).

This Example demonstrates that, among 133 deceased lung cancer patients, CD68 expression was associated with increased risk of death, while MMP_9 expression was associated with decreased risk of death. Patient characteristics most predictive of survival outcomes were CD68 and race. CD44, MFG_E8, and tumor type were predictive of local tumor control failure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A method for treating a tumor in a subject, the method comprising:
   i) contacting a tumor sample from the subject with antibodies that bind to biomarkers CD44 and CD68;
   ii) contacting a normal tissue sample with antibodies that bind to the biomarkers CD44 and CD68;
   iii) detecting increased expression of CD44 and CD68 in the tumor sample as compared to the normal tissue sample, and
   iv) administering an effective dose of ionizing radiation to the tumor and a TGF-beta inhibitor to the subject, thereby treating the tumor, wherein the TGF-beta inhibitor is an antibody or a small molecule.

2. The method of claim 1, wherein the dose of ionizing radiation is administered to the tumor by hypofractionation.

3. The method of claim 1, wherein the dose of ionizing radiation is administered to the tumor by hyperfractionation.

4. The method of claim 1, wherein the treatment further comprises administering an anti-cancer agent to the subject, wherein the anti-cancer agent is a chemotherapeutic agent, radiosensitizer, or immune modulator.

5. The method of claim 1, wherein the biomarker is a protein.

6. The method of claim 1, wherein the biomarker is detected by immunohistochemistry, ELISA, Western analysis, or digital pathology.

7. The method of claim 1, wherein the normal tissue sample comprises non-tumor cells from the same tissue type as the tumor.

8. The method of claim 1, further comprising determining the expression level of at least one additional biomarker from the tumor sample.

* * * * *

SEQUENCE LISTING

<160> NUMBER OF SEQ ID NOS: 14

<210> SEQ ID NO 1
<211> LENGTH: 742
<212> TYPE: PRT
<213> ORGANISM: Homo sapiens
<220> FEATURE:
<223> OTHER INFORMATION: CD44 antigen isoform 1 precursor, hematopoeitic
      cell E- and L-selectin ligand (HCELL), chondroitin sulfate
      proteoglycan 8 (CSPG8), GP90 lymphocyte homing/adhesion receptor
      (LHR), extracellular matrix receptor III (ECMR-III), Hermes
      antigen

<400> SEQUENCE: 1

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ser Ala His
        420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
        450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
                660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 2
<211> LENGTH: 5748
<212> TYPE: DNA
<213> ORGANISM: Homo sapiens
<220> FEATURE:
<223> OTHER INFORMATION: CD44 antigen transcript variant 1,
      hematopoeitic cell E- and L-selectin ligand (HCELL), chondroitin
      sulfate proteoglycan 8 (CSPG8), GP90 lymphocyte homing/adhesion
      receptor (LHR), extracellular matrix receptor III (ECMR-III),
      Hermes antigen

<400> SEQUENCE: 2

```
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccct tgcttgggtgt gtccttcgct cgctccctcc    240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagtttttggt ggcacgcagc ctggggactc tgcctcgtgc    480
cgctgagcct ggcgcagatc gatttgaata taacctgccg ctttgcaggt gtattccacg    540
tggagaaaaa tggtcgctac agcatctctc ggacggaggc cgctgacctc tgcaaggctt    600
tcaatagcac cttgcccaca atggcccaga tggagaaagc tctgagcatc ggatttgaga    660
cctgcaggta tgggttcata gaagggcacg tggtgattcc ccggatccac cccaactcca    720
tctgtgcagc aaacaacaca ggggtgtaca tcctcacatc aaacacctcc cagtatgaca    780
catattgctt caatgcttca gctccacctg aagaagattg tacatcagtc acagacctgc    840
ccaatgcctt tgatggacca attaccataa ctattgttaa ccgtgatggc acccgctatg    900
tccagaaagg agaatacaga acgaatcctg aagacatcta ccccagcaac cctactgatg    960
atgacgtgag cagcggctcc tccagtgaaa ggagcagcac ttcaggaggt tacatctttt   1020
acaccttttc tactgtacac cccatcccag acgaagacag tccctggatc accgacagca   1080
cagacagaat ccctgctacc actttgatga gcactagtgc tacagcaact gagacagcaa   1140
ccaagaggca agaaacctgg gattggtttt catggttgtt tctaccatca gagtcaaaga   1200
atcatcttca cacaacaaca caaatggctg gtacgtcttc aaataccatc tcagcaggct   1260
gggagccaaa tgaagaaaat gaagatgaaa gagacagaca cctcagtttt tctggatcag   1320
gcattgatga tgatgaagat tttatctcca gcaccatttc aaccacacca cgggcttttg   1380
accacacaaa acagaaccag gactggaccc agtggaaccc aagccattca aatccggaag   1440
tgctacttca gacaaccaca aggatgactg atgtagacag aaatggcacc actgcttatg   1500
aaggaaactg gaacccagaa gcacaccctc ccctcattca ccatgagcat catgaggaag   1560
aagagacccc acattctaca agcacaatcc aggcaactcc tagtagtaca acggaagaaa   1620
cagctaccca gaaggaacag tggtttggca acagatggca tgagggatat cgccaaacac   1680
ccaaagaaga ctcccattcg acaacaggga cagctgcagc ctcagctcat accagccatc   1740
caatgcaagg aaggacaaca ccaagcccag gacagttc ctggactgat ttcttcaacc    1800
caatctcaca ccccatggga cgaggtcatc aagcaggaag aaggatggat atggactcca   1860
gtcatagtat aacgcttcag cctactgcaa atccaaacac aggtttggtg gaagatttgg   1920
acaggacagg acctctttca atgacaacgc agcagagtaa ttctcagagc ttctctacat   1980
```

```
cacatgaagg cttggaagaa gataaagacc atccaacaac ttctactctg acatcaagca    2040
ataggaatga tgtcacaggt ggaagaagag acccaaatca ttctgaaggc tcaactactt    2100
tactggaagg ttatacctct cattacccac acacgaagga aagcaggacc ttcatcccag    2160
tgacctcagc taagactggg tcctttggag ttactgcagt tactgttgga gattccaact    2220
ctaatgtcaa tcgttcctta tcaggagacc aagacacatt ccaccccagt gggggtccc     2280 ataccactca tggatctgaa tcagatggac actcacatgg gagtcaagaa ggtggagcaa    2340
acacaacctc tggtcctata aggacacccc aaattccaga atggctgatc atcttggcat    2400
ccctcttggc cttggctttg attcttgcag tttgcattgc agtcaacagt cgaagaaggt    2460
gtgggcagaa gaaaaagcta gtgatcaaca gtggcaatgg agctgtggag acagaaagc    2520 caagtggact caacggagag gccagcaagt ctcaggaaat ggtgcatttg gtgaacaagg    2580
agtcgtcaga aactccagac cagtttatga cagctgatga gacaaggaac ctgcagaatg    2640
tggacatgaa gattggggtg taacacctac accattatct tggaaagaaa caaccgttgg    2700
aaacataacc attacaggga gctgggacac ttaacagatg caatgtgcta ctgattgttt    2760
cattgcgaat ctttttttagc ataaaatttt ctactctttt tgtttttttgt gttttgttct    2820 ttaaagtcag gtccaatttg taaaaacagc attgcttttct gaaattaggg cccaattaat    2880
aatcagcaag aatttgatcg ttccagttcc cacttggagg cctttcatcc ctcgggtgtg    2940
ctatggatgg cttctaacaa aaactacaca tatgtattcc tgatcgccaa cctttccccc    3000
accagctaag gacatttccc agggttaata gggcctggtc cctgggagga aatttgaatg    3060
ggtccatttt gcccttccat agcctaatcc ctgggcattg cttccactg aggttggggg    3120 ttggggtgta ctagttacac atcttcaaca gaccccctct agaaattttt cagatgcttc    3180
tgggagacac ccaaagggtg aagctattta tctgtagtaa actatttatc tgtgttttg     3240 aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca atctcatgg aagaccaagg agggcagcac tgttttgtt     3540 ttttgttttt tgttttttttt ttttgacact gtccaaaggt tttccatcct gtcctggaat    3600
cagagttgga agctgaggag cttcagcctc ttttatggtt taatggccac ctgttctctc    3660
ctgtgaaagg ctttgcaaag tcacattaag tttgcatgac ctgttatccc tggggcccta    3720
tttcatagag gctggcccta ttagtgattt ccaaaaacaa tatggaagtg cctttttgatg    3780 tcttacaata agagaagaag ccaatggaaa tgaaagagat tggcaaaggg gaaggatgat    3840
gccatgtaga tcctgtttga cattttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggctttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
```

-continued

```
ctcctccctg tctaccctct cccctccctc tctccctcca cttcacccca caatcttgaa      4440
aaacttcctt tctcttctgt gaacatcatt ggccagatcc attttcagtg gtctggattt      4500 cttttattt tcttttcaac ttgaaagaaa ctggacatta ggccactatg tgttgttact       4560
gccactagtg ttcaagtgcc tcttgttttc ccagagattt cctgggtctg ccagaggccc      4620
agacaggctc actcaagctc tttaactgaa aagcaacaag ccactccagg acaaggttca      4680
aaatggttac aacagcctct acctgtcgcc ccagggagaa aggggtagtg atacaagtct      4740
catagccaga gatggttttc cactccttct agatattccc aaaagaggc tgagacagga      4800 ggttattttc aattttattt tggaattaaa tactttttc cctttattac tgttgtagtc       4860
cctcacttgg atatacctct gttttcacga tagaaataag ggaggtctag agcttctatt      4920
ccttggccat tgtcaacgga gagctggcca agtcttcaca aacccttgca acattgcctg      4980
aagtttatgg aataagatgt attctcactc ccttgatctc aagggcgtaa ctctggaagc      5040
acagcttgac tacacgtcat ttttaccaat gattttcagg tgacctgggc taagtcattt      5100
aaactgggtc tttataaaag taaaaggcca acatttaatt attttgcaaa gcaacctaag      5160
agctaaagat gtaatttttc ttgcaattgt aaatcttttg tgtctcctga agacttccct      5220
taaaattagc tctgagtgaa aaatcaaaag agacaaaaga catcttcgaa tccatatttc      5280
aagcctggta gaattggctt ttctagcaga accttccaa aagttttata ttgagattca       5340
taacaacacc aagaattgat tttgtagcca acattcattc aatactgtta tatcagagga      5400
gtaggagaga ggaaacattt gacttatctg gaaaagcaaa atgtacttaa gaataagaat      5460
aacatggtcc attcacctt atgttataga tatgtctttg tgtaaatcat ttgttttgag       5520
ttttcaaaga atagcccatt gttcattctt gtgctgtaca atgaccactg ttattgttac      5580
tttgactttt cagagcacac ccttcctctg gtttttgtat atttattgat ggatcaataa      5640
taatgaggaa agcatgatat gtatattgct gagttgaaag cacttattgg aaaatattaa      5700
aaggctaaca ttaaaagact aaaggaaaca gaaaaaaaaa aaaaaaaa                   5748
```

<210> SEQ ID NO 3
<211> LENGTH: 707
<212> TYPE: PRT
<213> ORGANISM: Homo sapiens
<220> FEATURE:
<223> OTHER INFORMATION: matrix metalloproteinase 9 (MMP9, MMP-9)

<400> SEQUENCE: 3

```
Met Ser Leu Trp Gln Pro Leu Val Leu Val Leu Val Leu Gly Cys
 1               5                  10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
```

-continued

```
            115                 120                 125
Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
                180                 185                 190

Pro Pro Gly Pro Gly Ile Gln Gly Asp Ala His Phe Asp Asp Asp Glu
            195                 200                 205

Leu Trp Ser Leu Gly Lys Gly Val Val Pro Thr Arg Phe Gly Asn
210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
                260                 265                 270

Ser Glu Arg Leu Tyr Thr Arg Asp Gly Asn Ala Asp Gly Lys Pro Cys
            275                 280                 285

Gln Phe Pro Phe Ile Phe Gln Gly Gln Ser Tyr Ser Ala Cys Thr Thr
290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
            450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
530                 535                 540
```

```
Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
            565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
            645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
    690                 695                 700

Pro Glu Asp
705

<210> SEQ ID NO 4
<211> LENGTH: 4506
<212> TYPE: DNA
<213> ORGANISM: Homo sapiens
<220> FEATURE:
<223> OTHER INFORMATION: matrix metalloproteinase 9 (MMP9, MMP-9)

<400> SEQUENCE: 4
aagcttcaga gccaggcagt tctgggcttg aacactagtt ctgtggatta actcgctctg      60
tgatcacagg caaattcctt aactctctga gccttagttt ccccctctga aacaggagg     120 gatactcatt aaacttacct tacaggtggt gaggatgaaa cgagaggctt atagagaact     180
tattacggtg cttgacacag taaatctcaa aaaatgcatt attattatta tggttcagag     240
gtaaagtgac ttgcccaagg tcacatagct ggaaaatgca gagccgggat ggaaatccag     300
gacttcgtga cgcaaagcag atgttcattg ttagtgaac tttagaactt caacttttct     360
gtaaaggaag ttaattatct ccatctcaca gtctcattta ttagataagc atataaaatg     420
cctggcacat agtaggccct ttaaatacag cttattgggc cgggcgccat gctcatgccc     480
gtaatcctag cactttggga ggccaggtgg gcagatcact tgagtcagaa gttcgaaacc     540
agcctggtca acgtagtgaa accccatctc tactaaaaat acaaaaaatt tagccaggcg     600
tggtggcgca cctataatac cagctactcg ggaggctgag gcaggagaat tgcttgaacc     660
cgggaggcag atgttgcagt gagccgagat cacgccactg cactccagcc tgggtgacag     720
agtgatacta cccccccccaa aataaaata aaataaataa atacaacttt tgagttgtt     780 agcaggtttt tcccaaatag ggctttgaag aaggtgaata tagaccctgc ccgatgccgg     840
ctggctagga agaaaggagt gagggaggct gctggtgtgg gaggcttggg agggaggctt     900
ggcataagtg tgataattgg gcctggagat ttggctgcat ggaggcaggg ctggaggaac    960
taagggctcc tatagattat tccccatat cctgccgcaa tttgcagttg aagaatccta    1020
agctgagaaa ggggaggcat ttactccagg ttacactgca gcttagagcc caataacctg    1080
```

```
gtttggtgat tccaagttag aatcatggtc ttttggcagg gtctcgctct gttgcccagg   1140
ctggagtgca gtgacataat catggctcac tgtatccttg accttctttc tgggctcaag   1200
caatcctccc acctcggcct cccaaagtgc taagattaca ggaatgagcc accatacctg   1260
gccctgaatc ttgggtcttg gccttagtaa ttaaaaccaa tcaccaccat ccgttgcgga   1320
cttacaacct acagtgttct aaacatttta tatgtttgat ctcatttaat cctcacatca   1380
atttagggac aaagagcccc ccaccccccg ttttttttt  tacagctgag gaaacacttc   1440
aaagtggtaa gacatttgcc cgaggtcctg aaggaagaga gtaaagccat gtctgctgtt   1500
ttctagaggc tgctactgtc ccctttactg ccctgaagat tcagcctgcg gaagacaggg   1560
ggttgcccca gtggaattcc ccagccttgc ctagcagagc ccattccttc cgccccaga    1620 tgaagcaggg agaggaagct gagtcaaaga aggctgtcag ggagggaaaa agaggacaga   1680
gcctggagtg tggggagggg tttggggagg atatctgacc tgggaggggg tgttgcaaaa   1740
ggccaaggat gggccagggg gatcattagt ttcagaaaga agtctcaggg agtcttccat   1800
cactttccct tggctgacca ctggaggctt tcagaccaag ggatggggga tccctccagc   1860
ttcatccccc tccctccctt tcatacagtt cccacaagct ctgcagtttg caaaacccta   1920
cccctcccct gagggcctgc ggtttcctgc gggtctgggg tcttgcctga cttggcagtg   1980
gagactgcgg gcagtggaga gaggaggagg tggtgtaagc cctttctcat gctggtgctg   2040
ccacacacac acacacacac acacacacac acacacacac acccctgac ccctgagtca   2100 gcacttgcct gtcaaggagg ggtggggtca caggagcgcc tccttaaagc ccccacaaca   2160
gcagctgcag tcagacacct ctgccctcac catgagcctc tggcagcccc tggtcctggt   2220
gctcctggtg ctgggctgct gctttgctgc cccagacag  cgccagtcca cccttgtgct   2280
cttccctgga gacctgagaa ccaatctcac cgacaggcag ctggcagagg aatacctgta   2340
ccgctatggt tacactcggg tggcagagat gcgtggagag tcgaaatctc tggggcctgc   2400
gctgctgctt ctccagaagc aactgtccct gcccgagacc ggtgagctgg atagcgccac   2460
gctgaaggcc atgcgaaccc cacggtgcgg ggtcccagac ctgggcagat tccaaaacctt  2520 tgagggcgac ctcaagtggc accaccacaa catcacctat tggatccaaa actactcgga   2580
agacttgccg cgggcggtga ttgacgacgc ctttgcccgc gccttcgcac tgtggagcgc   2640
ggtgacgccg ctcaccttca ctcgcgtgta cagcccggga gcagacatcg tcatccagtt   2700
tggtgtcgcg gagcacggag acgggtatcc cttcgacggg aaggacgggc tcctggcaca   2760 cgccttttcct cctggccccg gcattcaggg agacgcccat ttcgacgatg acgagttgtg   2820
gtccctgggc aagggcgtcg tggttccaac tcggtttgga aacgcagatg gcgcggcctg   2880
ccacttcccc ttcatcttcg agggccgctc ctactctgcc tgcaccaccg acggtcgctc   2940
cgacggcttg ccctggtgca gtaccacggc caactacgac accgacgacc ggtttggctt   3000
ctgccccagc gagagactct acacccggga cggcaatgct gatgggaaac cctgccagtt   3060
tccattcatc ttccaaggcc aatcctactc cgcctgcacc acggacggtc gctccgacgg   3120
ctaccgctgg tgcgccacca ccgccaacta cgaccgggac aagctcttcg gcttctgccc   3180 gaccccgagct gactcgacgg tgatgggggg caactcggcg ggggagctgt gcgtcttccc   3240
cttcactttc ctgggtaagg agtactcgac ctgtaccagc gagggccgcg gagatgggcg   3300
cctctggtgc gctaccacct cgaactttga cagcgacaag aagtggggct ctgcccgga    3360 ccaaggatac agtttgttcc tcgtggcggc gcatgagttc ggccacgcgc tgggcttaga   3420
```

-continued

| | |
|---|---|
| tcattcctca gtgccggagg cgctcatgta ccctatgtac cgcttcactg aggggccccc | 3480 |
| cttgcataag gacgacgtga atggcatccg gcacctctat ggtcctcgcc ctgaacctga | 3540 |
| gccacggcct ccaaccacca ccacaccgca gcccacggct cccccgacgg tctgccccac | 3600 |
| cggaccccc actgtccacc cctcagagcc cccacagct ggcccacag gtccccctc | 3660 |
| agctggcccc acaggtcccc ccactgctgg cccttctacg gccactactg tgcctttgag | 3720 |
| tccggtggac gatgcctgca acgtgaacat cttcgacgcc atcgcggaga ttgggaacca | 3780 |
| gctgtatttg ttcaaggatg ggaagtactg gcgattctct gagggcaggg ggagccggcc | 3840 |
| gcagggcccc ttccttatcg ccgacaagtg gcccgcgctg ccccgcaagc tggactcggt | 3900 |
| ctttgaggag ccgctctcca agaagctttt cttcttctct gggcgccagg tgtgggtgta | 3960 |
| cacaggcgcg tcggtgctgg gcccgaggcg tctggacaag ctgggcctgg agccgacgt | 4020 |
| ggcccaggtg accggggccc tccggagtgg caggggaag atgctgctgt tcagcgggcg | 4080 |
| gcgcctctgg aggttcgacg tgaaggcgca gatggtggat ccccggagcg ccagcgaggt | 4140 |
| ggaccggatg ttccccgggg tgcctttgga cacgcacgac gtcttccagt accgagagaa | 4200 |
| agcctatttc tgccaggacc gcttctactg gcgcgtgagt tcccggagtg agttgaacca | 4260 |
| ggtggaccaa gtgggctacg tgacctatga catcctgcag tgccctgagg actagggctc | 4320 |
| ccgtcctgct ttgcagtgcc atgtaaatcc ccactgggac caaccctggg aaggagcca | 4380 |
| gtttgccgga tacaaactgg tattctgttc tggaggaaag ggaggagtgg aggtgggctg | 4440 |
| ggccctctct tctcaccttt gttttttgtt ggagtgtttc taataaactt ggattctcta | 4500 |
| acctttt | 4506 |

<210> SEQ ID NO 5
<211> LENGTH: 501
<212> TYPE: PRT
<213> ORGANISM: Homo sapiens
<220> FEATURE:
<223> OTHER INFORMATION: aldehyde dehydrogenase 1 family, member A1
      (ALDH1A1)

<400> SEQUENCE: 5

Met Ser Ser Ser Gly Thr Pro Asp Leu Pro Val Leu Leu Thr Asp Leu
 1               5                  10                  15

Lys Ile Gln Tyr Thr Lys Ile Phe Ile Asn Asn Glu Trp His Asp Ser
             20                  25                  30

Val Ser Gly Lys Lys Phe Pro Val Phe Asn Pro Ala Thr Glu Glu Glu
         35                  40                  45

Leu Cys Gln Val Glu Glu Gly Asp Lys Glu Asp Val Asp Lys Ala Val
     50                  55                  60

Lys Ala Ala Arg Gln Ala Phe Gln Ile Gly Ser Pro Trp Arg Thr Met
 65                  70                  75                  80

Asp Ala Ser Glu Arg Gly Arg Leu Leu Tyr Lys Leu Ala Asp Leu Ile
                 85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160

```
Gly Val Cys Gly Gln Ile Ile Pro Trp Asn Phe Pro Leu Val Met Leu
            165                 170                 175

Ile Trp Lys Ile Gly Pro Ala Leu Ser Cys Gly Asn Thr Val Val Val
        180                 185                 190

Lys Pro Ala Glu Gln Thr Pro Leu Thr Ala Leu His Val Ala Ser Leu
    195                 200                 205

Ile Lys Glu Ala Gly Phe Pro Pro Gly Val Val Asn Ile Val Pro Gly
210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
    450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 6
<211> LENGTH: 55461
<212> TYPE: DNA
<213> ORGANISM: Homo sapiens
<220> FEATURE:
<223> OTHER INFORMATION: aldehyde dehydrogenase 1 family, member A1
      (ALDH1A1) genomic DNA

<400> SEQUENCE: 6
taagaagtga gatgacaagc caagtatgtt atgaagcctt gagctttcat cgcctggaca      60
```

```
tcaaataaac cagtatttga atccacaaac aactgtgact ctgggagaag aaagcagcaa    120
aacacagctg tttgggcatg ccagagcgc cactctcaag ttatgtaaca gctgttgtgt    180
aattgtgcat ttaactcaaa acacattttt gagagagaaa acaattagac tttccaaaaa    240
gaaagaaaca gagaaatgtt gaaagaacac agaagtttct atctggtcat caaacataag    300
acacggggga gtcaaaggca ttgggaatga tattgcctta gaatctaggg agttggcccg    360
tgcaccaaat ctggcctgcc ttctgtcttt taaataaag ttctatagga aaacaactac     420
acccattaat ttacctatca tctacagttt cttttaaata gagtcaagta aattatatca    480
gaaaccatcc agcccagagg ctgaaaatat ttacagaaaa agttttgcaa attcttgtct    540
tagatgaata aaaagttatg tttaaatgcc tgtaagggtg actattcact gagaaaacca    600
aagcagttga tgcttgaacc catgtaggag ttctcttgtg gagaataggg tagaaatagt    660
aaacagaaat aagagtccag gtttgggagt cagactggcc tgaaatgaaa ttctggtcct    720
gcactaatag atctgtgacc ataagtaagc tactcaccct ctgtatgtct ctaaaatggg    780
gatatgaaat gagggtagaa agggaaacaa gtgctgcacc tgatttgggc aaacaattca    840
gaaattttta gtttccctat gtaagtccca tattcagggg aattggcaag tttcactaga    900
aaaaaaaaaa ttggttgatt ctccacaatc agagcatcca gagtatttta tcttgttcct    960
attgtaacgt ttgctagagc tacaatacaa taaagtattg tacttaaaat gggagtaaca    1020
ctgtttaaaa aattgtcctt cagctaaaca ttaatttaag aacttgaatt gtttggaagc    1080
cctgcttaaa tttagtcttt gtacactgcc tatgttgata aatacagaca acttccaaaa    1140
ccaggattac tttcatttta aatgagtatt aatagatgat attgccatat ttctaattgt    1200
ggtgattgtg tgtgacagtg tgttccgaat tccctaaaag tcctgctggc ttttctgttc    1260
acatatagaa aataaagata atttagggct tctgagatca cagtaggtct acttacccag    1320
cactgaaaat acacaagact gatacgatat tttaaaacta acttagggta gggtgtagat    1380
aaagggcctt tcttccccaa acagcacctt gattttctgg gagatggact gatttcctga    1440
aagccttgtc ctgaagacac ctggccaggg ttctctcctc accagcttct actgagaaca    1500
agtgcccttt tagactcttt tcaatcctca aattctctga ttccaagtct gtcagagaac    1560
agaaagttac atagtagcat taaaaagcat gagaagtcaa aaaataata actggcctta    1620 gtggccagag cagctgctgc atacacttat cacaggtttc ggctttgtaa attaattcat    1680
ctgcaaatag tgcactgtct ccaggtacaa attcgatgct ggagcactgg tttcttaagg    1740
atttaagttt aaagtcaaag gcttcctgcc ctaggtgtta caaataagta gtgtcgtttt    1800 cttttttttgc tctgagtttg ttcatccaat cgtatccgag tatgcaaata aactttagcc    1860
cgtgcagata aaaaaggaac aaataaagcc aagtgctcta tcagaaccaa attgctgagc    1920
cagtcacctg tgttccagga gccgaatcag aaatgtcatc ctcaggcacg ccagacttac    1980
ctgtcctact caccgatttg aagattcaat atactaaggt gagtaaaact tctatttct     2040 gctttgactc gggtttgcaa aaactgcatt tatgtaaagc attaaaggtc aatttaagta    2100
aacttgtgta aagagcccct tgcaaatata aaaataaaag gcatgcaaaa tgcaggtctc    2160
agtttagtgt cctgatcaaa tatgatctaa atcatatcag acaatctttc ataaatttat    2220
ttcttaaaat atttccaagc gaaaggaatt ctcttctgtg tgaaaggatt cttataccag    2280
gattcagagg actttactaa gcacttctat taacttcact atagccggca tgtatgataa    2340
gagagcaaaa tactcactag agaagcttac tggaaagaac caaacgagta ggaacaatag    2400
aaagcaaaca aggagaaaga gagcatactg aaataacata actttccaat atgtttaata    2460
```

```
aaatgagtgt taaaatdggg ggacttaagt ctgataattg gattcgaaaa tcttcagatg    2520
gacttgcatt attttgcata ttttggtggg aggaagaaaa gcattatttc ttcagccaag    2580
tttgttgcca ttggagcaga tgtgtaattg ttaactgata aatatttaga gaaacaagag    2640
caggagctag atccagactt taaaatccgc agctgggggg aactaggaaa tggatcctgc    2700
ttgagtcgtt ctgagagtaa ctctgaactt tgcctgtttc acactgcttt cctgtcagat    2760
cctagaactc caaacaaac aaatgaataa aacacaatct aaccaaaatt acttgaagtt     2820
atctttatgg tgtgatgcag aaagtatggt aagaaattaa ctcttgcaaa tcaagagaga    2880
gccattttgc tgtctgaatt agccaacagg aaaaacaaag ggcattataa tttaatgata    2940
aagtaaaagt ccccactgtt atatatttat ttcctcactt gtaaccatgg atggctttga    3000
aatcccaagg tctgttgcat tttcattttc ataaagcaca acaaatgagg aagttgctca    3060
gctgattggc tcttttcctc aggaaagtag cagcagagat cagattgtgc ctttaacatg    3120
gttgaccagc agctatgaag tgtatttaa ggtattgtta tcacgaggtt ttgttaaaga    3180
ggaaagattt tttccattta gttttactac aaatggtagc atgaaaaatg cagtaaatcc    3240
ataccgtcaa acaatttaca tttggcaaag gtatgtccaa aaggttgcaa gagtccagtc    3300
tccctcattt tcttattcca agtttgtcat tcacaagaaa tttcaattga aagtgggtac    3360
atttaaaaat acatttcatg aagctcaaaa ttgtcgacaa tgctcagatt attgtattac    3420
tattattaat gggatttttt ttttaataat actacctagg aagatatttt ggtagtctgg    3480
atgcccctgt ctccccactc ctttggcttt gcagaagttt gcaaagtctt ccttgtgtgt    3540
gtatttcaag gaagctctaa tgtaaataac cttcctgcta aattaagctt cacttagtag    3600
tcattaacta agcatgtaag aagcggtact agacaaatga gatggtccta aaaatctaac    3660
atacaagcac agacctaatg aacccttaac acagagagat gattttgaga ttgaaaccta    3720
ttcacttcga agtcactgtg caacaactcc cctctaggga aagtgactga cctaagtgtc    3780
caaaagaagg caagactcaa agagcaggcg ttttgctctg tgtttaagaa cttttctggg    3840
taaaaatact ccaaacaagt cagtgaattt tgatttctcg tgcatcttct atataaatct    3900
gttctgctca gatagcattt tattgtttaa tttattggtt acagcgtttt cacacttggg    3960
aggacgccag ttatgtatgt aattaaatct aaatgggtga actttttcaa atgccttcgc    4020 atttttgtt tactatgtcc cagtgaagaa ttggattgaa tttgctcttg caagaggagt    4080
taaaaaaaaa atgatggtta ttaactataa aaagttccct ggttacaaac caagtaagca    4140
aggagtttat agtgtctgag gaattatctt ctattaccag cccctaaagt cttgtgttat    4200
ttttctgtta ctattctaat gtccttttt attattatta tagctagaag tatattggtt    4260
gttaggacaa gttggagaga acagacaggg ttgagtaaaa aaaaaaatat tacaactacg    4320
atagaaaagc tacatactct caagcttggg actgcttttc acccaaacaa aagaatttat    4380
tgatgcatat gttttatga cttatttct agtacagtct gattatttct ttgttggggt     4440
agattaaaga gagatcagag tttaagaaat gctttctaaa attatacaaa agcttttgga    4500
atttaaaacc tcaaaaacat cgctataaat tcactaatat gaactcatat cccatcctta    4560
tcctcattac tcctctttcc aactctaaat gaaccccaca ttttccattt tattgagcct    4620
ttaaatgaag agattctttg aaagttatgt gatcattggg caagctacat tacttctctc    4680
tgcctcggtt ttcttatgtt taaaatgggg atgataaagg cacgtatttt ctaaggtcga    4740
tgaaagtatt aaacgaactt aatgcgtaca aagcccttga aataatgcct ggacatggga    4800
```

```
aatgatttaa cgttagtgat cctagtccta ttttctgaa tccttcccag tttttccaga    4860
attttccctt ttacccaacc tttcctagac ctgtttccta caagtatgcc tcacgtcttc    4920
tcctagcttt tctgtcactc tttttttgtac agtcatgtcc catctgacaa agattgcatc    4980
agagtgaagt tccaagggtc ttccaagatt tcagggatca aaaattttct cctacaggat    5040
tcggtaactt tgtttgccat tctctcttca caatactgtt gttttacctt ttcttttttc    5100
tttttttttt tttataaaag ggaaatagga aattcaagaa acaagcatt ctcagacaga    5160 attcaaacgc caaaatgttt aacttaatta gtaagcttca cttattaaac catggtttgt    5220
tcatgctaca aaagaccttc atcagctaat gacattttac tcatacatac acacacacac    5280
acacacacac gcacacacac acacaataaa taattatagg taaaatttat tgtgcttact    5340
ctgccatgac tgtttaagtt cttgacaatg attttattta ctcctcataa taaccctatg    5400
aggaggttac tattcctgtt tcacagttca gggaactgag gaacagagcg gctatgtaac    5460
ttactaaagt tacacagcaa gtaagtgaca aagctacact gccaatgctg gcagtttgag    5520
ctaacacact agcaagagac ttgtctaagg tcaattccac tactctggga cactgacttg    5580
ccagaatcct cttgtatcct tcttcatcct gactttcatt tgcccattgc tgattaccat    5640 ggtcttcca gctgctgctc agctgttccc aggccaataa gagaaagttt gcagccaact    5700
tagaaaaaga gaacaatagg gaaattgaaa ggaaataggt tttctgcttt gactgaaaat    5760
gtgacgtttg ggctaggaga ggctatgagg cagaggactt tgacatggat gtgaaatgtc    5820
tgtgtgaact acatttcttc aactcctatg gaatcgattt tggttagagt aggagattgc    5880 ttcctagat ttctggtttt gtttaaccct tctgggttaa agatatatt tcaatggaga    5940 agagttatga atcattgaat aatacgtccc aggcacgatt tgaagtgctt ctttccccc    6000 atgattatct ctttaaattc ttacaacaaa caaattcagc tacatgaact tccaaatacc    6060
tcctttgtcc cctttgcttg tttctccctt ttgcttttcg tttctcccat atttcccttc    6120
ctcttattta acaaggcctt gaatgagtgc cctatgctag ttctcatgat ataagagggc    6180
taatatgatt cacgtctcat gcagcctctg ttcctggaag gtgtgtggaa tagtgtgggg    6240
cagaaaataa gagaatgctt taatcagaaa ttaggataaa tgtttaaagc aaaataactg    6300
aaagctgaga gaatatgagt agaagagctt ttgatgagga ttttgggaa ggtgctttaa    6360 aggtaagcct gagggatgta gagaataagg tggccaagag tagggaagaa caagatcca    6420 gaggtcttac cacatgcaaa gaccccgagg acaagagcat gttatgctca aagaactatc    6480
caaaggctaa tctggctgga gtaaagtgaa taagggagag aatggatgag atgaaactga    6540
agtacaggct ggggccagat cggctggcgg attttgagga agatcactga gaggtgctta    6600
aaacaggaaa ggacttatgt tcaacgcaaa gctgattgtg ctgtgatgct gctttcactt    6660
gggaaatgtt tttaacttcc ttccaactga agcaatattt tgtttgcttt gggcttggaa    6720
gcaggtgaaa aaaatagctg actggctgca aggtgcagtg actgaacaag ctaaacctgg    6780
cttcaatttc cagctattct atgtatttaa ttatatgacc ttggccaagc ttctcatccc    6840
ctggagcttc agttcctctg tctgtgaatt gggaatgaga atgactacct tggaaagtgg    6900
ctgtgagaat taagtgaggt aatttgtgga atgtggctgg cacttattaa ctacttagtc    6960 cttctctcc ttgattctct ttcccaagat gactcctaga attatatgat cattctgttc    7020
tcaatgtaag ttatattat attgcttatc acagctcaaa actgatttca tatatttctc    7080
tcatttgagg tgcatcatta accactgaga ggagctagaa aagatgttag cagagtccca    7140
tttcaaagct gaggagcccg agctcagaga tcatgactga cttaaggtca catagctctt    7200
```

```
aaaatgcaaa agtagaataa actggattct aaatctttt atcttggatc tgatgctttc    7260
ccacatgata tccttttttc cttaaatatc aaaaccagta gtactagaat ctcactcaag    7320
aaaacctaat caagaaaaaa atctgaagta aataacacat atcctaagag aagagggtat    7380
tatccccctt tcccaattag ctctaacaac tgttttcaca cctattactg cattttatc     7440 attcattcct tactgtggtt gaaagaatag atctaggctg aagtctgaga ttctgtgttc    7500
ttaacagtct ttcagctttt gctgatgcta ccaaaatgtc tgttgaccag cagcaagggt    7560
ctaaaagttt taggtgagtg agccttataa cttcaatgca gcaaccacct tccagttact    7620
tcacaataga gcttccagtt tcttccagaa actagcactc agccacatca gaaactttcc    7680
tttcagaaag tgccagagct aagcagaaac atgatgatgg ctacaaacca gtgacagaac    7740
caatcattga tttaatagt gggagataat catttactaa tatttagaat gctcatctct     7800
gaggactgct gtcttggcaa gttgttttgt tttctggcac ctgcctgact gtaagaaaat    7860
ggaattaaca attctaaagt aaagaacaca tgtcctaaga gagggtattg tccccatttc    7920
ataagggctc tcagtacaac tctttatata actttgtaac agggacttta acctattgaa    7980
tttgtcacta catacttgcc agaatgaggg aaacactctt agagaatatg aaaaataact    8040
catttgaaga ccaacccaaa gtaaaggtaa tgactctgaa atggcatgga taatctatag    8100
gatgatatgt tgcaaatcag cataaaataa atctcacaga aatacagaca tcaaacagag    8160
atatctgaaa atagcaatta tctggcttgg gatggtggtg tgggggggtg cactttggtt    8220
tgatttatca tgatgctatt ataactatag ccagggata tattatatgt ttacaaagtg     8280
taagtgacaa catagaacca tgttcaaaag aatttgagca aggattgctt cacaaaccct    8340
tacttagaat ccaataaatc agaaaagtaa atctgtgtaa tactggtttt cctgacgctg    8400
acatgttttg ggtgtataga tgtatatagc aaaagtatcc acaaacttag aagcattgct    8460
tgagaaggat gtgaagtgtt gctaatattg ggttttctga tattatctct acctgattca    8520
ttgtaacgtt tgacttacta atggaaattt gttcactggg gaatttgcac aaatctcaca    8580
tctctaaaaa ctttgcctga accgttccct cccccaaccc tggtcccatt tccactgact    8640
atttccactg ctctatcgat actttttag atgtcaaagg aatacaaata actactgaat     8700
tatgctttat atttggcatt cttttagaag gaagagggct tacatgcgag caattctatt    8760
actaggtctt gatactgcta aaaatgggca gaactttcta tcgcttctac atcttaactc    8820
tgatacagaa aatatatgat gtacagaagt tgctgacaag ttttgttatc atctctagga    8880
cacagtgatg gagtggctca aaacaaatgc tgtggcatct tttctctttc cctgacacaa    8940
ttgaaaaggc tgatggggtt ttgcaaacaa caagaaaaaa gagtatatac tcacgttact    9000
aaagtcagac tatcatttaa agcaaatgaa aggaaaattt tatttctcct attttttgtt    9060
ttcgtcattc tgtcattttg ttttcattca tttgatgaca gttaaaaatt ttctttccct    9120
ttgttatttc ctccttaatt tccttttaca ttttctaact ttgagtctca cattttgct     9180 ttcctgcctc agggttaggg tgcaaagcag ttgccagaga tccagctttg attcttttaa    9240
atgtttaaca ccccacctga cttttgttca gtctctcctc ctcattattc atctccgatc    9300
tcatactccc tgactcccag cggcctttag tactttggta ggttcctaag ctgagaaaag    9360
gttgacacat ttacagcaca caccagtctc cacaggttca caccaccacc catgcagcct    9420
atgctgtgac tcagttctca agtttgaaaa ttcacatgga tgcattaaa tggggactct     9480 catcacccctc cctctcgttt ggaaaatctt aaaagaaatt ctttgtgcat tgaaaatgtg    9540
```

| | |
|---|---|
| atctcttaaa atctctctcc caccaagaaa gtattgcctt cctttacaga ctctagggct | 9600 |
| gctggcccag ttgctgccct gccgagataa tattaattta aggcactctg agtatctttt | 9660 |
| gcaaggagtc aggggctccc cactttagcc cacagactcc aaaatctcat atcagcagat | 9720 |
| aaggcaaata gggctttatt ttgccactag tcaaaactag ctttatccaa gccagaaata | 9780 |
| ttttgagaaa attatgctta tttatttaga actgtagatt tatacacaat acattaagac | 9840 |
| ataataactt ttactctgga aaggcaatt ttttcacaat tatgactaat tcttggacac | 9900 |
| cagttgaatc caggaaatgg ctacttgttt atcaaaggta aaatgatgca tttcttaaaa | 9960 |
| tgtggcatat ctaaaatctg aagtgtaaaa atccatttct aagttgcctc aacatttcta | 10020 |
| ttgattgctt ccccatatag aaagtacttg aagtccaaga gtatgcatag gcatttataa | 10080 |
| tttccaatca atatttcaaa cagaaggttg atgtctactt tacatatata ttattcaaaa | 10140 |
| gtcacctaag tccaaaattc ataattagaa ttgagttaat atataatggt tacatagaac | 10200 |
| ccaagaatat tttactttta tagtatcatc tcttttcctc taagctggct aaaggcaaaa | 10260 |
| aacaaatgga aaataatatt gtcaccatta tagaacatta aacaagccta atgtaaattt | 10320 |
| tataattatt ataacaaaca ttcattagcc tagacttctc catataacca ttaatataac | 10380 |
| tataggaaca gtgattatac aaaaacgttt ggtcacacag ttagctggaa ggcaaatgcc | 10440 |
| caatgtaaag ctcctataat taaaacagaa aaaaaatgta tttgaggtag gccctatgaa | 10500 |
| taaattatct gtagctaagg ggaagaaaaa gactgggcaa tacctggcct tctaaccatc | 10560 |
| taggtcatca cattacctat gccaaattcc cttttcatgc tgaaacgcct ctgtttgtgg | 10620 |
| gagaatggca taattcataa tttgtagact gcactgttac atcactctcc ttcaaaagcc | 10680 |
| tgtgacctta tgataggatt atgaaattag tctcaaggct aatttcttgg actctggttg | 10740 |
| gtctacttca aatctacttg ggatacttta aaatcagtat tcctaaacat ccatttgatc | 10800 |
| tggtctctct ccctttttat atccagaata gagcctaaac ttctttctct ggggatcagg | 10860 |
| atctgccaca aattgacttt attttcaatg tcaggcctta tctgtgactt atgtccactg | 10920 |
| caactccatt ctgttgggag ctgctctgtt tactgtgtta caaacctcca agatttgtc | 10980 |
| cctccctta ctcttttttt ttccttcttt ccaccaatcc agttccatcc ttcaaagaag | 11040 |
| cattctttca gcctatgccc ctctacacca tttattgaca acaccgctgc tttggccatt | 11100 |
| ttgctccaca gtctttaatt ctgtactggc ggctcttgat atgaatacat tctcctctta | 11160 |
| gattataagc ccctgagagc agaggccatg gctaactcat ctctcatttt tccacaataa | 11220 |
| ctgccagact atgtctcaag tatttactca ttattggaca aacacttttc tgataaagca | 11280 |
| aaagttacta atcatgatta tataaatgtc aacacaagtt caaacacaag ttgggctcac | 11340 |
| agtgtcctcc tgtcttaaag gttaaaactg aataatgcag aacagtgctg gtaatttggg | 11400 |
| gtcctctaca gctgatctct tcagttgcct gcaggctgcc agataaacat gtgttattac | 11460 |
| ttcaggttaa tgctcattta caaaacattc actggcttta atctaaagtg gcagtttat | 11520 |
| gtacagctta gatgcaaatt ctgatcatgg aactagatgg tacatacata ctgtaataat | 11580 |
| tcttttacaa aaaagtgtgt aaagagagta aaataagcta taatatattg agagcatatt | 11640 |
| attgagaact tgaaaccaca gattatcaca gacctaagga taagaggact cgggcgagaa | 11700 |
| ctagaaagtc cgaccacagg cctagcaaaa tgtaattgat tctgtatgtt gttttatttt | 11760 |
| atttttaatg aaattacatt gtagaagggt gaaattctgg atctctgcca aaatgaaatc | 11820 |
| tgtgttccct tagtttacag gtacaaaatc taaggtggta atacaatctt taggcagaga | 11880 |
| gaaggcagaa ttcccaagtg aataaatctg atgcaggttt tgaaagactg atttaaaagt | 11940 |

```
ctacggcagg tatcgcaata tctttagttt tttgtttgga attttatggg ctgatatgta    12000
gatatctaac attaacacaa agcagaacat aagtaattta tcagtaggat actaacatgt    12060
tatgttggaa agaagaaaaa agagattaaa ttcaattgga gcaactagtc aaatcttcat    12120
gaggagatga cgcagtaagc tagaatttga agtaaaaata gaagaaaata gtggaactct    12180
agtctaaaga acagtgtgaa taaaagcatg ctgcaaaaaa cagcatggtg tttgaggcag    12240
tagaatgagg ctggaacaaa gggtaaactg agggaatggt agagcaaaag actggaaaag    12300
catgttggag caagatcgtg aaccacctcc agtgccatgt taagcagtct gacaatagag    12360
gatcactaaa gtattctgag gagggctgta gacagaatct gaggaagatt atgatgacaa    12420
ggtgaaaatt aaattttaat taggcagagg taggggcaa agagaacagg gaaagctttt    12480
ttatacttgt atagaacaaa gtgatacaaa agggtaccta gggattattt gtgtcattaa    12540
cagaagaagg aaagtgtgtg agagatagg ctgggggaca gtgtgcatga gcaagcttca    12600
gaactttggg gtgagagcag cataaagcta gagatgacag tgagctgagt tcgggacaag    12660
ttgattaagt tctttcccag ccatcccttg agaagaaaaa tactaagctg taagggcata    12720
aatggaaaca ctctaagaat aattatggga ttctgtaaaa tgtatttctg atagctagag    12780
tgttgattca ctctaagaga cattgggcaa atcagcactt tcgtctgaat ttattttcc    12840 tcaagttgat ctaagagcct aatgtttttt cccaaaagat aatacaatga attttatggt    12900
cttcatctgt attcagttaa tcttgtttct gtaatctgat agggtttctt gatacttctt    12960
ccatctttct catttcccca tatatgtatt tttgcacatc tagtctcttc atctgaacag    13020
ctttgggccc cttttccctt tatttaggca tgcccatgtg ttttaccatc aatttcaggc    13080
tagtactaca attcctttga atgcttctaa ctatacagga taattttctt gtatggaaat    13140
aatgctgttt tcttgtatgg aaaattatac tggcatgaat gggcaaacaa gacggcttat    13200
cctcttcccc attttgtagg aaatcacaag tgtcatagag tattcatttg cagaacgtta    13260
tagatcttat ccatgagtag ctgatggatt atagatcttt gattcaatta agttagttat    13320
tcaagaattt tttactgagg ctaaaattgc ttgagggctg ttggacactg aagatagact    13380
ggaaaaccat acacagccct tgatggaagg cagacactta aaaatgacta tttaaaaagt    13440
gacaaattgt ccaatggaag tatagaggag accagggaag tatattttgt ctaaataata    13500
aatcacagaa tatagaatga attatattca ggcatttagg gatatatagt aatatacatt    13560
ttattactct gatagaattt taagctatgc tagtgatcac cggggaattt ttaataaata    13620
agtaatttgc atttagcata gtagctaatt taaaccttgg aggagtgttt cattacattc    13680
tccctcgggg ttgaactatt aataacttat ctttagatat ccagtaagaa gggatgtctg    13740
aattaggata tatgttataa tccagcacat atgtcaccct cctttactcc ctgtgttagc    13800
tacctctgat tcaaaataga ataaactagt ccatcttgtc ataagtctaa cagaaagtta    13860
tatactatcc aagactgtat ttatgattgt tttcatattt caaataatta gaaatgtgaa    13920
agctggctcc tcaagaaaag acaaattcag tgacatgaaa gttgaaactg agatgtttta    13980
aatgacatac tgatgctttt aagtatttct attttatagt acacacagac aaaatttcat    14040 atttttagt gcttactgtt tctttagttg catgtctatt tctcatagtt accattaaga    14100
aatcttgttc ctgattttgt ctgaagacaa cgaaattacc aggtaatctt ttgaaaagga    14160
gaataaaacc atatgctttt aaaaagccaa tgaaacaatg tgactagcta attttctcta    14220
agtgaactcc ttttagaatc ctttagcaaa attcttttt taactttaaa acattaaagg    14280
```

```
attagaaaat agtctcttat gattccaaat caccagtagc cgaaaatgag gatgttcaga   14340
atttaaagtg gaaaatagaa gcaatcatta ataaagacca agcccacaaa agcctttgct   14400
ttgcctcaaa ttcatggcca tttcaggtaa aagcattgtt ttctagattg ttttctccag   14460
tatgtatttt ctagtgttga actgattgca taccttaaac ttaaaagcat tatgtacttc   14520
attttagtac atgtctatgc atgtgaacac aaaatgtctc aaacagccag aaagttttga   14580
gaggtgaaga gatgtgcatc atttaggcat ggtgaaatgc tttagtttaa gtttatgaaa   14640
acttccaaaa ttttctgcat atttaagcgc cttgtatgta ttttctcttc atctctacag   14700
atcttcataa acaatgaatg gcatgattca gtgagtggca agaaatttcc tgtctttaat   14760
cctgcaactg aggaggagct ctgccaggta gaagaaggag ataaggtgag tttctgaaca   14820
ctagtttcat tttatgccag gtttcttggt tttttgccat tctgagctcc tgaaccccat   14880
tgcaagctcc aaaagacatg ccatgaaaat atggtttctg gggcagctta ggaaaattgt   14940
ctaagttgtc cttgttacca aaaaaaaaaa aaatgctctg tagttatgta ataatgataa   15000
acctgtgctt ctgggtgtca tggtgatttt ttttcacatc attttccttt attttcaatt   15060
gaaatagtat atagatttat tttacagact atataagaag ggattgatca taggttataa   15120
agtagagaaa tcttcagctg ggcgctgtgg ctcacacctg taatcccagc actttgtgag   15180
accaaggcag ttggatcact tgaggtcacg agttcgagac cagcctggcc aacatgggga   15240
aacaccgtct ctactaaaaa tacaaaaatt agccaggcat ggtggcacat gcctctaatc   15300
ccagctactc aggaggctga ggcaggagaa ttgctttagc ccgtgaggca gaggttgcag   15360
tgagccgaga tcataccact gcactccagc caaaaaaaaa aagaaaagga aaaggagag    15420 aaatgcttta ttcatatgaa attgttcttt ttatgttgct agataaaact aaaagttatt   15480
ataaactttt tagaacaata tattactaag ttatttattt aaaaatcact gcattaatat   15540
tattattcaa cacctgtaaa aattatatta tagaataact taaattgact aacaaattac   15600
aagcgttgtt attttccagc taataataga acaacaaaa accagttttt atttagtgaa    15660
aattgttctc aagttctaaa tgctatcttc atttaaaact taaagcaacc ctatagggca   15720 ggtactatttt tgagtcattt ttacaaataa tgatgagatg gcagagtaga aaggctgagt   15780
aatttactca aggtgacatt gctaataagt aataacctca acattaaaat gctgttcctc   15840
tgacactata acctgtgcct agtagggcta ctgcttcact ttgtgattat tatgaaagta   15900
agatagggtt ggccgggcgc agtggctctc acctgtaatc ccagcacttt gggaggccga   15960
ggcgggcaga tgatctgagg tcaggagttt gagaccaacc tgaccaacat ggtgaaaccc   16020
cacctctact aaaaatacaa aaattagctg ggcatggtgg tgggttcctg taatcccagc   16080
tactggggag gctgacgcag gataattgct tgaacccggg ggtcagaggt tgcagtgagc   16140
caagatagtg ccattgcact ccagcctggg caacaagagt gaagctccat taaaaaaaaa   16200
aaattaaata gtcttcttta ttatgaaagt aagatatccc agcactttgg gaggctgagg   16260
cgggcagatc acaaggtcaa gagattgaga ccattctggc caacatggtg aaacctcgtc   16320
tctactgaaa atacaaaaat tagctgggca tggtggcgca tgcctgtaat tcagctact    16380 cgggaggctg aggtaggaga atcacttgaa cccggaggc agagcttgca gtgagccgag    16440
atcgcatcat tgcagtccag ctgggtgaca agagcgaaac tccgtctcaa aaataaaaa    16500 ataaaaaatt agatagcata atattaaata aactttttat tctcctcctg ggtgaggaga   16560
gtaaaaaact tcagaatatt tttctgaaca cgtaagtgtt tctaagtcta atttgaaatg   16620 attttctgc tctttagttg cccagggggtt gccaagtttt aaatttctgt aaagaagtaa    16680
```

```
tgttttattt tattttatta ttattattat tgctgcagga aaagactact gggaaattaa    16740
agtcagcaac acccaaggat aatattattc atgacaatgt gttttagtta attatagcga    16800
tcacatgttc ctgccagtct cctgcccagt cttttccatt acttagccc cagtaaatga     16860 gatcacaaat ctcaacgtac tgggccatgc agatacttat tccaagatag tgacacacct    16920 gaggggggccc ttttagattt aggagaggcc cttggttcag atttcagtac gatgaaaaca   16980
agtaagaccg aagtctcaag ccacaggagt acggagttca accatagggg ttaacaattt    17040
gagaagtaga aacaaaataa aatgatgaca aatgtcactg gctttcagat tcagatttac    17100
tctttatact gaagagttca ccaaagcata aattctccat tctgcttctc actgtctgtg    17160
ggaaaaagtg cacaaacaaa ggtcctttat aatattactc aacctttgtt tatggcctct    17220
ttcccaggcc accgcattaa cttaagagtt tcaacttcgt catgcccagt gtccatcccc    17280
aacaattgct tgctagtcac tgcctctgta catgtccaca gtgtagtcct caggacctag    17340
ttcaagtcac catctatagt aagagcgtag atttttcaatg tttgtactta accttctttg    17400
agattctgtt cttttttcatg taaaatgagg agatagaaaa tgcttgagga gttaaatata    17460
tagagctctt caacggtgcc aggcatatcc taaagcttca gtcatgcccg ggttttatac    17520
ttatttaaag ccttctctaa ccttctcaag cagacttact ctcttctgtg tggttatagg    17580
acattgtatt tgcctgtatt ataacctttg tattatacag ctataggtta atttgtctga    17640
gacaatatgc ttcttgcaga gatcaacact gcatctctca tttatatcct tggtttctgg    17700
atatagtata tcctataagt atgctatact atattcgata gatatactat actatagata    17760
tagtatattc tataaatcta tgaagtagtc ttcttttttca tcaagtgttg aatttccata    17820
cattccacat tcctcacctt aggaatttag tactaacctg actattggct atggcagaca    17880
ttctcaaaat ttagcctgtc tcagaatgtc caggaaggct tgttaaaaca cagatagctg    17940
agccccacct tccctagat ttcactgcaa taatcttaga atgggacctg aaaattttca    18000 tttttttatca attctttggt aatgctgatg ttgttggttg ggaaggaggt gagggaatgc   18060
atcttgaacc accgaactaa agtgttaagc tgttaagttg tatctcctct caagcgttaa    18120
catttaacag gggtcaaaga gttttgacac ctaagaaagt tagtgattga aaactgtact    18180
gtggtgatca ctctgcacct ctctgaaatg ctaccaaacc aaaattgggc atagaaatac    18240
tgatcatccc tggcaaggtc tataggagcc ccagaagcct gtgccctata agccattccc    18300
agaaataaga gagaaattta ttcttcacct ttcaaagaag aatgaacgcc ttttatcaga    18360
gacttcagga gatccacaca ccaccacctc aaatgttcct ctagttgctt gagtggctct    18420
agcaggcctg ggaaggtgag aaaagcaata aagggcaagg acagagtgag cccttgagag    18480
ctacatactt tctctctcca ttcaagagga aggccagatc tgtttgcagt ttgcaactaa    18540
caaacagaaa aatattattg atgttttaat tctggagcct tgaacatcga cctttgccac    18600
tgggattaat tttattagga aaacaaatct ctatgcccaa agttccagtt gaaaccttgt    18660
caggcagtct gaggactttt cttagtgaag tttgtgggat ttacctcctt cctaaagtat    18720
agtaagggaa agctaatgat catactggaa gacttagaaa tgtttgccac tgatttgctc    18780
tgtgcttctt gacaattact attgcttacc caagagatca aggatgctca ttaacatcta    18840
cccaagcttc aaatcaggtc acaatgccaa ctgagttggc tggtcaactg gttactaaaa    18900
ctaaaatgtt gatggtataa actgttcatg gtaaaccagt ttgaacatct agcactctta    18960
tcatcacatt cttttttgaa ttattttaaa acatattttt aaataattat tgctcttccc    19020
```

```
acaattttgc cgacaaatgt atagtaaact ccgacattgc ttagtgaaag gtacaaatct    19080
agtaaattac atagtcacag taaacctaat atgctgtatc tgactctttta gataatgagc   19140 caagaggttt tagggattta atttgtaagt agaatggggc taacaatggg ctatataccg    19200
cctttcaacg gtattataaa gaaaagagga agggcaagaa caaatggagg ttacaaagca    19260
aagtacagat gtgggtggga actgttttct tttcacttca gtggttcttt taggctatat    19320
tgactaatcc tgaaaactgc ttttaatact aaggcatgac ctaacaaata attggtgggg    19380
ataaaagtaa atgtccgtta aagtaagtgc ctttgacatg tgtaaaagta aaactggtct    19440
gataactatt ttctccatct ctgaatgaat ttaatatgga aatgtaccat ctgggagtga    19500
tggaagagtt cagtccttcc ttaactgtgc tttaggaggc atttgatatc tcatcatcat    19560
ttgaactgtc ttttacatt cagcttgtgg cccttacttc aaaaaaaagg agcattttca    19620
gtgctataag caaaattgtt attgatggtg gcaaatctga gttaatgtac caaattgttt    19680
tctgtttaat taaaaaatta tatccctgaa aattccagtt ctgaaataaa aatttaaaaa    19740
atgctagtcc tggaattaag aaaacaataa ctgttatgtc taacagtttt tgaataatgt    19800
ataagttttg ttgtatcatg gaatctatta aaatatgatt tattatgtaa atgccaatgt    19860
agttaaatta attatgtaag gcacccctta tataaaatca gtacaacatg atgagtttat    19920
aaaacaggta accaaattat tcaaaattta tttattgccc attgtagacc cagaattgta    19980
agaaatatta cagtttacaa aacaaatagc agtatatatt tgttgcaaag gaggtcatta    20040
ttagggcagc cttacagaga tgtaagaact agattttgta gtcagatgtg ggatcaaagg    20100
ttgattctac tgtctgctag atttcatatc catgagccat agtctattca tttataaacc    20160
aaggctcatg atacttaata gtaatagtaa ctatggggct ttaaagaact ttccttagtg    20220
cctggagctt agtaggctct tagctagtag ccatcatcaa gctggactag tctggcaagg    20280
ttttaggtag attgatattt gagctgggtc ttaaagtata tataggattt agaaagtaag    20340
ggagtatact ggtataatat tctaggcaag gagaactaca gacacaaaag taagaaggag    20400
ttgggtcaga tagagtagaa aaaatgtaaa cactaagttt ggataggtga gatgtggtct    20460
gaaaatcctg ggccttgaaa accagggagg actttgacct tgagattgta gatgaaaggg    20520
aacaggtgta aacatttgaa agacaaagtg ataagataaa attatttgca gaagattagc    20580
ctggtgatag tagccaagat agtttgagga gagaagagaa tgaacttgag acagcattga    20640
caatatgaaa taatagggcc taaaattgtt cagagcagtg aaaactgaaa ggaaggatta    20700
aaatacatta gaacttgcta ggtgcagcaa tacacaccta taatccctgt gtgcctgtaa    20760
tcccaccacg ttggaaggca aaggcagcca ggttgcttga acccaggaat tttagaccag    20820
ctttgacaac atggcaaaac cccatctcta caaaaaaatt aggcagacgg tggctcatgc    20880
ctgcaatcat agcacttcgg aaggtcaagg tgagaggatc acttgagccc aggggtttga    20940
gaccagcctg gacaacatag caagacctca tctttactaa aaataaacaa ttagatgggc    21000
atggtgatgc actcctgtag tcccagctac tccagaggct gaggtgggag gatcacctga    21060
ggctcgtcag gaggtctagg ctttggtgag ccatgtttgt gccactgcac accagcctag    21120
gcaacagagt gaatctccct ctattgagag agggagaaat tgctgagagt tatattaaaa    21180
tttaaagttt taactgctag gacaacagta acaattgcca ccattgaata atacataatg    21240
ttctaacata gaaaatgttt aaatgttatc ttattaatct tcattacaac cctgtgaggt    21300
aacatacccc aatttctttt ttcttttgtc ttgcttttc ttttttttt tttttttt      21360 tgttttgaga tgagggtctt actctatcac ccaggctgga gtgcagtggt gcaatctcag    21420
```

```
ctcactgcaa cctgcacctc tcaggttcaa acgatcctcc cacttcagcc tcctgggtag    21480
ctgggactac aggcacacgc caccacacca agcaacatac cttgatttta aagaaaagaa    21540
agctgaacct tagagaagtc atgccacaac atatttcatg gtttataata atgttttggg    21600
atagtgattt gattgtatgt ctctcccatt tgattgaata ttccaaaagg acaatcttct    21660
tacttcactc tgctgtcttt agcggaggga tgatgagaat gctgcagagt cgaatattta    21720
tcaaaccttt agctagaggg atgaatggtt agatgcctca aggttacac agctaatgaa     21780 gaggaatcag aattcaaatc tgggttgttt tcatatcaaa ctatatatta actaacatta    21840
ctgtatttct gcatctgcaa gattacatat aagatgtgag aaaaggggc gcatgatcca     21900 aaggacataa tcataagaac atctttattt atagcagcat tctttaggga tgtgctttcc    21960
atatgggaga gttacttatc ttgaagccag ttctccgtat ccctttggga ggccaagatc    22020
cctatgatag cccatatttg gctaagacca atagcaggac actgaacaga aagatccaaa    22080
tgaaagctgt gtcatacaga tctgtttaaa cacagaccag catgtatttt ataagctctg    22140
gtatccacag atcatgctga caatctcaga ttttttgtggt ttgcttttc ttttttttcaa    22200 acagtgctct gtaaatttag gaaaaagtta gaacgtgtgg catgaaacaa tgtctaaata    22260
taagcaatca atgtgattaa ctgaatgccg caaatatgca ctgtatatgt atttctcagg    22320
aaaggcaggc aataaataca tatttttgt atatatcatc attctctgaa aagttagaca     22380
gtgagatata tcagtgtgtg atgtattaca ctgaaagaat ctttgcttgt agtcagtaaa    22440
tattattact taatcagacc agattgtgct tctaaaatat ctctcttgcc ccagatcata    22500
ttattttggt gataaatact agaagaatag ttttttttgta ttttaattca cagacttgta   22560
agtgtgggtc ttcttgattg aatatagcct aaggaggagg atgttaattt gaggtccatt    22620 tgagggaag atatctcctt agatgggatt tagcttaatt gtgtacaatt ttttaaaaaa     22680
atctagggtc attactttt ctctccccca attcttaaag ggaattgtgt ctcctgcaaa     22740
atattgcaac ctactggcct gtgatatagc cactatttgt ggagctatac aattccatgt    22800
agtggccagt tctatgtaca aaagaacact ggaatgatat attcctttat ggtgtttgca    22860
gtagtagtag gtatgttctg taagagctca gaagaggtct gaacagggat ctgcagggga    22920
gtggagtggt cagggcaata tttgtaactg aggtgaattg caaaagaacc agagaatata    22980
tctggtgtag aaaaacacaa cagagaaaga aattgagtga aggcactatg agagtgaagg    23040
acaggaggct acactgaatg tggagtcact ttactctttg acttttactt gaattaatgt    23100
agttttaagc catgcatctt taataagaaa ctgacttctt tatcggatta gggatttaaa    23160
aggatctctt tgtacccagt tgggaaatga gaggttgtca catgcacatc ctactctatt    23220
agttccacta tttccatgcc ctgttccctc tgcacaagag gaatgagcac atgtttctaa    23280
ggtttattct tcaacagcaa agcaaagttc ttattcaccc ttcaataggc tcttcatgaa    23340
agtggacagg ctgttgagtc accagagacc aaggaagata ttcattattt tggatcttga    23400
gcttgacctg gaattcctgt aacccagtca ctaagaaagt ataatgtgtg gtaaacagca    23460
aagattctac aatcagatgg gctccctta aaactcagtt cagccacttt tagttattaa     23520
ccttgagcaa agctcccgtc tctctttgct ttagtttctt catctgtaaa acagggaaca    23580
tatttgtgcc ataaaattaa tgagaattaa atgagctaat aggtataaag tcatcagaac    23640
attacttgaa acagggcaag cactcagatg atagcaacta ttaaaatcat aaaacactta    23700
tattctagga aatccagcat gtgctaggta cgtggagctc atcatgtaaa gattattcag    23760
```

```
caggagtaat tccaacatac agtagttgaa tgtgcgcaat gtgttagact ttgggataat    23820
ggagacacag tgcctgctta tgaggcacta cagtctattt tacagggtta ttggcattaa    23880
atttgcttgc ctaatatgtt tagcttactg aattgaattc ctgttgactt acaggaggat    23940
gttgacaagg cagtgaaggc cgcaagacag gctttcaga ttggatcccc gtggcgtact     24000
atggatgctt ccgagagggg gcgactatta tacaagttgg ctgatttaat cgaaagagat    24060
cgtctgctgc tggcggtgag tattatccaa gctggatggg tagctagagc tctcaaaagc    24120
attcagcgtt tgaaatggca agttgttttg attttaggga tcactatatg ctctctacaa    24180
acaaaatgaa aacatttttt gtcccaatga ataggcccct taacattgaa ctattctcaa    24240
atagtaatct gcatttcaat tctggatgat gttaatttct gctcccataa tagattctac    24300
ggtctaaact ttagcaaacc caagttaaac caaattttag aaatttcttt accttaaaac    24360
ttctcagagg tttcaataag atcacatgaa gtttgagtct cctagaatga tatattaggt    24420
ttattcaagc atttgaccac tgagctcttt tgatggaaaa actcaagttt gttaagggtg    24480
cccaaaatat ttctctaaaa taaatcttat ttctcattag tctagctcgc taagatattt    24540
aataaatggc tactttttt cttcctgaaa tgtgtctgtt cacaagggtc ataattaaat     24600
gatgttcttt ttacagatga aagaggcaaa aaataaaaaa aaatccaatt attaatgtgg    24660
tttatcaaaa tcatgttttt atgaatacta tttttgtttg tttatgtttt agcagttaga    24720
tgagtcagag cataatatag ttgggggagg gtatttcctt gttctgttg tctcaattgg     24780 gcattatgat gaagccaatt taacataaac caataccaag atcaggtttc aagcaaattt    24840
catctttaga atctgaaagt ggcagtaaca aagaagtcta catttttaaa aaatcaacat    24900
tagcatgtat ggttaatagc aagtatggtt aatcaaagga ccatttatta ctcaaatatt    24960
caacataatt tgaaatacac aaaaattcag aacgagcagc tatgtgcaat aaaactatag    25020
taataaaaat gacctgtagg aagaaagcag aaaatgctaa aacttggctt ttctcaatta    25080
tctgatttgt tgactgcctg tcagcataag atcctataga gagaaaagta caggcataca    25140
aaagtcacat ttggttaaat tttgacatga tagagagtgt agtacagaaa caaatagctt    25200
taacagttca tcacctgtgc atttctgcca ggtaaccacc ccagcagaat attagatctc    25260
aaagagctta aggtcctgct taagaagaga agccaaaggg gagataggtc atcttataat    25320
ggttagggca catgactaga aaatgttgaa ctttacctga ccattaaaac ggcaattatg    25380
acaataatgg caacactggt agtttcctaa ttaaaattct gctgaaggaa attcatggat    25440
gaaaaatcca ggcattactt aagtttgtgt gagtagactg tgtatatcca gatggaatgt    25500
aaaaattaaa aatgattact gagccatcat taatagtcac tgacactaag ttgtcaccca    25560
cagttgatta caaaataaga gaaaccttgt tggaattctg ataggactta gaagactagg    25620
tttcattctc agatgttatg tgtatatcaa attgtgaccg attcctagaa agctggttag    25680
caggagaaca tcaaaatgag atagaaagag cactgggggtt tagaaatcag aatctcacta    25740 cccttttgtgc ccagatcttg ctatttgacc taaaggaagt catttaact cttaaaaagt      25800 ggaggttaga caagatgaca agatttcttc tatttcaaaa attccctagc acatgattgc    25860 tgaaatatt tactacatat ttttaatcta aaacttttat ggaattttag atttggtgtt      25920
tgacatgttt ttcagacaat ggagtcaatg aatggtggaa aactctattc caatgcatat    25980
ctgaatgatt tagcaggctg catcaaaaca ttgcgctact gtgcaggttg ggctgacaag    26040
atccagggcc gtacaatacc aattggtaag tatcttgag aaaccactaa tggtgaggat     26100
aggagcgagg agtttactat agagctgaat aatttcaaac tctcccttttt aaagatgtca    26160
```

```
accaaataag gcaaaattat tttcctcttg actttgagac aacacagttt tcaacttaga   26220
agttctatta aaattcataa aaggtctttt aaagttgttt cagcataatc atgaagataa   26280
cattatagat attttagaaa atgtcaaagt aagaacattc ctttggcagt aattactgat   26340
ctgaggcaat tgcctctcta aggtcccaaa cttttttaaag ctgacctctg aaattatttta  26400 tttgggtttt attccaatac tgacatttat atcctttctg taatgtaatt atttaagcct   26460
ctttacatgt tccagtataa gtcagttatg gtcatctgtg cctggtcaaa ctcagtgtag   26520
ttagaccaga ctaatcaaac aagccagttc acacggactc gtttcaaata tcttcaaagc   26580
aagatgggac tgtgtttgca gcctaagtta aggggtttgtg tgtgtgaatc tgtacgtatg  26640
tgttatttta gtggggtatg cacataatgg agtagaaata ctaaagatat ttcatgtgaa   26700
acatgaaaac acacacattt aggaaacagt atgggtggaa tttaattcag gcaaacctat   26760
gaactttagg aatacaatac cctccaggac tggccctgat gtgcacttcc aatccaattg   26820
gagcatgcag gaggtcagaa gtgatagcag aaagttgaga ggagagtaag acctcggtgg   26880
tactaagaaa tgtggctact ttagaactgt cctactttac tccgggacaa aatgggagaa   26940
gtcacttaaa acacaaatag atcttgatga agagagtcct tgctgaaacc aggaagcttc   27000
tgtgggaact agaacagaat tgaatgtaaa gcataatgta tctctctgga tgaccacatt   27060
aaacttcggg gcacataaat tggtcaaatt tagattgaaa ataaatgtct tatactcctg   27120
tcattttctt catgtattta gagaatttgc tattattgtt tggtaggcaa ataaaataca   27180
ttttagaaca agtcagtagg aaaggcttat tactcatagg gagattttct ttttaattct   27240
actgttttta attttactat ttctaaaaat tatattataa cttttaaaaa gaattctctt   27300
attggtagaa ctttgagcta ccagaaacaa attggaatgt ggttcttctc ttcgccagag   27360
acctcctact tcctttctcg tcccttttt ataacactta gagaataaag ataattttca   27420
aatcaggcct cctagaagat gaaaggtgga attaattatc tttcagattt ttgccaattt   27480
tgcctctttg atttcaccta actcaatttt atggttccta tcatttcgaa ttactatttt   27540
agggcttcac ttaccatttt gggaatagtt ggagatatag atggtctcga tctcttgacc   27600
tcgtgatctg cctgcctcgg cctcccaaag tgctgggatt acaggcgtga gccaccacac   27660
ctggccagat atatgttttt aaaattattg tctacacctt tctctcacat caccaaccac   27720
cattttgtga atgtcaaata catttgttta tatatgattg tgtgtgtttt attttcaga   27780 tggaaatttt tttacatata caagacatga acctattggt gtatgtggcc aaatcattcc   27840
tgtaagcttt tctcctatat aattctcaat tttaaaaaga agagttctta ttctatctaa   27900
tgatgaagct ttctctaaaa cagatggatg cttatgtatt tgttaaatgt ggagtaaatg   27960
taagatttgt tgaacttggt ctccctgtga ctaaacttct tgcatatgaa ttaggtagtc   28020
cgaaaaccta tctatattct ggcatatctc ttgagaatgt tttaatacta catcatccat   28080
aaatgttaac cctttactct atgggttgtt ttattaaaag ttgtattatg tactctttat   28140
aagagccaag ctttacatgt atatggcaag gtgctctcca ctgcacatct gcaggatagc   28200
attttggtgg aatgtagtgg ggcctactat tctccaacgc actttctcat tgagacatct   28260
catcatgcag aacagtagct cccagagtgt tcaactcatg acacacattt tttaatcaaa   28320
atggaaaaaa gaataccaga ggcatttgaa gcactgcatg aatatatttt tacctttaga   28380
taagaggctc agatcctcca tattactctt agaggaaagt agccttttta agaggattgt   28440
gaagattttt taagcccaac aaacaggaca ctatctaaat gatttatttt taactgacat   28500
```

```
gctttaaaag gccaaacaaa aaaatggtag cgaagtcctt atgtgaagaa atggtcaaga    28560
cttatctttg gctccaatga gattgaaata tattcatatc aatattttag tgaaattgct    28620
tattaattca aaagtcccaa taaatcgata aaaactatat aattatgaac actgataata    28680
gctgatatgt actacttgtc tatgctagac cagtcattgt gttgagcccc tggccctctt    28740
tcttggttaa tgctcaagac agccttctga ggcagagagg actattatca gcactcacag    28800
attatgaaat cagatacaga gagcacgtaa cctgtgtgag ttcacatggc tggtcagtga    28860
ttgagctgag atttgaaccc aagtacttgg cctctggacc ctggacatct ttgtctttag    28920
caaggtattt ttcctggaaa taaaagctac taaataatat tattgggtaa ataattacaa    28980
taaatgactt atggagaagg agagtaatca tcctttttaa acattttttag ataacttaca    29040
gtgtgctcca taataagcca aaccatgcag tgattttttt tttcctggta gaaaaagaac    29100
tcaacagtac ttgattaaat tttgaggttc tctcctattt ccttctcata tctcatatct    29160
ggtttattca gagcgtttta gcatttacta gttgctttta gcaatgaagt ataatatgcc    29220
agatgatttc acaaaactac gcaattatta cataacatct acaggggtg tataatatgg     29280
aagttggatt agcaaatatg cctttttgcaa tacaaagaat ctattgttac atattgcttt    29340
ctagtggaat ttcccgttgg ttatgctcat ttggaagata gggcctgcac tgagctgtgg    29400
aaacacagtg gttgtcaaac cagcagagca aactcctctc actgctctcc acgtggcatc    29460
tttaataaaa gaggtaagtc tcccgaaatc aaaatatgct caagaactca agaatcctaa    29520
attacaatag gaagacctca tttgttgcta ctataaagta cattatttac agatggctcc    29580
tgtccagtgg ggggaataca tttagcatga cggctggctg caatttctgg cagtcacccc    29640
aaattcatct ctgcccaaat gcagacagga agccaaacac aaaggtttgg tgtcaaacag    29700
tcaacttggg atcacatttt tgcttctttg tccaactctc atgaacataa attcatgttg    29760
aaattaatgt agcattcttt caaatgttga acattaagt tggtttgtac ctgccactga    29820
tggcctagtg ttttctgcaa aattgtgtaa actaatctat gtaaggttga aagggcctct    29880
atgccaatat gcttgtttgt aatattgggc cacattattt ccaaacactt tcaatctac     29940
tcatgagtgg atatgtttat attcagtttt ctattatgag ttcctctgca tttatcttcc    30000
tgttcaaaaa cagtaaaaga acatgtaaaa cattttcatc agctatctag attgtgttaa    30060
tatacttgca aacaattcat tgtccttttt tcttcatctt accaaatctt aaaaaataaa    30120
tgttaatcac tagaaactta agttacaaa actgaactta tcttttaaag atattattta     30180
ttgaaattaa aaacagggaa aagagatgtc aaaatgaaac atttcgatgc aaataacatg    30240
aaattgtaat gtgcccaact cagttcccat gccttcacct gaattcttta atgaagattg    30300
aaatcaacct gtgatgttga atcatgaatg ggatgacagt atttacttaa caatttacta    30360
agtaatgcca atgggaattt gcaactcagc agttatgccc tcaacaatca acaacagcta    30420
ggaactaaaa aatgttagat cccttcagct tcttattttt gctgatggga ataataaaca    30480
tgttacttac tttctacata agtaacttac caaacacttt tttacataca atcttttga     30540
gttagcatta tgaaatttga aagagccatc actggagcaa tgattcatag agtatggact    30600
taccctgaca agaaattgtc ctttaataat gcaacccttg aagttattct cttatgtgtg    30660
cttagaaatg acataataag actaaagaat agagccagtt gggtgaatta ttttttttcta   30720
gagcatctca taaggttggc attaagagac aatctcaatc ccctactctc ctcctttttg    30780
aattaaattc ttatactgta acttttaaac ttttatcttt ttaggcaggg tttcctcctg    30840
gagtagtgaa tattgttcct ggttatgggc ctacagcagg ggcagccatt tcttctcaca    30900
```

```
tggatataga caaagtagcc ttcacaggat caacagaggt aatattattt actcagggca  30960
aaagttaaga atgtctgcat tgccagctat gaagtatgtt ttatgtaact atttttgagc  31020
caacaatttt aaaacaaaaa ctcttttttaa tgatttgtta cttattttag ccttcaaaca  31080 tatgatataga atataagcag atgtagtttg aatgacatga tgcacctatt ttaaatcaga  31140
atgagagtaa actattttta gtatgttcat tactttctct gacgagaaat atggctgctg  31200
agaccttgtc atattattag gaagatttat aatagaaaat taggccatag tgatttgtat  31260
gaatgaatat gattttatcc tataggttat gaaaattaaa tagtagagtc tcacccttttg  31320 caccttattt ggggttgtct ttctcctgga cactgtgaaa gagagccaga aactcagctt  31380
ccctcagtgg tacctagact aacttttctg cctctctggc ttgaacttga ccatcctaaa  31440
ggttaaagaa aaagacccca accacaaagg agaagtggcg ggcaggaggg agagcagact  31500
agaaggtgaa gtttgggaaa atagatcccc atttattgat gatgttctat cctaagcaaa  31560
agaaagtggt ggaagcatac tgtaccatgc aaaaaaaatt attgagtcat tctattaaat  31620
tacgtgactt tgttagatgc tcagtgcaaa aatgttattc attggtacac agtatagaca  31680
gtgaagagtg agcttcactc catcttagaa agctgctgac aacaagagac caggcagggt  31740
gtgataaggt actaaggcat gtacaaaatg ctgtaaaaaa ggttcacaag aaggaatgat  31800
gatgtccaaa tgggtactag aactagctct gggttttgag gaattgttac ttttttaact  31860
tcctggaagt tgagaagcaa aaaagacatt ccagatagtg tggtgagcat aatttgatta  31920
ttttataatc ttaattattt actccagaat aaaggcaaat ttacatagca aaaagaaatg  31980
gtggaaaatc aaactttatt tttcttggtc tttttaaaat gaagtaaata aatatatata  32040
tgtcttcttt gttttttcaca gacgtagagt aaaaaaagtt tgcattctgc aactccctaa  32100
ttgagatagg gaaaagcaaa ccccacagtc aagatttatt gtagacagaa caagtgggaa  32160
tgttcaagat atggcaatac atttaaaaat ggtgacacca caggttgaaa tcataccaga  32220
ggaataaagg tgaaaattcc tcagcctaga attctagacc ctccccaata gggaatccat  32280
gtacctgttg aggtctgtcc aacccatggc cagggatggc tttgaatgta gcccgacaca  32340 ttttttttttc attctcatca gctatcttta ctgttagtgt atttttttgtg tggcccaaga  32400 caattcttct tcccatgtag cccagggaag ccaaaagatt gaacaaccct ggtctagatc  32460
ctatgcctac tccttctcca ggtcatctgg accaggagct actgtttgct gatctcatct  32520
tcagcatcag tttgtcttcg ctcatccatg atcccctata acattggggg agcactttac  32580
ctacttaaaa aaatccctgg agattaaaag tctagaaaat atcttggttt aaattctgac  32640
tctacccctc ctagcagtgt gtctttaaaa agttaagtag ccttactaaa tttgagtttc  32700
ttcatttgta aaatggagat gagatcaaat ttactgagtt gtacagaata caattaaatg  32760
agctaatgag tagtaaaaca tttatcaccc tactgagcgc tcagtacatg ccatatttcc  32820
tctttcctcc catactttttt aatttcgcac actagtttac acaatgtgag aaaaaagctt  32880
cctgtcccaa tatttctttt tctccatctc tgccactctg ccccatctct tcctgattat  32940
tccatgtatc tttttcattcc cccaggcttt tagttcatcc ttggccataa cctactctaa  33000
acttgctccc acacgttccc tctctggctt tctccttgcc tctacagtcc caggagcaga  33060
gcagcctaaa ttttaaaaca ccccatctga gttcccattg tccaccacat ataataacag  33120
tgcatgccta ttgccttatg tgtctctctc tcttgctgat tatcctcaaa gacagtctta  33180
ttcattgtta tctccagaaa ccatcacagt aagaaattct aaataagtat taagaaatta  33240
```

```
aatgtgatat cacactctgg ggactgtggt ggggtcgggg gagggggggag ggatagcatt    33300 gggagatata cctaatgcta gatgacacat tagtgggtgc agcgcaccag catggcacat    33360
gtatacatat gtaactaacc tgcacaatgt gcacatgtac cctaaaactt agagtataat    33420
taaaaaaaaa aaaatgaaaa aaaaaaaaaa aaagaattaa atgtgaataa cacgatttta    33480
ggagccacaa aacccatcct actttcaact cctgaaactt agttccatac tccctggaac    33540
ttctttctgg attttctttt agcttcacat ttgttgcttg gcagatatta aggaacttga    33600
taaatgtcat gaaagaggca aacaatagac tgtatccttt gtgttcattg tagcaaagac    33660
cctccattct aacaacactt taggcaaggt aagaatttt ttttttttttt tttttttgaga    33720 ggagtcgtgc actgtcaccc aggctggagt gcagtggcgt gatcttggct caagctccac    33780
ctccgtggtt catgccattc tcctgcctca gcctcccgag tagctgggac tacaggcgcc    33840
caccaccacg cccagctaat tttttgtact tttagtagag ttggggttttc accgtgttag    33900 ccaggatggt ctcgatctct tgacctcatg atctgcccgc ctcagcctcc cagagtgctg    33960
ggattacagg cgtgagccac cgcaatatcc cattagattc atataaaata gaactctacc    34020
cacattatgc aagacataat aagctagacc attttcatgg gcatttgcta cttctgctcc    34080
acatggcaat gccacagtat catggaatac actgtttagc catagtctta atagttctta    34140
tcttttcttc attgcatact cctttgagaa aaatgataaa cgtttacttt tctccaaata    34200
agggaatgaa atcatgagac aaaaattaat gtctctttgt tttgactta gctagctttt      34260 tgggaaaact caagcctttt atttgccatc taaacttgtg ctaagcaaaa gtgtagactt    34320
tctttctcat tcatacttct aaccattctt catcctagtt cttttgacgt ttgtagcttt    34380
tacaaaaata tatttgattt tattaccttc tccaaggcaa aagttatcta ctttaatgga    34440
gttacttccg taaacctaaa ttaaacaaat aaaaaaaatt cagaaagaat ttagagaaat    34500
caaagggtga caggtaagta aatttttat ctacaaaatt aaaaactcct taacatctta      34560
aatgaaaatt cagtttctga aagtggtcat aagaagtgtg ttatagaatg gcatataaga    34620
gaaatttcag acaggatttc cctagtgcaa atctccttt aatttattttt ttattaatct      34680 tttaggggtt tgatttagaa acataaaata tttaaatagg aggaaaacat tagcatatta    34740
atgccctatt ctgtaattca cagtagcagt tagttcagta accacataaa atctaaacat    34800
acactcacga aacatctatt tctctcttgt tcagttggga tagaaacttt ttattaaaat    34860
ctgacatgca gagtaaaaaa aagaaaccta gaaaataaaa gaagcaaaat agtgaattgc    34920
ctttaaaaaa gaaaggcaaa gaacatgttg gtggattaag gctgccatac aaataataaa    34980
aaagaaataa ttgtagaacc agccaagttt ttagagatag aaaaaccaga aacaactata    35040
gtaaataatc ttgatgggaa gtgatccaca aaggaaaaaa taattgaaaa caaagtcttc    35100
ctctgaaaag ggcaaactag cattaaagaa gaaaccagaa ctgtaggatt ccagctaact    35160
gaagtagctg cacagatccc attctttca tccagttcca ctgttcaaag gtgtgtgtgt      35220
tgggtgggaa gacagagaaa gaaagagata gagagacgac tgtcaatccg caattaaatg    35280
agccttctgt catagatact aatgaggaga ggtatgcagt gatacgttat tgttactgct    35340
accacagagt taacaatcta tttgggaaat gtatttctat acaaataata caatctggat    35400
cagactctga aggagacttc atgaggtttt ttgggagact agaaaagaa atggtcctgt      35460 catttcttct agcatctgac ctagtgtcat cagagaagga tttaaggaga agctaagata    35520
tgagctggac ccctaagaaa aatagaactt gaaggcagtc caggttgggg tggacaaata    35580
atgagaagaa ggatgagatt caagaggtag tgaatatgtc agtttgactg gatagagtta    35640
```

```
tctggatgcc agaagaggga taaaaaatga aatagctaag ttgcgactgg gtcatgataa    35700
gtctgatcaa tctgtagaaa gatgatattc tgattaaaat taaaaataac ctccgtagcc    35760
atcaatatca cttatccgtg ttctatatct ctgctttctt gctgatgaaa atcagcatt     35820 tttctgattc cttttatgtc tgtatgcttg gatgagggag ctttacatat ctaaaagtgc    35880
cagatcttta aaaatgccat ttgccagaga atcacttgaa cccgggaggc ggaggttgca    35940
gtgagccgag attgcgccac tgcactccag cccagtcgac agtgtgagac ttcgtctcaa    36000 aaaaaaagc catttggtgt ttctcccaaa tgaaatttta ctgtggcaca aacatcacat     36060
aaatttagaa tgctaaagca acctgtgttc atgagagcag ggtaagcctc ctcctttgta    36120
atgctccctt tcaggttggc aagttgatca agaagctgc cgggaaaagc aatctgaaga     36180
gggtgaccct ggagcttgga ggaaagagcc cttgcattgt gttagctgat gccgactgtg    36240
agtagaaacc actttgttaa cttttcgtcc ttcatcgttt ttggtgtctg ataatgccaa    36300
aagtgaactt gaactttaca aaaaaaaaa aaaaaaaaa aaagcatttg cttctaacat      36360
caaagtgtaa agagtccaaa attactcttg aaaatctctt aaatcatcct aaagttataa    36420
cacatagata atagacacaa tttcttcctc gtttagaata gattgctatt tcctcagctg    36480
aaccctagat gatgtaaaca ttttgcattt aaatgccatg gtgtattttt taaattccat    36540
atctgtgatt attagcattt cattgagcta atgagatact ccagaatggg acttggattg    36600
agaccaactg aggagacagc agtttcacat ttgccctctc ccttcactct gggtcataca    36660
ctcattaaat gaaatgatca gaagaaaatt atacctaata tttaaatatt ttttcctagc    36720
aagtatagtg gagtttatgt acattaaacc tacaaatttg ataaccccc actatataat     36780 attttaggtt cattctgatt atattaccaa gtagaatttc ccaattattt cctaaataga    36840
agttaattag cagaaatgca tggtcaaaca ttcttttttc tttcacaact gcattatctg    36900
ttagaggctg taaatacaaa tggttcatgg aattagccta tgttgctgtt ttgatcttaa    36960
ttgaagtatt ttagaacaca ctaccttatg aaatattcta taaacatgaa agatttctaa    37020
ttttactaag actgtctata aactgcttct gctacaactt aagcagatgt aattagttca    37080
caaaataaat aataatcata cccagttgct ataacattga attgaatctt cagcatttag    37140
aaaattaaaa tgcaaagaaa attttattct tgtttagagt ctactaagga agcaacctat    37200
ttcttccttt taatgcacat tttatcgcct aaaataaata agagtttata ggcacatatg    37260
aaataatacg gtatacttta gatagatttt gaaaatgtct ttgatggaat aaaatcataa    37320
ggtgagtgag tgattctgag tattagtgtt ttttgttact ttttagttgt ttttgtttta    37380
ttttgttttt ctttcccaca aagatcacat ttcctgttga gtagagtatt taagaatctt    37440
ttgaaattat ttaattcgat agacatgtca ggtttttttt attatctgtt taaaatctgg    37500
ggcctgaaag aaataatcac aatcatctaa ttatataatt ggagatattt atataaatca    37560
tttccaaaga gatttggtct catgatcaaa tctacattct tggtgatgtc catattaaag    37620
ttgtaatagt aaccactatt ttttcagatt ctgtatgttt ctatttttc catggtaaat     37680 gcaggatcag aaagattaat ttgccacctg gctggtagga ggtaaactat actgagccca    37740
tgtctgacta cacaactcat aattttctt tatctccatg ttgcctctga gaaacatata     37800
aaatatataa ttttataaa atatatcttt aatgtgaatg tcttcttcgc agtggacaat     37860
gctgttgaat ttgcacacca tggggtattc taccaccagg gccagtgttg tatagccgca    37920
tccaggattt ttgtggaaga atcaatttat gatgagtttg ttcgaaggag tgttgagcgg    37980
```

```
gctaagaagt atatccttgg aaatcctctg accccaggag tcactcaagg ccctcaggta    38040
agtataaaat agaaaggata gcattttcag ggcacaggaa taaagtatcc tctttagacc    38100
tagattttat tgagtaagat tacttcccat ctgcacacct tcctaggtga caatgctgtg    38160
ccagtttggt gtttaaaagc aatctaactc ccagtgagaa tgaaatcatc ctgttttgt     38220 gttgcccagt tttcatgtct agaaacagtt taccggccat gctgagaatt aaagacatga    38280
ggaaaaataa caaatgttct acatttttgg ctttcctcaa tctgcacacc tcttgattcc    38340
tatatacagt tctctgtcca ctttgaaatt cttatacatt cctaccattt tttcctcctg    38400
aatccttcat ctccacagcc atcccacagt tataaccagc actcccctaa atcctctgca    38460
agtcatcggt tactctgacc ccctaatcgt agcatggggt cctaaaatgt cctgagtttc    38520
ctttgcggca aacttcgtat ttcagttgtt aaagcccaat tattcccta ggcactcagt     38580 tttctttgta gactttatta tcagtaaagg tctctctctc tcttatccaa agatcatctt    38640
tccctcttcc ttgcatagtt ctctgttcat tgtttgttta agcttctgga tctttggttg    38700
tgaatttctt cctgcccttt gggtcttgtt ctagagcagt gattctaaac tggggcaatt    38760
ttgctcccct cacccggggg acatttggca atgtctaggg atattttaag ttgtcactac    38820
cttggtgaga agcggtggct ctacaggcat ctagtgagta gaggccagag atgctgctaa    38880
acatcttgca gtgaccagga cagccccatg acaaagaatt atctggccca aaatgccaac    38940
aggacaactg ccgagaaatc ctgctctgga gtctagacat taagcttaga ggctctgttc    39000
tttcacaata aaggttttac actgatgcgt gctgtcaatt tgaaaccaaa cgctattctt    39060
gactcattca ctaagccaaa agtaaattca attaactaaa agttagtgaa cgttgctatc    39120
agctaaaact tgagatgggt acctggcaat gccaaaaaga acaaagagga cttgatcccg    39180
gacctcatgg agtttacagt ccaagtaagt tggacagtct tggattttcc tgttcatctc    39240
aagacatcca agtaggaaaa tcttaggact taggcagtgt aacatattga aatctaaagg    39300
ccctaaaata agcggcaagt gaggtaatac tttgtttat cttaatccca ttatattttg      39360
tatttgtctt tgagtttaat gagtacttaa aagtagttgc ccttttttc atatttggta     39420 tatggatgcc aagagatata ttcaaatcag ttttgacttg gtctcccatt tcaaaaaaga    39480
atggaattct atgttttttt gttgtgatta tttatctatc taactaaaag tgaagcactt    39540
ttcttatttt gttgatggat tgatggatga ttgattgata gatctgaaga gaggagagaa    39600
tacctaagat acctaatgcc taattgttgg gcagtacttt cctccattag gacatcttca    39660
caattcaacc aaaagactcaa aaattgagct ggaataccct attgatttta agataaggaa    39720
gttaaaatag acttaaaaat tcctatttgt aagattctaa agtaaataat ccagtgatct    39780
agaatttagt ttctataaat gaatagaatc cagtgatctg attaatataa gaatttagtt    39840
tctataagtg aatagatttt tatcacaagt tccattgagt cagtaggata agtaggtatg    39900
ttagaatttg gagaaacaaa agactaaaaa gccctgggct cctttaccat taaatattca    39960
tctattgtta ggagaaaaaa cttacgcaaa ggggatactc actcactaag ctttagccta    40020
ttgcctcatc caggggtggt tgagtgaact gaggctttta aatacaatga tggaatcttc    40080
ctcattaaat ataacatcaa aaaggttata gaaaaaataa tggtcaaaac gatttgtttt    40140
aggggaaaaa attaaagttt aaaaaaattt gaacattaca aattatttgg gggttagagc    40200
aattacaaaa tatatatata tatatacttt gcatatttgt attatatctg tggattcatg    40260
tgtgtatctt tttcatattt caagtgattt tcctatttga ctttatagaa aaatatata     40320 ttgtcttaaa cttggaaaaa ttagtatttt catttgaaac agaaattgtg atagccacat    40380
```

```
aaacgatact aaaattatca cagagtagca ccttataata gtgtggaaag atggactttg   40440
gagttacagt tatataggat ttaaactgga tttaaaatcc agcctccctg aaactattgt   40500
cttatgtgta gaatgtgcat agaaacctca atcttgaaga ataattctgc agtgcaattg   40560
gataatctat aaaatgtatc catcagagtg cttggtccac atgctcaaat gtctagtaaa   40620
taaataaaaa ttacatgctt ccatttatac ccatggtgac aattatcata cagatcaatt   40680
acttctatat ctattcattg cttttgttga tacatggttt ctgaataatt tgagaacatg   40740
taagtgcttt ttcccaattc atcttcttta acccattaag cctaaggaat caaagaattt   40800
acccattcaa acaccttaaa atgtttcctt tgagactgtt accatatcat gacctaccta   40860
atacatttca tagactagcc cataggccaa tggcccatca catgaaagag ccccagctac   40920
atcctagcat tattggacag tcccaggtgt ccagaaagaa ggtcaagttt atatatggtc   40980
agcctgatgc cttctgaaga aggtctgtat ttgtggtgaa tcaaaattag ccagacaaaa   41040
ctgaccagtc tctaagtaga gcctaatttt ttgtttgtag tcccaagctc caccacagtg   41100
ttcctcaatc tttcccgtgc ccggggattc agtagatctg aggtggggtc aaagaagcac   41160
atttggctac caagtgatgc cacaactgct ggttgtagga ccacattgtc ggtagcaagg   41220
cactgaaata caaaggcctg tagttttata agttagcgac catctaagtt ttccaacaaa   41280
taaggctttt cagccctttt ctccagtatg tatgcaggga tttgattggc actggttatt   41340
caacgtggtc acagacagga aaacatgact tgggaaatac atcttgaaat aaaaaccaga   41400
tatcatgatg ttgagggcat agtcagatta atatgttcca ataagacaga aagctttatg   41460
tggagtgaca tggacccttg actatttatt gagaaactag aataccttac ccaggcagaa   41520
tttatctcac cccacccctt agtctgctac tattcaacct atgtagtaat ttaaatattt   41580
cttcttaaca ctattttttt cttaatctgc tggaaatgaa ggaatatttt ccttctggga   41640
tattatatta aatattgcac taaagactgt tgagcaacat tgtaccaaat attgtgccaa   41700
attttagaaa atagtttcta gtttcaaata gtgcttaatc tagttagata tgggggctga   41760
gctgtattca gttagaaata actttatgga agcttttttct tggctttgga agataaagaa   41820
gatttgcaga gtcagagaag agtaagagaa agtgaaacat aaaaactttc aagtagtggg   41880
aagttaaacc tacaagagct tccaccctcc aacccatctt agctcctaga tctcctgttt   41940
ttcctttaat ccttaaccccc tgctacacct gagataggca gccctcaccg gttacttgga   42000
atccaagagt cacccagtta ttcaatgtca caaatagaa attgagacaa aaattagccc   42060
cagatttcag tgcttgaaga ggtacgtgtt cctggtgttc acaaccagaa ctccaaactc   42120
atttattttc cttataaaaa tagtgtttaa ataaagacga tttaagttct gtaatacttg   42180
gcacatagtt agatgtggct catttaatga agcaggatgg tgacattcag gacaggccag   42240
aaattggaag cagatttact gactgcccca gtgggaccag aactgggaag ggtgcgcaga   42300
ctatggtcag aatgggatat ccaagggcat cggacaggtc agagtgggtg attcagaaat   42360
ggggagatca acagaggct cgggagtctt ctaagaacag tcttaaagca tctgcttccc   42420
aacagatcta attaaactca gtatcaaagt tcttttttc tcttttcct cctttcattt   42480 cagccgggac aatagtttcc aggtaaatgt atttagatta acaggcattt cttccagagt   42540
gaataaatga tgattgtcat ttatgtgttt tttatgtgtt tgcagtgctg aatgctttcc   42600
tatataacta taaaacaaat gttaaataca aatatctgtc ttcaagagat ttccccctaa   42660
aagtcatgag aagaaaatat atccaaagaa tgaatctgaa cctctgttag ctgtttcgat   42720
```

-continued

```
tcaatatttg gtttaattgc aatattttag cattttgaag cccttgttaa caggcccagc   42780
aatgtgttat ctttacaagt gactacttttt tttcttttca tgtgatattt ttcaaataga   42840
ttgacaagga acaatatgat aaaatacttg acctcattga gagtgggaag aaagaagggg   42900
ccaaactgga atgtggagga ggcccgtggg ggaataaagg ctactttgtc cagcccacag   42960
tgttctctaa tgttacagat gagatgcgca ttgccaaaga ggaggtaaat ggcttcattc   43020
tgttctgttc ttttttgttgc catgttttgt ctgtttgtgt gtatacaaag tgtcactttta   43080 aaattcccag ctcttttggaa catctttccc tctaaacctt actcttatt ctgttcttga    43140 tagaggttta agttatttgt gatagatact aaaaagtagt aagggatcca tggggccagc   43200
cacaaatgtt cagccaacac agatctggat gcttaacaat tttcaggtgc tgccttcaca   43260
gctttaaaac aatggaaaag aatcctgtca tttgcagcaa caacctggaa aatttatgct   43320
ccatgaaata tgacaggcat aaaaagacaa ataccgcagg atctcacttt tatgtgggat   43380
ctcaaagagt agaactcata gaagcagaga ttggaatggt ggttaccagg ggcttggggg   43440
agtggaggat gagggttggg aaatgttggt caaaggattc aaactttcaa ttaggaggag   43500
taagttcaag agagctatcg taaatatcct gactgtaatt aataacaatg tattgtatac   43560
ttgaatattg ctaagagagt caattttaag tgttctcacc acaaaagaga taaatatata   43620
ggttctactt tctggttcca cctttgccct atagactctt tctatataac agccatccat   43680
gtatttgaaa acagcattca tcccctctat cactccctac cttctatgtg ctcttagtcc   43740
tatttgtttc agctgttaga cttcctgatt ttgtatattg cagttaagtg tttggtgagt   43800
gtatatatgt gtgtctgtat acatatataa tgtgtatata cattatatat atgctcacca   43860
agtatttaac tacaatatac aaaattagaa aaaaatgag ctgtcattct tgcatatctt   43920
gattaatacc agataagacg tggaaaaaaa tcttcaatta aggaaacatt tattgtgttc   43980
ctataatata ttaatatata gtagaacagc tagcttgcta cttcaaagta ggagcctgga   44040
gctatgtgct gtgttcaatt aaaattatgt aaaatatgaa cacatttatt agagtagctg   44100
ctgtgtatat ggttcctatg ttcaaatagg attagattta taacgttaag attcacactc   44160
aacctctatt gaacagcagc ccctccctttc taacatttaa atcagtggtg aacaccagaa   44220
aactctttgt catttctgat ttttgtcttc cttcattcag atttcccaga aaattctggt   44280
aatttcagga atctttatct gatcttaata aatattttat tgaaatgcag agcttaatt   44340 ttaaagagaa aatccagttg tctttctttt acctgaggct gagatacagg gtgaattgag   44400
tttgggctgc agtaaccagg aacttagtga aagcaaaaga gtactttacg ttagaataag   44460
caaattgtga ttttttgtttt ctgtcctgca attatagcca ttaccaatga actcatgctt   44520
tgattagaat aggatggttt agaatgtata agctcttgca gtaaggaaca attctgtttg   44580
atatatttaa gttgcctaag atttttgctac agagtagact aaaagttcgt gatgtttacc   44640
taacttggct aattatgaaa agtaattagt aactattcta ctgagtacag tagaatagtt   44700
aatattttac caatggcata caggtattta aagcattatt attatcaatc attgcctatt   44760
catttatcca gcagattatc attgcctatt catttatcca gtagattgct ttctgggact   44820
tgttactatg tgtagtgact tggaagataa gaaaaactag agagtgaatt taaaatattc   44880
ccaagtgaaa aagaaattct gaagttaatg atttgttgca caatcataag ttcttgaaag   44940
cttaattcca acatctagaa acttaatatt gccttaatta tttgtaccct ttcttcttcc   45000
aaaggaaatt taacacctga ccattatctg tttttcaccta ccatttttgc agttacctat   45060
ttggattctc acacataggt ttgagatgag aagaaaaatc ttaatcaatt taggatagcg   45120
```

```
tgtaggaaaa aaaatctacg atatcattta aaatatttca ttttaaccta ttatttttac   45180
ttatttattt cttgtggtat agattttggg accagtgcag caaatcatga agtttaaatc   45240
tttagatgac gtgatcaaaa gagcaaacaa tactttctat ggcttatcag caggagtgtt   45300
taccaaagac attgataaag ccataacaat ctcctctgct ctgcaggcag aacagtgtg    45360 gtaagtccaa cctaaggaat gtagccttt  cagtaataac cacattaaca gattactacc   45420
ttgaactttt tcagacttgg atttttcatt tggaattacc tatccttcta gaaaagcagt   45480
tgctgccttg aaaacaaac  aaaaggctgg gtgcggtggc tcatgcctgt aatcccagca   45540
ctttgggagg ctgaggtggg tggatcagct gactgaggtc aggagtttga gaccagcctg   45600
gccaacatgg tgaaacgcca tgtctactaa aaatacaaaa attagatggg tgtgatgcct   45660
gtaatcccag ctacatggag gatgaggcag gagaattgct tgagcctggg aggcggaggt   45720
tgcagtgagc cgagatcatg ccattgcact ctagcctcag caacaagagc aaaactccgt   45780
ctcaaaaaaa aaaaaaaaa  aaaaaagctg tattggaaga actttaggga ggatattttc    45840
tttaacttta tctagcttct tgaaattgct taccaaaaat attgtattga tgtttgatta   45900
atacaatata agaattgcca agtaatttct gagcacgtgg tactatgctg tatacaggga   45960
ggtaaaagag taagaacaat atttacttgg taccttgtg  tatgcagata ttcttatatc   46020
ggccttctta ctctaggatt attagagata attgaagtta tttttgaaag attgaattt    46080 gaagataccc tccctctccc attttgacc  tagtttatat ctcttatttt tatactttaa   46140
tcaagaggat ataaacatga agtctgtgcc tctcaaactg ttgcattctg tactcagctg   46200
tcagtctcta gactatgtct ttggtcactt tggtcccatt agcctaattt tggcccctca   46260
gtcctggaaa aagcacaaga ttattttcct tcccaacact aagtcacacc tagatcagac   46320
ctatgcaata ttctctttct ttctttcttt ctttctttct ttctttcttt ctttctttct   46380
ttctttcttt ctttctttct ttctttcttc ttttcttttct ttctttcttt ctttctttct   46440
ttctttcttt ctttcgtctc tctctctctc tttctctttc tctcttttct tttctttctt   46500
cttttttttt ttttttttt  tttttttgag ctggagtctc actctgtcac ccaggctgga   46560
gtgcaatggt gcgatcttgg atcactgcaa cctctgcctc ctgggttcaa gtgattctcc   46620
tgcctcagcc tcccaactag ctgggactac aggcatgtac caccaagccc agctaatctt   46680
tgtattttgt ttttttcttt ttttagtaga cagggttt   caccatgttg gccggactgg   46740
tctcgaactc ctgacctcaa gtgatccatc cgccttggcc tcccaaggtg ctgggattac   46800
aggcctgagc caccatgctg gcctggacct atacaatatt ctaaggctgt ggttctcagc   46860
cctggctgtt cattagaatc atctcggggg ctttaaaaat gtataaactg atttggggca   46920
ggggagggta tacattaaca caaattatat cagtgtatag tttaaatttc tcctccaaag   46980
cccatgtggc aatttaaatg ccattgtaac agcaatagga agtgggccta atgggagact   47040
cttaaataaa attcagcaag ttcttcttga atagtcggta tagctagtga tgaatataga   47100
atttgcctat gataaaagca ttaataaaat tcagcatagt tactgtgtgt atgtatatta   47160
tcgccactta ctgaagatat ttataccaag tactacaaca agaatactat tcacgcaatc   47220
ttacgcatac cttgaaacaa tcctattaaa tattatcatc cccactttac acatgaggaa   47280
acgcttgcag aagacagata acattttgaa ctcaaagttt ttgccaagtg aacatttctc   47340
agttccctgt taattcacag taaaatagtt tcatttctag ttgacagtaa aatgagcaaa   47400
tttactctct gcactttta  acaaagacaa atttcagttt tgtattttcg actagcagaa   47460
```

```
tgttccatgc ttgtttgatg aagcttgtta tgacatcacc ccactgaggg tcttgggaat  47520
ccctgatcag gaatttcctc tattatgaaa aacagagggg accatcttgt tactacatat  47580
cctagaagat aataattttc tggcattgtc ccagacctaa tagctgcttg gtgttttcag  47640
gaaaattatt gaactccaga gttgcaggaa gtttactcat aatttcaaag tagtatttga  47700
ttttgcaatt taaagggcaa ttaaacaaag ctgagacaat actgcctttt gtaagtgtaa  47760
atttattaaa ggaattatcc ctccaggatg agagacatag ttaagaactt tatggtccag  47820
tgagaatgtg gaacttcggg aactgggata gtgttttaac aaagaaaaca tctgaatatt  47880
atctcaggat aaaagtaatg accaaacctt caaagtataa tacaatttat ctggaagcca  47940
ccctggtttt ttgtttgttt gtttggttgg ttttctaaat ttgttttgta gaggcaaggg  48000
tttgctatgt tgcccaggct ggtctcaaac tcttgggctc aagtgatcct cctgcctcag  48060
tctccagcta ctaacccagg ctctggaagc cacattttg tccacttatt aaaatagcat  48120
gaagggagag aaaagtataa acataaatct cctttaaaaa gtgttttct cttgcgtata  48180 atgagaatca ggtaaataat tagattttgc taacttttgg ccaccagcaa atttaaagct  48240
aaacaaattg tttatggtct gcaaaactgc attctaattt tccccatcta gatcttctat  48300
tgtaattttt tgttggattc taattactac tattcatgta attatgtttg tttatataag  48360 catcttttaaa cacttttatga aatatgacag ggataaaatt ataattaaac ccaactcctg  48420
ccaaggcctc tgtttaagca atttatttaa ccaattaatg ggaaaaaaaa ttaactgagt  48480
aatatgatac atattacaat tgcaaaagaa aattgattct agcctgttaa gtacagaaac  48540
atcaagagaa ttacaagctg atccatatat aagcagtaat gaatactgat ccaacaaatt  48600
ctagcttcta gcaaaccata tctttccccc tacagcatag tgactattct atcttttata  48660
aattcagact accacttctc agggacacaa tgtacgacca aaatggctat ccatatatat  48720
agttgcacta ttctatttgt ttctaggtag tgtgtatcca tatatgtctg cattctaatt  48780
tatagtgcta cttttttta tcaagatgag tatgttataa tgaaattaat ggagtttgta  48840
aggagctttc caaatttcta aaactgccaa aaaggatttt ttttcacac cttaagtatt  48900 gtctataatg cacttttctt ttccttcagg gtgaattgct atggcgtggt aagtgcccag  48960
tgcccctttg gtggattcaa gatgtctgga aatggaagag aactgtaaga ttaacgttct  49020
attaagataa atatttattt ttatgaaaat gattttcatt cccagggaat taactcatag  49080
ttttcacctt acataaaacc tgcctctgtt cttttcctgga gattcatagc accaaatagc  49140
ttattaaatg tgggatgtac tccataagtg caaaaggtga ttgcagaaca gcaacataat  49200
ttactaaatt cctactatat tttagggact atattaagca acttacattg gtgattgtaa  49260
tactgcttgc ttttagaatt gcttgctata tatatgaatg taatccattt gggaaacatt  49320
tccagaaaag aggtggaaac tatgcattgg tgattgcaag aaaggtgcaa atgtaaacac  49380
tctagttatt tgaataaacc atttaaataa gtaaattagg tgacttatgt aaaggaaatt  49440
tcagtgtaag aggaatgatt cccatttgtt gagatattat tgatgtagac tttaacattt  49500
tttattacca taagaagtta ttttagtat taaaacttaa acctaaaagg aaatttgagg  49560
aaaacatgtt ttatagtagt gactagatta agaatattta tatataaatg catttatgaa  49620
atttcaattg cttttgaaac tagggtatat agacttttta agtatgcaca tatatatgta  49680
aatacagaaa gtagtggcaa tatgcttagt tgattttgtt taggcaagtt tagtcatttt  49740
atttcttaaa acttttttac atgtattaat gtaaacattt atgaagaaaa agaaatagaa  49800
aaccttatag tatcaaacac agatcgtaaa cttgctcatt ttgtaattag gaagtgaaaa  49860
```

```
tgtgcctttc tcaatctcta aatgtattaa atggttgagt accgtactct aacaaatcag   49920
caaaattaca aggaaacaaa tatctctgaa gagtcagtga aatgggagaa ttataaaatg   49980
accagtctac tttctcaata tgctttcatt tattaagcac ttgctatgtg taaggtccta   50040
ggaaccccag agacatgaca ccatgttcca tgctctacat agctgtggtg gcaggacatg   50100
caaaataacc tacatacact atgaaataag tagtaataca ctgggattcc atatcctatg   50160
gaggtagaga agcaattaaa gtaccgagca aagtattgaa gaaacctag acactaccag   50220 agtataagag tcaggatggc atctctctaa ccatcactat tttcatctgt cagacaaggc   50280
caaggattgt gagtgtggat aagagtggaa gaagaaaata gatcttttaa cctctattcc   50340
atgcttaaga ttctatagtt ctgaccccac tggaaatcca gtggttgaaa acttaatggc   50400
agtttataga gaagaaaact tctcctaaca gaagagatga aacttcctct agggcagaaa   50460
gcaagtgtag gatatcagtt agtagagaag agggctttct tgcatggaac attacatgtg   50520
gtatgttgag gggctagtga atttttgttga ttggtgtgga tttatgggga tgaaaaatat   50580
gatttcagag taacatatga tacagattaa gaagtcctgc atttaagaaa tttgacttag   50640
attttattag tggagtagtg aaaagccatg gatatattta ggatgttgct gaagtagaac   50700
aaaaagttag cccatcaaaa atgcatggcg tagctgagaa aacattactg gagtctgacc   50760
agctgaattt gattcctaat tctgccactt gctagccatg cacccagtt caagctacct   50820 aacttctgag cctctacttt tcatatttg gtggagatgt tcacattcct cttaagatgg   50880
aatgagagtt cttgtgggag ttaaatgaca tactgaatat taaatcccta gccacataac   50940
tgtcacaaag tgtaaattca acaaatgggt ttcttccttc cctagtttct tctctttcta   51000
ttactggaga atctcttggc aaaactaatt actttgtaca aaagtaaga acaaaggtta   51060 gattactctg aagggcagtt ggttcgtttc tggcctggtt atctaacaac acatttcact   51120
gagaacatta aagataaaat aatcaaaagg aatgcaagac taaagtagac caaacatgtc   51180
aatttcgttg aacataattt ggtcagactt taaggtgaag gcataaagaa atcaaataag   51240
agaaggactg aaaacaggaa tcaaccatca gtaatttcct aaaaatctag aacatgagta   51300
tagataattt ctttcaaata caaggaaaa agttgtgggt tttttttttt ttacttcaaa   51360
aattcaacta gagaatgcta cagttaaagt gtacctgaaa ccaaatttgg tgaatttaat   51420
aaccaagtca tttgctgcaa gatgttccaa gagttacaag ttattactca ggcgataacc   51480
tcaaatgact cccaagagtt aaattataaa ttttcctcaa caatagagag aattgatcag   51540
ttgagaacag agtcctcaaa gagcgaaaaa tggtgttatg cagaccccag tgtgtttgaa   51600
ggtgatacag agtatgcaaa tcttgatttt gcatctctga tcatagtgtt ggctctggga   51660
ttagttaaaa gacagaaatt cctcccttg tgtaactgta ctgtttcact taggttaacg   51720
taggtccttt aagactttgc tagtatgcca ttttaaactt gattggctct tagcccctcc   51780
caccatattt ttttcctcct gtcccataga aagggagca aggaagtgta aactaatggt   51840
cgtatagtga gaacacaaat gaatttttt tcttgatatt taccaagtgt gttcagcaaa   51900
cagttcttct gtgcctactt aattagtgcc agtcttaatc ctgggtacag agaggaaatc   51960
agatgtaatg tggtactagt gcctttttt ttttttacagt gtggaccctg gacaagagc   52020 ataggttgat atcacttgca agtttattac caatgccaac tcaggcttca ctcgagacct   52080
gctaattcag aatcagtatt tgaataaggt cccaggtgat ttgtacattg aagattttag   52140
aagtatacaa acagtaactc acagacatag taagatgaag agaaatccaa acagatgttt   52200
```

```
ggggctatgt cgtagatata gtataggcat aggaatccta aggagcagga catatttcag    52260
cctgaatatg acaaaaatcc cacttattac tctcctgaga gcttcaagtg cctatatgac    52320
ccaaaataca atggaaagcc tattggcgaa agtcatgggt tgattgatct aaccctgaga    52380
taaaatactt attaaaatat tatcttttaa tgggtttcag acaactgagg ctaagccctt    52440
taattacttt aaggaccatg ctcactgaag cttttaaaag gtattttcaa aagcttaatt    52500
gcccaagaaa ataatcagtg taagagtatt aggttaccca gcagaaaatg atgtcttcta    52560
catacctgtc tacatcacaa gaagggaggg gtaaaaaagg atcaagatct tattcttctg    52620
taagcctaca tgtgcatgag tgttatgatt ttgagactac tcttatatac atgtaatttg    52680
atcctcttat caaaacaata tagagaataa ctgagcccaa tcttttttagt catctcttca    52740 acaaggggta aatcagtcag tttctaaaac tggtgggagg tctccataaa cctgataaca    52800
agatcccaaa atccaaactg attgactgag ttaattcctg atcatttggg ttgaacttaa    52860
gagttataca agaaaatggt aggggacgag gaggttgtat aaaggggaaa aaacaacaac    52920
tgcaaaaagc ccaagagcct gaatttagac caatctatca tcttcctcct cttaaaaga    52980 aaacaattta aaagttttaa ataaaaaata aaggtcatgt ttttgttttg ccaagaatca    53040
aaagattttg ctgaaactac tgctgcaaaa tattttgttt caagccatct tagggcacct    53100
cagactaaaa atgaaccat gatcaatttc tatcccctta ccacttctat gacaatcaca    53160
catggtaaat acaagctctg ctctagtact acaataaaac tgtagaacta gagtagacct    53220
tgtagtgatc atatattact acttctcctc ttgtcctatg tccatcttat ttcaatctaa    53280
actagaaatg acaaaattct tgttgggtcg aattgtcttt tgagtagttt tagagctttt    53340
tgttttcatt tctccaagat gatcttgttg catctgcagt tcgagttttt aaaatcaagt    53400
agaataatgt caaaggggga caatttatgt gagaaatcaa ctgacagtac atgattattt    53460
aaaatgaaag ttttaaagaa aattttcccc acaagggaat ctgtgtaaga ccagaaatct    53520
tatgattggc tagctactat ataaaatgct ctgtacacaa gaaatatttt ctattgtccc    53580
tagccagtaa acaagaaca aactcgtacc aaacatgaac tacagtatat ttatactgct    53640
gtgctaaatg tgtttgtgg gtatgttttt cttctctcta ggggagagta cggtttccat    53700
gaatatacag aggtcaaaac agtcacagtg aaaatctctc agaagaactc ataaagaaaa    53760
tacaagagtg gagagaagct cttcaatagc taagcatctc cttacagtca ctaatatagt    53820 agatttaaa gacaaaattt ttcttttctt gatttttta aacataagct aaatcatatt    53880
agtattaata ctacccatag aaaacttgac atgtagcttc ttctgaaaga attatttgcc    53940
ttctgaaatg tgaccccccaa gtcctatcct aaataaaaaa agacaaattc ggatgtatga    54000
tctctctagc tttgtcatag ttatgtgatt ttcctttgta gctacttttg caggataata    54060
attttataga aaaggaacag ttgcatttag cttctttccc ttagtgactc ttgaagtact    54120
taacatacac gttaactgca gagtaaattg ctctgttccc agtagttata aagtccttgg    54180
actgttttga aaagtttcct aggatgtcat gtctgcttgt caaagaaat aatccctgta    54240 atatttagct gtaaactgaa tataaagctt aataaaaaca accttgcatg attcttgtta    54300
cttttgaatt ttttaagta caagtttggg ttacagtgat ttcttcttgt cacttaaaaa    54360
cagtgttaaa ctgagcataa aggtacattt aaaagtaaaa gtctaatcca cctattctca    54420
aataggtaaa gaaacatgct gtattttcca aaagaattct caaaatcagt ggatttttatc    54480 tgaaatagat ggcctcagtc cttcagtaag caattattga gttcctacaa agttttgggt    54540
atgtgttaag tgttgtagaa aagaggtgaa taatgaatgg tccattatct gaagatcttt    54600
```

-continued

```
aatttagtgg ttaataaaga cacaatccct gcaccacaga aaggaggggt cataaaaaaa   54660
atgaggattt tagaaacttg tagtgacttg cagaagtggt catgatgaag gctaactgag   54720
ggaatcagga atggcctcag gtaggaaatt tgactgaata taaaccttaa taatgggcaa   54780
atttgcaatg aataaagggg aaagaggttc tacaaaattt atcaggacat gttccattga   54840
aaaaacattc ggaaaaattc tatacaatat attttcctct cttggaattt cagattgcac   54900
atcggcagca tattataggt ttcgagaagt cctgcaacct tcttagtttt aatagagccc   54960
cccctttttt tttccaaatt agcagagact ttgtctcctc tccctcacct cctcagttac   55020
caccaattaa cattaagaaa cccatgctgg gctgaataca gtggctcact cctgtaatcc   55080
tagcactttg ggaggccaca gcaggtggat ctgttgagcc caggagtttg agaccagcct   55140
gggcaatggg caaaatccca cctttattta aaaaaaaaa ttagccaggc ataggggcac   55200
aaacctgtgg tcccatctac atgagaggct gaggcaggag gatggcttga acctgggagg   55260
tcgaggctgc agtgagccat gatcatacta ctgcactcta gcctgggtga cagagtggga   55320
ccctgtttca aaataaaaa taaaaataaa aacccttgct gtcctatgca atgagggaac   55380
ccttagagtt ctaaggagag atctgggaat caaaagagag cagctgaaaa aaatgtcctc   55440
cacatgaaac tacaccaagc t                                            55461
```

<210> SEQ ID NO 7
<211> LENGTH: 466
<212> TYPE: PRT
<213> ORGANISM: Homo sapiens
<220> FEATURE:
<223> OTHER INFORMATION: vimentin (VIM), epidiymis luminal protein 113
      (HEL113), CTRCT30

<400> SEQUENCE: 7

```
Met Ser Thr Arg Ser Val Ser Ser Ser Tyr Arg Arg Met Phe Gly
 1               5                  10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
    65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
```

-continued

```
                195                 200                 205
Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465
```

<210> SEQ ID NO 8
<211> LENGTH: 2151
<212> TYPE: DNA
<213> ORGANISM: Homo sapiens
<220> FEATURE:
<223> OTHER INFORMATION: vimentin (VIM), epidiymis luminal protein 113
      (HEL113), CTRCT30

<400> SEQUENCE: 8

```
gcctctccaa aggctgcaga agtttcttgc taacaaaaag tccgcacatt cgagcaaaga      60
caggctttag cgagttatta aaaacttagg ggcgctcttg tcccccacag ggcccgaccg     120
cacacagcaa ggcgatggcc cagctgtaag ttggtagcac tgagaactag cagcgcgcgc     180
ggagcccgct gagacttgaa tcaatctggt ctaacggttt cccctaaacc gctaggagcc     240
ctcaatcggc gggacagcag ggcgcgtcct ctgccactct cgctccgagg tccccgcgcc     300
agagacgcag ccgcgctccc accacccaca cccaccgcgc cctcgttcgc ctcttctccg     360
ggagccagtc cgcgccaccg ccgccgccca ggcatcgcc accctccgca gccatgtcca     420
ccaggtccgt gtcctcgtcc tctaccgca ggatgttcgg cggcccgggc accgcgagcc     480
```

```
ggccgagctc cagccggagc tacgtgacta cgtccacccg cacctacagc ctgggcagcg    540
cgctgcgccc cagcaccagc cgcagcctct acgcctcgtc cccgggcggc gtgtatgcca    600
cgcgctcctc tgccgtgcgc ctgcggagca gcgtgcccgg ggtgcggctc ctgcaggact    660
cggtggactt ctcgctggcc gacgccatca acaccgagtt caagaacacc cgcaccaacg    720
agaaggtgga gctgcaggag ctgaatgacc gcttcgccaa ctacatcgac aaggtgcgct    780
tcctggagca gcagaataag atcctgctgg ccgagctcga gcagctcaag ggccaaggca    840
agtcgcgcct gggggacctc tacgaggagg agatgcggga gctgcgccgg caggtggacc    900
agctaaccaa cgacaaagcc cgcgtcgagg tggagcgcga caacctggcc gaggacatca    960
tgcgcctccg ggagaaattg caggaggaga tgcttcagag agaggaagcc gaaaacaccc   1020
tgcaatcttt cagacaggat gttgacaatg cgtctctggc acgtcttgac cttgaacgca   1080
aagtggaatc tttgcaagaa gagattgcct ttttgaagaa actccacgaa gaggaaatcc   1140
aggagctgca ggctcagatt caggaacagc atgtccaaat cgatgtggat gtttccaagc   1200
ctgacctcac ggctgccctg cgtgacgtac gtcagcaata tgaaagtgtg ctgccaaga    1260 acctgcagga ggcagaagaa tggtacaaat ccaagtttgc tgacctctct gaggctgcca   1320
accggaacaa tgacgccctg cgccaggcaa agcaggagtc cactgagtac cggagacagg   1380
tgcagtccct cacctgtgaa gtggatgcct taaaggaac caatgagtcc ctggaacgcc    1440
agatgcgtga atggaagag acttttgccg ttgaagctgc taactaccaa gacactattg    1500
gccgcctgca ggatgagatt cagaatatga aggaggaaat ggctcgtcac cttcgtgaat   1560
accaagacct gctcaatgtt aagatggccc ttgacattga gattgccacc tacaggaagc   1620
tgctggaagg cgaggagagc aggatttctc tgcctcttcc aaactttcc tccctgaacc    1680 tgagggaaac taatctggat tcactccctc tggttgatac ccactcaaaa aggacacttc   1740
tgattaagac ggttgaaact agagatggac aggttatcaa cgaaacttct cagcatcacg   1800
atgaccttga ataaaaattg cacacactca gtgcagcaat atattaccag caagaataaa   1860
aaagaaatcc atatcttaaa gaaacagctt tcaagtgcct ttctgcagtt tttcaggagc   1920
gcaagataga tttggaatag gaataagctc tagttcttaa caaccgacac tcctacaaga   1980
tttagaaaaa agtttacaac ataatctagt ttacagaaaa atcttgtgct agaatacttt    2040 ttaaaggta ttttgaatac cattaaaact gctttttttt ttccagcaag tatccaacca    2100
acttggttct gcttcaataa atctttggaa aaactcaaaa aaaaaaaaa a             2151
```

<210> SEQ ID NO 9
<211> LENGTH: 781
<212> TYPE: PRT
<213> ORGANISM: Homo sapiens
<220> FEATURE:
<223> OTHER INFORMATION: beta-catenin (CTNNB), catenin beta-1 (CTNNB1),
      cadherin-associated protein, armadillo homolog, MRD19

<400> SEQUENCE: 9

```
Met Ala Thr Gln Ala Asp Leu Met Glu Leu Asp Met Ala Met Glu Pro
 1               5                  10                  15

Asp Arg Lys Ala Ala Val Ser His Trp Gln Gln Gln Ser Tyr Leu Asp
             20                  25                  30

Ser Gly Ile His Ser Gly Ala Thr Thr Thr Ala Pro Ser Leu Ser Gly
         35                  40                  45

Lys Gly Asn Pro Glu Glu Glu Asp Val Asp Thr Ser Gln Val Leu Tyr
     50                  55                  60
```

```
Glu Trp Glu Gln Gly Phe Ser Gln Ser Phe Thr Gln Glu Gln Val Ala
 65                  70                  75                  80

Asp Ile Asp Gly Gln Tyr Ala Met Thr Arg Ala Gln Arg Val Arg Ala
                 85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
            245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
            325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Ile Asn Val
            405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480
```

```
Ala Gln Asn Ala Val Arg Leu His Tyr Gly Leu Pro Val Val Lys
                485                 490                 495

Leu Leu His Pro Pro Ser His Trp Pro Leu Ile Lys Ala Thr Val Gly
        500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
770                 775                 780

<210> SEQ ID NO 10
<211> LENGTH: 3256
<212> TYPE: DNA
<213> ORGANISM: Homo sapiens
<220> FEATURE:
<223> OTHER INFORMATION: beta-catenin (CTNNB), catenin beta-1 (CTNNB1)
      transcript variant 3, cadherin-associated protein, armadillo
      homolog, MRD19

<400> SEQUENCE: 10
aggatacagc ggcttctgcg cgacttataa gagctccttg tgcggcgcca ttttaagcct    60
ctcggtctgt ggcagcagcg ttggcccggc cccgggagcg gagagcgagg ggaggcggag   120
acggaggaag gtctgaggag cagcttcagt ccccgccgag ccgccaccgc aggtcgagga   180
cggtcggact cccgcggcgg gaggagcctg ttccctgag ggtatttgaa gtataccata   240
caactgtttt gaaaatccag cgtggacaat ggctactcaa gctgatttga tggagttgga   300
```

```
catggccatg gaaccagaca gaaaagcggc tgttagtcac tggcagcaac agtcttacct      360
ggactctgga atccattctg gtgccactac cacagctcct tctctgagtg gtaaaggcaa      420
tcctgaggaa gaggatgtgg atacctccca gtcctgtat  gagtgggaac agggattttc      480
tcagtccttc actcaagaac aagtagctga tattgatgga cagtatgcaa tgactcgagc      540
tcagagggta cgagctgcta tgttccctga cattagat   gagggcatgc agatcccatc      600
tacacagttt gatgctgctc atcccactaa tgtccagcgt ttggctgaac catcacagat      660
gctgaaacat gcagttgtaa acttgattaa ctatcaagat gatgcagaac ttgccacacg      720
tgcaatccct gaactgacaa aactgctaaa tgacgaggac caggtggtgg ttaataaggc      780
tgcagttatg gtccatcagc tttctaaaaa ggaagcttcc agacacgcta tcatgcgttc      840
tcctcagatg gtgtctgcta ttgtacgtac catgcagaat acaaatgatg tagaaacagc      900
tcgttgtacc gctgggacct tgcataacct ttcccatcat cgtgagggct tactggccat      960
ctttaagtct ggaggcattc ctgccctggt gaaaatgctt ggttcaccag tggattctgt     1020
gttgttttat gccattacaa ctctccacaa ccttttatta catcaagaag gagctaaaat     1080
ggcagtgcgt ttagctggtg ggctgcagaa aatggttgcc ttgctcaaca aaacaaatgt     1140
taaattcttg gctattacga cagactgcct tcaaattta  gcttatggca accaagaaag     1200
caagctcatc atactggcta gtggtggacc ccaagcttta gtaaatataa tgaggaccta     1260
tacttacgaa aaactactgt ggaccacaag cagagtgctg aaggtgctat ctgtctgctc     1320
tagtaataag ccggctattg tagaagctgg tggaatgcaa gctttaggac ttcacctgac     1380
agatccaagt caacgtcttg ttcagaactg tctttggact ctcaggaatc tttcagatgc     1440
tgcaactaaa caggaaggga tggaaggtct ccttgggact cttgttcagc ttctgggttc     1500
agatgatata aatgtggtca cctgtgcagc tggaattctt tctaacctca cttgcaataa     1560
ttataagaac aagatgatgg tctgccaagt gggtggtata gaggctcttg tgcgtactgt     1620
ccttcgggct ggtgacaggg aagacatcac tgagcctgcc atctgtgctc ttcgtcatct     1680
gaccagccga caccaagaag cagagatggc ccagaatgca gttcgccttc actatggact     1740
accagttgtg gttaagctct acacccacc  atcccactgg cctctgataa aggctactgt     1800
tggattgatt cgaaatcttg cccttttgtcc cgcaaatcat gcacctttgc gtgagcaggg     1860
tgccattcca cgactagttc agttgcttgt tcgtgcacat caggataccc agcgccgtac     1920
gtccatgggt gggacacagc agcaatttgt ggaggggtc  cgcatggaag aaatagttga     1980
aggttgtacc ggagcccttc acatcctagc tcgggatgtt cacaaccgaa ttgttatcag     2040
aggactaaat accattccat tgtttgtgca gctgctttat tctcccattg aaaacatcca     2100
aagagtagct gcaggggtcc tctgtgaact tgctcaggac aaggaagctg cagaagctat     2160
tgaagctgag ggagccacag ctcctctgac agagttactt cactctagga atgaaggtgt     2220
ggcgacatat gcagctgctg tttttgttccg aatgtctgag acaagccac  aagattacaa     2280
gaaacggctt tcagttgagc tgaccagctc tctcttcaga acagagccaa tggcttggaa     2340
tgagactgct gatcttggac ttgatattgg tgcccaggga gaacccttg  atatcgcca      2400
ggatgatcct agctatcgtt cttttcactc tggtggatat ggccaggatg ccttgggtat     2460
ggaccccatg atggaacatg agatgggtgg ccaccaccct ggtgctgact atccagttga     2520
tgggctgcca gatctgggc  atgcccagga cctcatggat gggctgcctc caggtgacag     2580
caatcagctg gcctggtttg atactgacct gtaaatcatc ctttaggagt aacaatacaa     2640
atggattttg ggagtgactc aagaagtgaa gaatgcacaa gaatggatca caagatggaa     2700
```

```
tttatcaaac cctagccttg cttgttaaat tttttttttt ttttttttaa gaatatctgt    2760
aatggtactg actttgcttg ctttgaagta gctcttttt tttttttttt tttttttttg    2820
cagtaactgt tttttaagtc tctcgtagtg ttaagttata gtgaatactg ctacagcaat    2880
ttctaatttt taagaattga gtaatggtgt agaacactaa ttcataatca ctctaattaa    2940
ttgtaatctg aataaagtgt aacaattgtg tagcctttt gtataaaata gacaaataga    3000
aaatggtcca attagtttcc ttttaatat gcttaaaata agcaggtgga tctatttcat    3060 gttttttgatc aaaaactatt tgggatatgt atgggtaggg taaatcagta agaggtgtta    3120 tttgaacct tgttttggac agtttaccag ttgccttta tcccaaagtt gttgtaacct     3180
gctgtgatac gatgcttcaa gagaaaatgc ggttataaaa aatggttcag aattaaactt    3240
ttaattcatt cgattg                                                    3256
```

<210> SEQ ID NO 11
<211> LENGTH: 387
<212> TYPE: PRT
<213> ORGANISM: Homo sapiens
<220> FEATURE:
<223> OTHER INFORMATION: milk fat globule-EGF factor 8 protein (MFGE8,
      MFG-E8), lactadherin isoform a preprotein, sperm associated
      antigen 10 (SPAG10), O-acetyl disialogangliocide synthase
      (OAcGD3S), medin, sperm surface protein hP47, breast epithelial
      antigen BA46

<400> SEQUENCE: 11

```
Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
        50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240
```

```
Ile Pro Asp Lys Gln Ile Thr Ala Ser Ser Tyr Lys Thr Trp Gly
            245                 250                 255
Leu His Leu Phe Ser Trp Asn Pro Ser Tyr Ala Arg Leu Asp Lys Gln
                260                 265                 270
Gly Asn Phe Asn Ala Trp Val Ala Gly Ser Tyr Gly Asn Asp Gln Trp
            275                 280                 285
Leu Gln Val Asp Leu Gly Ser Ser Lys Glu Val Thr Gly Ile Ile Thr
        290                 295                 300
Gln Gly Ala Arg Asn Phe Gly Ser Val Gln Phe Val Ala Ser Tyr Lys
305                 310                 315                 320
Val Ala Tyr Ser Asn Asp Ser Ala Asn Trp Thr Glu Tyr Gln Asp Pro
                325                 330                 335
Arg Thr Gly Ser Ser Lys Ile Phe Pro Gly Asn Trp Asp Asn His Ser
            340                 345                 350
His Lys Lys Asn Leu Phe Glu Thr Pro Ile Leu Ala Arg Tyr Val Arg
        355                 360                 365
Ile Leu Pro Val Ala Trp His Asn Arg Ile Ala Leu Arg Leu Glu Leu
    370                 375                 380
Leu Gly Cys
385

<210> SEQ ID NO 12
<211> LENGTH: 2005
<212> TYPE: DNA
<213> ORGANISM: Homo sapiens
<220> FEATURE:
<223> OTHER INFORMATION: milk fat globule-EGF factor 8 protein (MFGE8,
      MFG-E8), lactadherin transcript variant 1, sperm associated
      antigen 10 (SPAG10), O-acetyl disialogangliocide synthase
      (OAcGD3S), medin, sperm surface protein hP47, breast epithelial
      antigen BA46

<400> SEQUENCE: 12
agtgggaggt gctgagccgc ctgatttatt ccggtcccag aggagaaggc gccagaaccc    60
cgcggggtct gagcagccca gcgtgcccat tccagcgccc gcgtccccgc agcatgccgc   120
gcccccgcct gctggccgcg ctgtgcggcg cgctgctctg cgcccccagc ctcctcgtcg   180
ccctggatat ctgttccaaa accccctgcc acaacggtgg tttatgcgag gagatttccc   240
aagaagtgcg aggagatgtc ttcccctcgt acacctgcac gtgccttaag gctacgcgg   300 gcaaccactg tgagacgaaa tgtgtcgagc cactgggcct ggagaatggg aacattgcca   360
actcacagat cgccgcctcg tctgtgcgtg tgaccttctt gggtttgcag cattgggtcc   420
cggagctggc ccgcctgaac cgcgcaggca tggtcaatgc ctggacaccc agcagcaatg   480
acgataaccc ctggatccag gtgaacctgc tgcggaggat gtgggtaaca ggtgtggtga   540
cgcagggtgc cagccgcttg gccagtcatg agtacctgaa ggccttcaag gtggcctaca   600
gccttaatgg acacgaattc gatttcatcc atgatgttaa taaaaacac aaggagtttg   660 tgggtaactg gaacaaaaac gcggtgcatg tcaacctgtt tgagacccct gtggaggctc   720
agtacgtgag attgtacccc acgagctgcc acacggcctg cactctgcgc tttgagctac   780
tgggctgtga gctgaacgga tgcgccaatc cctgggcct gaagaataac agcatccctg   840
acaagcagat cacggcctcc agcagctaca agacctgggg cttgcatctc ttcagctgga   900
accccctcta tgcacggctg gacaagcagg gcaacttcaa cgcctgggtt gcggggagct   960
acggtaacga tcagtggctg caggtggacc tgggctcctc gaaggaggtg acaggcatca  1020
```

-continued

```
tcacccaggg ggcccgtaac tttggctctg tccagtttgt ggcatcctac aaggttgcct    1080
acagtaatga cagtgcgaac tggactgagt accaggaccc caggactggc agcagtaaga    1140
tcttccctgg caactgggac aaccactccc acaagaagaa cttgtttgag acgcccatcc    1200
tggctcgcta tgtgcgcatc ctgcctgtag cctggcacaa ccgcatcgcc ctgcgcctgg    1260
agctgctggg ctgttagtgg ccacctgcca ccccaggtc ttcctgcttt ccatgggccc     1320
gctgcctctt ggcttctcag ccccttttaaa tcaccatagg gctggggact ggggaagggg   1380
agggtgttca gaggcagcac caccacacag tcacccctcc ctccctcttt cccaccctcc    1440
acctctcacg ggccctgccc cagccccctaa gcccgtccc ctaaccccca gtcctcactg     1500
tcctgttttc ttaggcactg agggatctga gtaggtctgg gatggacagg aaagggcaaa    1560
gtagggcgtg tggtttccct gccccctgtcc ggaccgccga tcccaggtgc gtgtgtctct   1620
gtctctccta gcccctctct cacacatcac attcccatgg tggcctcaag aaaggcccgg    1680
aagcgccagg ctggagataa cagcctcttg cccgtcggcc ctgcgtcggc cctgggtac    1740 catgtggcca caactgctgt ggcccccctgt ccccaagaca cttccccttg tctccctggt   1800
tgcctctctt gccccttgtc ctgaagccca gcgacacaga aggggggtggg gcgggtctat   1860 ggggagaaag ggagcgaggt cagaggaggg catgggttgg cagggtgggc gtttggggcc   1920
ctctatgctg gcttttcacc ccagaggaca caggcagctt ccaaaatata tttatcttct   1980
tcacgggaaa aaaaaaaaaa aaaaa                                          2005
```

<210> SEQ ID NO 13
<211> LENGTH: 354
<212> TYPE: PRT
<213> ORGANISM: Homo sapiens
<220> FEATURE:
<223> OTHER INFORMATION: macrophage antigen CD68, microsialin isoform A precursor, lysosomal/endosomal-associated membrane glycoprotein 4 (LAMP4), scavenger receptor class D, member 1 (SCARD1), GP110

<400> SEQUENCE: 13

```
Met Arg Leu Ala Val Leu Phe Ser Gly Ala Leu Leu Gly Leu Leu Ala
 1               5                  10                  15

Ala Gln Gly Thr Gly Asn Asp Cys Pro His Lys Lys Ser Ala Thr Leu
            20                  25                  30

Leu Pro Ser Phe Thr Val Thr Pro Thr Val Thr Glu Ser Thr Gly Thr
        35                  40                  45

Thr Ser His Arg Thr Thr Lys Ser His Lys Thr Thr Thr His Arg Thr
    50                  55                  60

Thr Thr Thr Gly Thr Thr Ser His Gly Pro Thr Thr Ala Thr His Asn
65                  70                  75                  80

Pro Thr Thr Thr Ser His Gly Asn Val Thr Val His Pro Thr Ser Asn
                85                  90                  95

Ser Thr Ala Thr Ser Gln Gly Pro Ser Thr Ala Thr His Ser Pro Ala
            100                 105                 110

Thr Thr Ser His Gly Asn Ala Thr Val His Pro Thr Ser Asn Ser Thr
        115                 120                 125

Ala Thr Ser Pro Gly Phe Thr Ser Ser Ala His Pro Glu Pro Pro Pro
    130                 135                 140

Pro Ser Pro Ser Pro Ser Pro Thr Ser Lys Glu Thr Ile Gly Asp Tyr
145                 150                 155                 160

Thr Trp Thr Asn Gly Ser Gln Pro Cys Val His Leu Gln Ala Gln Ile
                165                 170                 175
```

```
Gln Ile Arg Val Met Tyr Thr Thr Gln Gly Gly Glu Ala Trp Gly
            180                 185                 190
Ile Ser Val Leu Asn Pro Asn Lys Thr Lys Val Gln Gly Ser Cys Glu
        195                 200                 205
Gly Ala His Pro His Leu Leu Leu Ser Phe Pro Tyr Gly His Leu Ser
    210                 215                 220
Phe Gly Phe Met Gln Asp Leu Gln Gln Lys Val Val Tyr Leu Ser Tyr
225                 230                 235                 240
Met Ala Val Glu Tyr Asn Val Ser Phe Pro His Ala Ala Gln Trp Thr
                245                 250                 255
Phe Ser Ala Gln Asn Ala Ser Leu Arg Asp Leu Gln Ala Pro Leu Gly
            260                 265                 270
Gln Ser Phe Ser Cys Ser Asn Ser Ser Ile Ile Leu Ser Pro Ala Val
        275                 280                 285
His Leu Asp Leu Leu Ser Leu Arg Leu Gln Ala Ala Gln Leu Pro His
    290                 295                 300
Thr Gly Val Phe Gly Gln Ser Phe Ser Cys Pro Ser Asp Arg Ser Ile
305                 310                 315                 320
Leu Leu Pro Leu Ile Ile Gly Leu Ile Leu Gly Leu Leu Ala Leu
                325                 330                 335
Val Leu Ile Ala Phe Cys Ile Ile Arg Arg Arg Pro Ser Ala Tyr Gln
            340                 345                 350
Ala Leu

<210> SEQ ID NO 14
<211> LENGTH: 1872
<212> TYPE: DNA
<213> ORGANISM: Homo sapiens
<220> FEATURE:
<223> OTHER INFORMATION: macrophage antigen CD68, microsialin transcript
      variant 1, lysosomal/endosomal-associated membrane glycoprotein 4
      (LAMP4), scavenger receptor class D, member 1 (SCARD1), GP110

<400> SEQUENCE: 14
ttaattacaa aaactaatga ctaagagaga ggtggctaga gctgaggccc ctgagtcagg     60
ctgtgggtgg gatcatctcc agtacaggaa gtgagacttt catttcctcc tttccaagag    120
agggctgagg gagcagggtt gagcaactgg tgcagacagc ctagctggac tttgggtgag    180
gcggttcagc catgaggctg gctgtgcttt tctcgggggc cctgctgggg ctactggcag    240
cccaggggac agggaatgac tgtcctcaca aaaatcagc tactttgctg ccatccttca    300
cggtgacacc cacggttaca gagagcactg gaacaaccag ccacaggact accaagagcc    360
acaaaaccac cactcacagg acaaccacca caggcaccac cagccacgga cccacgactg    420
ccactcacaa ccccaccacc accagccatg gaaacgtcac agttcatcca acaagcaata    480
gcactgccac cagccaggga ccctcaactg ccactcacag tcctgccacc actagtcatg    540
gaaatgccac ggttcatcca acaagcaaca gcactgccac cagcccagga ttcaccagtt    600
ctgcccaccc agaaccacct ccaccctctc cgagtcctag cccaacctcc aaggagacca    660
ttggagacta cacgtggacc aatggttccc agccctgtgt ccacctccaa gcccagattc    720
agattcgagt catgtacaca acccagggtg gaggagaggc tgggggcatc tctgtactga    780
accccaacaa aaccaaggtc cagggaagct gtgagggtgc ccatccccac ctgcttctct    840
cattccccta tggacacctc agctttggat tcatgcagga cctccagcag aaggttgtct    900
acctgagcta catggcggtg gagtacaatg tgtccttccc ccacgcagca cagtggacat    960
```

-continued

```
tctcggctca gaatgcatcc cttcgagatc tccaagcacc cctggggcag agcttcagtt    1020
gcagcaactc gagcatcatt ctttcaccag ctgtccacct cgacctgctc tccctgaggc    1080
tccaggctgc tcagctgccc cacacagggg tctttgggca aagtttctcc tgccccagtg    1140
accggtccat cttgctgcct ctcatcatcg gcctgatcct tcttggcctc ctcgccctgg    1200
tgcttattgc tttctgcatc atccggagac gcccatccgc ctaccaggcc ctctgagcat    1260
ttgcttcaaa ccccagggca ctgagggggt tggggtgtgg tgggggggta cccttatttc    1320
ctcgacacgc aactggctca aagacaatgt tattttcctt ccctttcttg aagaacaaaa    1380
agaaagccgg gcatgacggc tcatgcctgt aatcccagca ctttgggagg ctgaggcagg    1440
tggatcactg gaggtcagga gtttgagacc agcctggcca acatggtgaa accctgtctc    1500
tactaaaaat acaattagcc aggtgtggcg gcgtaatccc agctggcctg taatcccagc    1560
tacttgggag gctgaggcag aactgcttga acccaggagg tggaggttgc agtgagccgt    1620
catcgcgcca ctaagccaag atcgcgccac tgcactccag cctgggcgac agagccagac    1680
tgtctcaaat aaataaatat gagataatgc agtcgggaga agggagggag agaattttat    1740
taaatgtgac gaactgcccc cccccccccc ccagcaggag agcagcaaaa tttatgcaaa    1800
tctttgacgg ggttttcctt gtcctgccag gattaaaagc catgagtttc ttgtcaaaaa    1860
aaaaaaaaaa aa                                                        1872
```